(12) United States Patent
Caldeira et al.

(10) Patent No.: US 9,033,497 B2
(45) Date of Patent: May 19, 2015

(54) OPTICAL DEVICE WITH INTERCHANGEABLE CORRECTIVE ELEMENTS

(75) Inventors: Kenneth G. Caldeira, Redwood City, CA (US); Peter L. Hagelstein, Carlisle, MA (US); Roderick A. Hyde, Redmond, WA (US); Edward K. Y. Jung, Bellevue, WA (US); Jordin T. Kare, Seattle, WA (US); Nathan P. Myhrvold, Medina, WA (US); John Brian Pendry, Cobham (GB); David Schurig, Salt Lake City, UT (US); Clarence T. Tegreene, Bellevue, WA (US); Charles Whitmer, North Bend, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 6 days.

(21) Appl. No.: 13/506,085

(22) Filed: Mar. 22, 2012

(65) Prior Publication Data
US 2013/0173029 A1    Jul. 4, 2013

Related U.S. Application Data

(63) Continuation-in-part of application No. 13/385,688, filed on Feb. 29, 2012, and a continuation-in-part of application No. 13/385,689, filed on Feb. 29, 2012, and a continuation-in-part of application No.
(Continued)

(51) Int. Cl.
*A61B 3/10* (2006.01)
*G02C 5/00* (2006.01)
(Continued)

(52) U.S. Cl.
CPC .................................. *G02C 13/001* (2013.01)

(58) Field of Classification Search
USPC .................... 351/159.74, 200, 203, 205, 206, 351/209–210, 220–223, 227–231, 246, 41, 351/47, 52, 57, 110, 116, 159, 177
See application file for complete search history.

(56) References Cited

U.S. PATENT DOCUMENTS 4,105,302 A * 8/1978 Tate, Jr. .......................... 351/210
4,418,990 A   12/1983 Gerber
(Continued)

FOREIGN PATENT DOCUMENTS

WO    WO 90/05926    5/1990

OTHER PUBLICATIONS

Abramowitz, Mortimer et al.; "Eyepieces (Oculars)"; 2010; pp. 1-9; Olympus America Inc.; located at http://www.olympusmicro.com/primer/anatomy/oculars.html.
(Continued)

*Primary Examiner* — Dawayne A Pinkney

(57) ABSTRACT

Exemplary embodiments enable an enhanced direct-viewing optical device to include customized adjustments that accommodate various optical aberrations of a current user. Customized optical elements associated with an authorized current user are incorporated with the direct-viewing optical device to produce a specified change in optical wavefront at an exit pupil. Possible replacement optical elements may have refractive and/or reflective and/or diffractive and/or transmissive characteristics based on current performance viewing factors for a given field of view of the direct-viewing optical device. Some embodiments enable dynamic repositioning and/or transformation of replaceable corrective optical elements responsive to a detected shift of a tracked gaze direction of a current user. Replaceable interchangeable corrective optical elements may be fabricated for current usage or retained in inventory for possible future usage in designated direct-viewing optical devices.

38 Claims, 72 Drawing Sheets

Related U.S. Application Data

13/374,533, filed on Dec. 29, 2011, and a continuation-in-part of application No. 13/374,520, filed on Dec. 29, 2011, and a continuation-in-part of application No. 13/374,517, filed on Dec. 29, 2011.

(51) Int. Cl.
*A61B 3/00* (2006.01)
*A61B 3/02* (2006.01)
*A61B 3/04* (2006.01)
*G02C 13/00* (2006.01)

(56) References Cited

U.S. PATENT DOCUMENTS

| | | | |
|---|---|---|---|
| 4,724,454 A | 2/1988 | Misawa | |
| 4,936,667 A | 6/1990 | Röhr et al. | |
| 4,955,702 A | 9/1990 | Nakamura | |
| 5,090,796 A | 2/1992 | Feinbloom | |
| 5,182,585 A | 1/1993 | Stoner | |
| 5,483,301 A | 1/1996 | Clarke | |
| 5,835,289 A | 11/1998 | Berry | |
| 6,058,090 A | 5/2000 | Wang et al. | |
| 6,478,425 B2 | 11/2002 | Trajkovic et al. | |
| 6,480,339 B2 | 11/2002 | Clark | |
| 6,511,180 B2 | 1/2003 | Guirao et al. | |
| 6,568,809 B2 | 5/2003 | Trajkovic et al. | |
| 6,709,108 B2 | 3/2004 | Levine et al. | |
| 6,761,454 B2 | 7/2004 | Lai et al. | |
| 6,786,602 B2 | 9/2004 | Abitbol | |
| 7,009,161 B2 | 3/2006 | Hoffmann | |
| 7,021,764 B2 | 4/2006 | Dreher | |
| 7,086,928 B2 | 8/2006 | Siders et al. | |
| 7,246,906 B2 | 7/2007 | Mihashi et al. | |
| 7,268,890 B2 | 9/2007 | Emer | |
| 7,303,281 B2 | 12/2007 | Wakil et al. | |
| 7,334,894 B2 | 2/2008 | Hillis et al. | |
| 7,365,738 B2 | 4/2008 | Molander et al. | |
| 7,371,041 B2 | 5/2008 | Pfeiffer et al. | |
| 7,384,146 B2 | 6/2008 | Covannon et al. | |
| 7,387,387 B2 | 6/2008 | Dai | |
| 7,412,711 B2 | 8/2008 | Jernstrom et al. | |
| 7,490,936 B2 | 2/2009 | Blum et al. | |
| 7,500,750 B2 | 3/2009 | Sabeta | |
| 7,568,799 B2 | 8/2009 | Dreher et al. | |
| 7,599,122 B2 | 10/2009 | Liao | |
| 7,697,212 B2 | 4/2010 | Jethmalani et al. | |
| 7,699,471 B2 | 4/2010 | Lai | |
| 7,708,401 B2 | 5/2010 | Sabeta | |
| 7,708,405 B2 | 5/2010 | Chernyak | |
| 7,724,454 B2 | 5/2010 | Lin | |
| 7,726,811 B2 | 6/2010 | Lai | |
| 7,736,000 B2 | 6/2010 | Enriquez et al. | |
| 7,815,310 B2 | 10/2010 | Su et al. | |
| 7,824,033 B2 | 11/2010 | Lai | |
| 7,832,863 B2 | 11/2010 | Dreher et al. | |
| 8,047,651 B2 | 11/2011 | Blum et al. | |
| 8,246,609 B2 | 8/2012 | Zickler et al. | |
| 2002/0071095 A1 | 6/2002 | Roffman et al. | |
| 2002/0104961 A1 | 8/2002 | Hoffmann | |
| 2002/0113943 A1 | 8/2002 | Trajkovic et al. | |
| 2003/0053028 A1 | 3/2003 | Wirth | |
| 2004/0057014 A1 | 3/2004 | Altmann | |
| 2004/0165284 A1 | 8/2004 | Holler | |
| 2005/0174535 A1 | 8/2005 | Lai et al. | |
| 2006/0192307 A1 | 8/2006 | Giller et al. | |
| 2006/0274261 A1* | 12/2006 | Andino et al. | 351/159 |
| 2007/0229756 A1 | 10/2007 | Mandler et al. | |
| 2008/0024594 A1 | 1/2008 | Ritchey | |
| 2008/0080846 A1 | 4/2008 | Grip | |
| 2008/0086207 A1 | 4/2008 | Sandstedt et al. | |
| 2008/0151175 A1 | 6/2008 | Gross | |
| 2008/0158502 A1* | 7/2008 | Becker et al. | 351/44 |
| 2008/0174732 A1* | 7/2008 | Blum et al. | 351/168 |
| 2008/0278808 A1 | 11/2008 | Redert | |
| 2009/0122265 A1 | 5/2009 | Dai et al. | |
| 2009/0251663 A1 | 10/2009 | Warden et al. | |
| 2010/0065625 A1 | 3/2010 | Sabeta | |
| 2010/0265463 A1 | 10/2010 | Lai | |
| 2010/0281021 A1 | 11/2010 | Weeber et al. | |
| 2011/0001930 A1 | 1/2011 | Levecq | |
| 2011/0157547 A1 | 6/2011 | Dillon et al. | |
| 2011/0221656 A1 | 9/2011 | Haddick et al. | |
| 2011/0221657 A1 | 9/2011 | Haddick et al. | |
| 2011/0228226 A1 | 9/2011 | Pixton et al. | |
| 2011/0250823 A1 | 10/2011 | Paillet et al. | |
| 2011/0299034 A1 | 12/2011 | Walsh et al. | |
| 2012/0218498 A1 | 8/2012 | Bonora et al. | |

OTHER PUBLICATIONS

"Active Focus Control for Deformable Mirrors"; Bridger Photonics; Nov. 21, 2011; pp. 1-3; located at http://www.bridgerphotonics.com/technology.php?product_id=36.

"Astigmatism"; A.D.A.M. Medical Encyclopedia; Jul. 28, 2011; 2 pages; A.D.A.M., Inc.

"Binoculars from the specialist"; Monk Optics; Nov. 7, 2011; pp. 1-4; located at http://www.monkoptics.co.uk/General/binocularterms.html.

Bush, Keith et al.; "Electrostatic Membrane Deformable Mirror Characterization and Applications"; Proc. SPIE, 2005; pp. 1-15; SPIE.

Cannistra, P. et al.; "Micro-transfer molding of SU-8 micro-optics"; Advanced Fabrication Technologies for Micro/Nano Optics and Photonics, Proc. of SPIE; 2008; pp. 68830C-1-68830C-9; vol. 6883.

"CD Player Operation"; Basic Car Audio Electronics; printed on Feb. 28, 2012; 8 pages; located at http://www.bcae1.com/cdplayer.htm.

Coe, Steve; "A Guide to Eyepieces"; printed on Dec. 14, 2011; pp. 1-3; located at http://www.saguaroastro.org/content/print-friendly/print-EYEPIECE.htm.

Cornelissen, S.A. et al.; "MEMS Deformable Mirrors for Astronomical Adaptive Optics"; Proc. of SPIE; 2010; pp. 77362D-1-77362D-10; vol. 7736, 77362D.

De Fez, Ma Dolores et al.; "Enhancement of Contrast Sensitivity and Losses of Chromatic Discrimination with Tinted Lenses"; Optometry and Vision Science; Sep. 2002; 8 pages; vol. 79, No. 9; American Academy of Optometry.

Dyer, David et al.; "Sequential shrink photolithography for plastic microlens arrays"; Applied Physics Letters; 2011; p. 034102-1-034102-3; vol. 99; American Institute of Physics.

Fu, Yong-Qi et al.; "Microfabrication of microlens array by focused ion beam technology"; Microelectronic Engineering; 2000; pp. 211-221; vol. 54; Elsevier Science B.V.

"Fundamentals of Remote Sensing—A Canada Centre for Remote Sensing Remote Sensing Tutorial"; Canada Centre for Remote Sensing; Oct. 27, 2011; pp. 39-42 and cover page; located at http://www.uprm.edu/biology/profs/chinea/gis/g06/NRC2_3_2_6.pdf.

Hawks, Chuck; "Binocular Basics"; 2010; pp. 1-7; located at http://www.chuckhawks.com/binocular_basics.htm.

Heiting, Gary; High-Definition Eyeglass Lenses; Aug. 2011; pp. 1-4; located at http://www.allaboutvision.com/lenses/wavefront-lenses.htm.

Kalloniatis, Michael et al.; "Visual Acuity"; Jun. 5, 2007; pp. 1-19; located at http://webvision.med.utah.edu/book/part-viii-gabac-receptors-visual-acuity/.

Kersten, Daniel et al.; "Convergence accommodation"; J. Opt. Soc. Am.; Mar. 1983; pp. 332-338; vol. 73, No. 3; Optical Society of America.

Krueger, Ronald R. et al.; Wavefront Customized Visual Correction—The Quest for Super Vision II; 2004; Chapter 33, cover and 1st page, and pp. 279-284; SLACK Incorporated.

"Lens Polishing Pressure Measurement & Analysis"; Tekscan, Inc.; 2007; pp. 1-5; located at http://www.tekscan.com/lens-polishing-pressure-distribution.

"Lightzone v3 Imaging—Imaging Introduction"; Sep. 6, 2011; pp. 1-5; located at http://www.photozone.de/lightzone-v205.

Love, Gordon D.; "Adaptive Optical Components Using Liquid Crystal Devices"; Journal of the Communications Research Laboratory; Nov. 1999; pp. 427-430; vol. 46, No. 3.

(56) References Cited

OTHER PUBLICATIONS

Meng, Fan-Yi et al.; Controllable Metamaterial-Loaded Waveguides Supporting Backward and Forward Waves; IEEE Transactions on Antennas and Propagation; Sep. 2011; pp. 3400-3411; vol. 59, No. 9; IEEE.

Millodot: Dictionary of Optometry and Visual Science, 7th Edition; "Convergence"; 2009; pp. 1-3; Butterworth-Heinemann; located at http://medical-dictionary.thefreedictionary.com/convergence.

Minin, I. V. et al.; "Subwavelength Diffractive Photonic Crystal Lens"; Progress in Electromagnetics Research B; 2008; pp. 257-264, vol. 7.

"Motorized Filter Flipper"; THORLABS; Feb. 1, 2012; pp. 1-2; located at http://www.thorlabs.com/NewGroupPage9.cfm?ObjectGroup_ID=3962.

"Ophthonix Introduces Customizable High-Resolution iZon(R) eFocusTM Computer Lens"; Ophthonix, Inc.; Mar. 22, 2011; 1 page.

"Optical Design"; celestron.com; Nov. 8, 2011; pp. 1-4; located at http://www.celestron.com/c2/popup_spec.php?ID=1.

"Stops and Apertures"; Nov. 8, 2011; pp. 1-10; located at http://electron9.phys.utk.edu/optics421/modules/m3/Stops.htm.

"Tech Talk Riflescopes"; Bushnell; 2011; pp. 1-5; located at http://www.bushnell.com/products/scopes/riflescopes/tech-talk/.

"The Compound Microscope"; microscopehelp.com; Nov. 8, 2011; pp. 1-3; located at http://www.microscopehelp.com/thecompoundmicroscope.html.

Thibos, Larry N. et al.; "Standards for Reporting the Optical Aberrations of Eyes"; Journal of Refractive Surgery; Sep./Oct. 2002; pp. S652-S660; vol. 18.

Tuteleers, P. et al.; "Investigation of the replication quality of plastic micro-optical interconnection components"; Proc. 6th An. Symp. IEEE/LEOS Benelux Chapter; 2001; pp. 73-77.

Tuteleers, P. et al.; "Replication of Refractive Micro Opto-mechanical Components Made with Deep Lithography with Protons"; Proceedings Symposium IEEE/LEOS Benelux Chapter; 2000; pp. 211-214.

Wikipedia; "File:HEXAGON-Figure.jpg"; Aug. 16, 2010; 2 pages; located at http://en.wikipedia.org/wiki/File:HEXAGON-Figure.jpg.

Wyant, James C. et al.; "Chapter 1: Basic Wavefront Aberration Theory for Optical Metrology"; 1992; pp. 1, 28-39; Academic Press, Inc.

Yao, Jun et al.; "Refractive micro lens array made of dichromate gelatin with gray-tone photolithography"; Microelectronic Engineering; 2001; pp. 729-735; vol. 57-58; Elsevier Science B.V.

"Z-View™ Aberrometer—The only lens made to the patient's unique optical fingerprint or iPrint™"; 2008; pp. 1-8; Informoptic Ch-1272 Genolier/VD Switzerland.

* cited by examiner

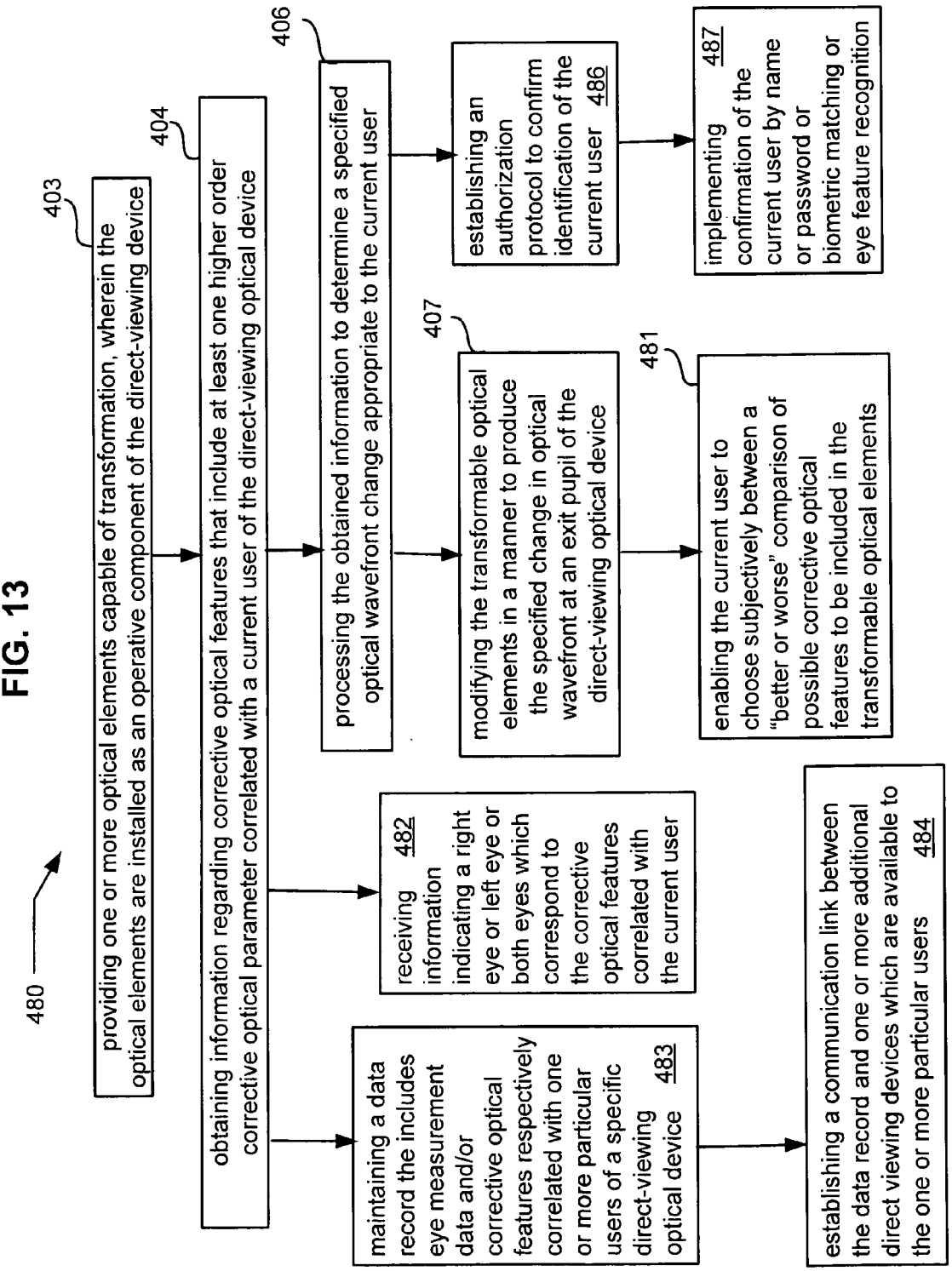

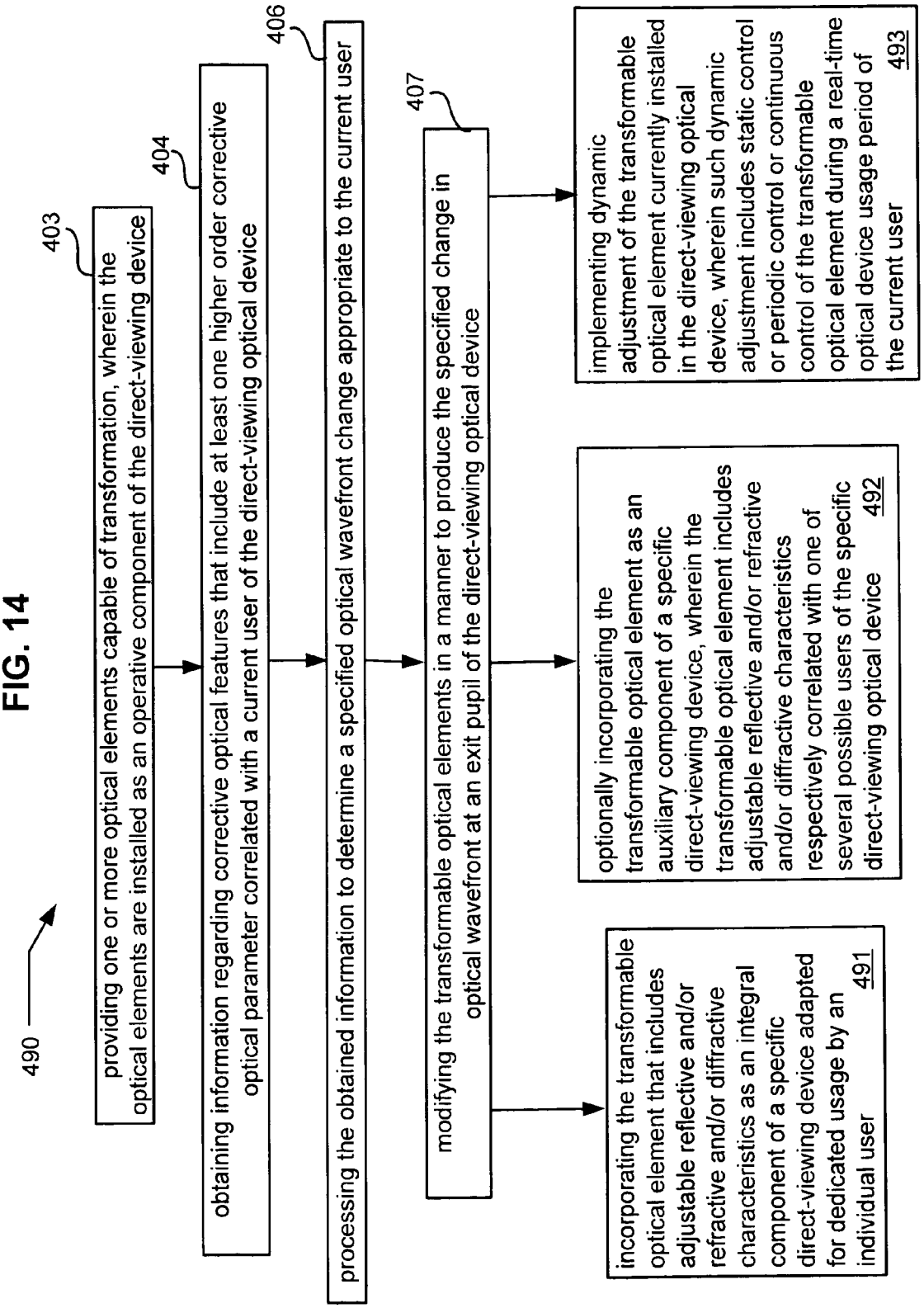

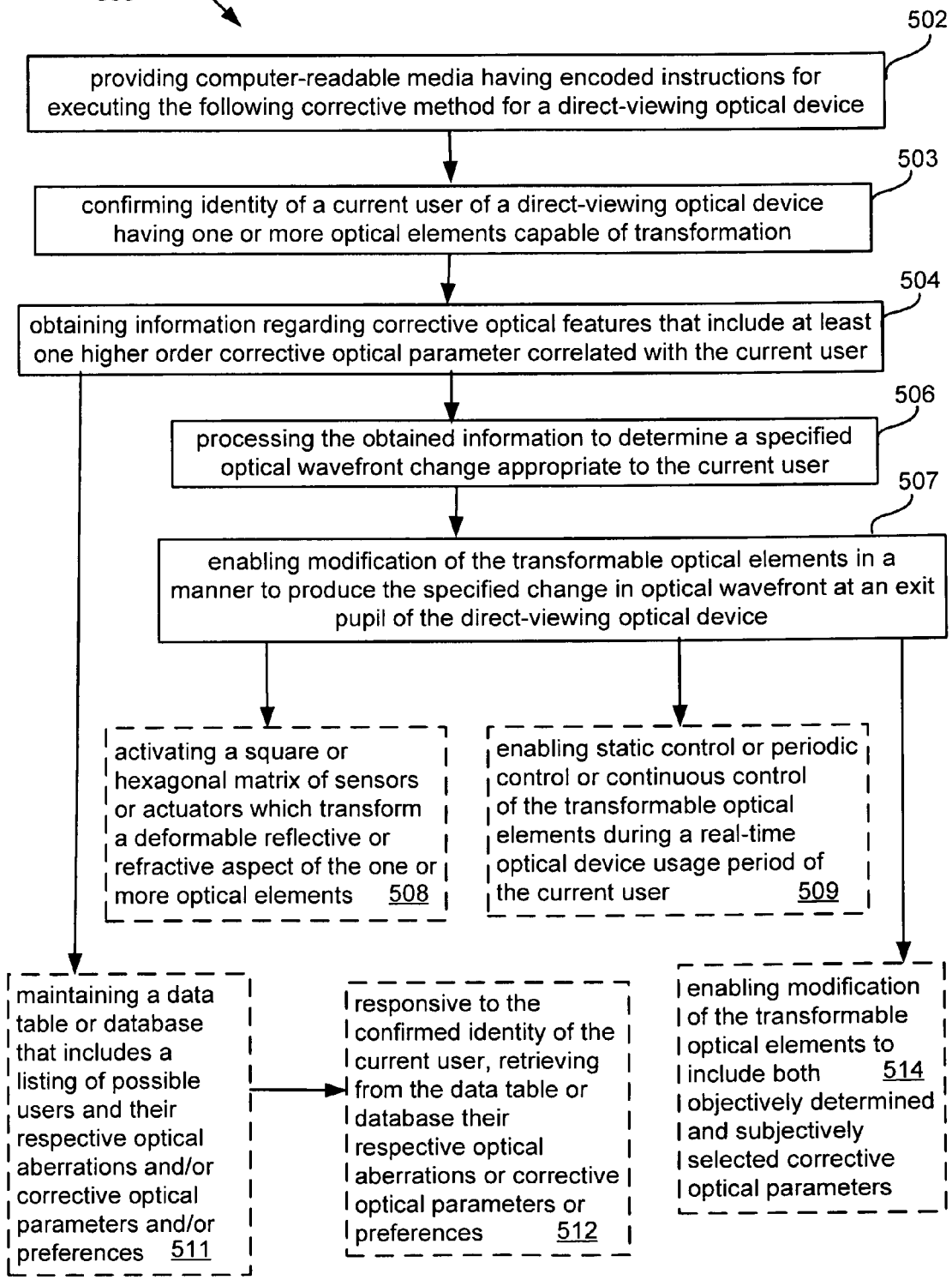

FIG. 16

| PERFORMANCE VIEWING FACTOR 610 | DEVICE XX USER BILL 615 | DEVICE YY USER BILL 620 | DEVICE XX USER ANN 625 | DEVICE YY USER EVA 630 | DEVICE ZZ USER EVA 635 |
|---|---|---|---|---|---|
| FIELD OF VIEW 612 | | | | | N/A 646 |
| BRIGHTNESS 614 | N/A 642 | | | | |
| IDENTIFIED TARGET OBJECT 616 | | | N/A 644 | | |
| SCENE CONTRAST 618 | | | | | |
| SPATIAL FREQUENCY CONTENT 622 | | | | | |
| SPECTRAL ATTRIBUTES 624 | | | | | N/A 647 |
| FOCAL LENGTH OF OPTICAL DEVICE 626 | | | | | |
| APERTURE STOP 628 | | N/A 648 | | | |
| USER'S PUPIL DIAMETER 632 | | | | N/A 649 | |
| GENERIC DEFAULT 634 | | | | | |

DATA TABLE RECORDS 600

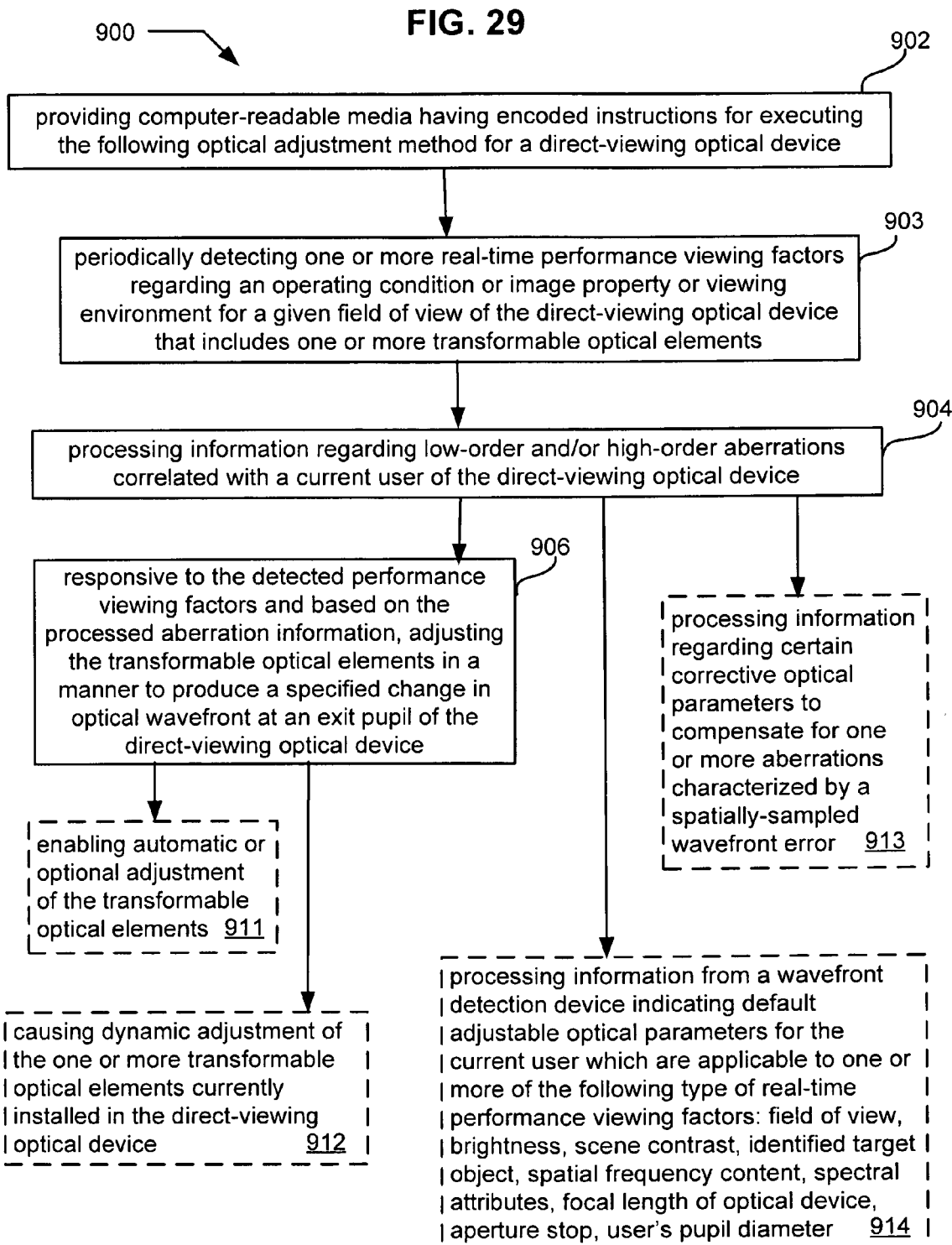

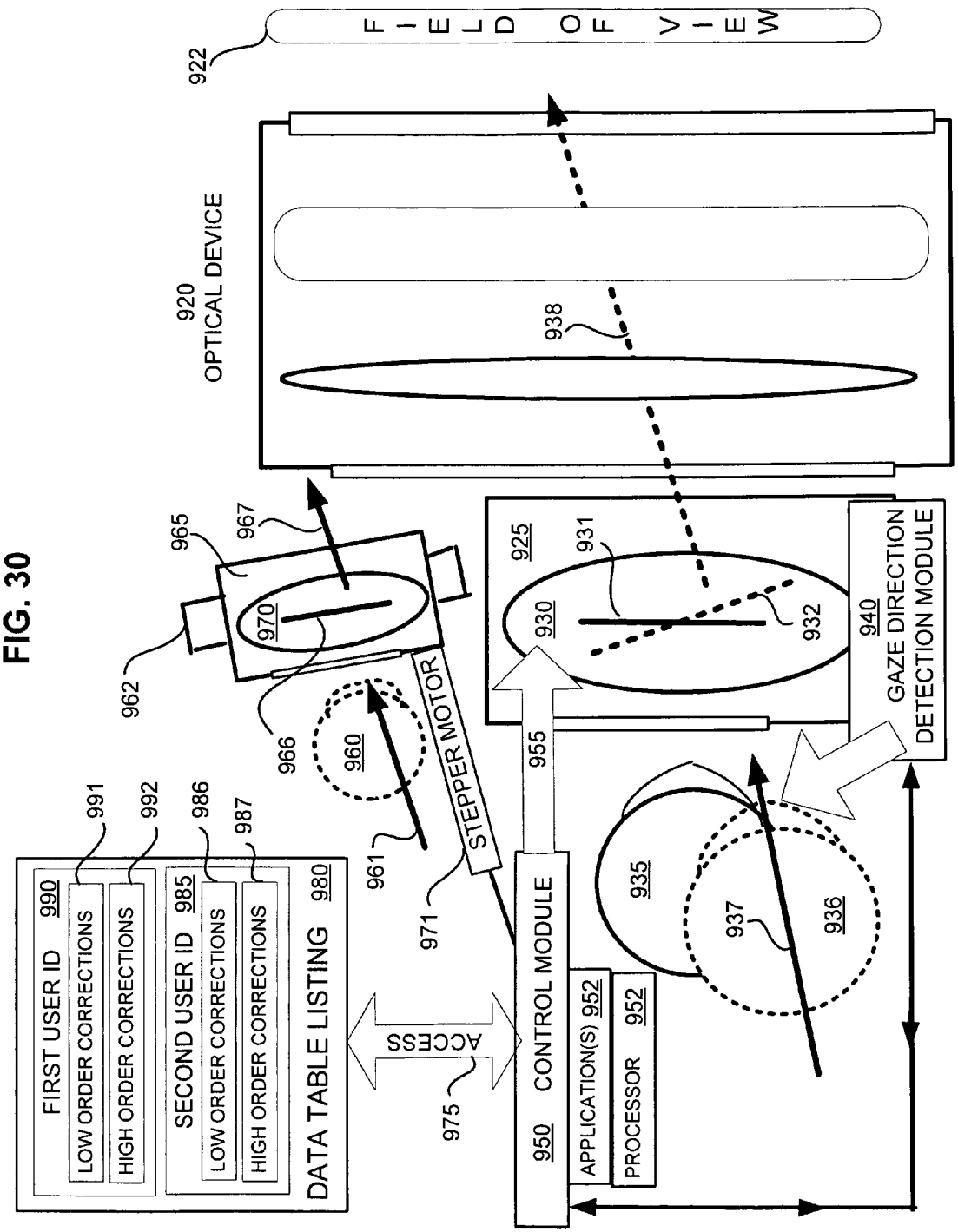

1012 — adopting an alignment adjustment method for a direct-viewing optical device 1013 — incorporating one or more corrective optical elements as an operative component in the direct-viewing optical device, wherein the corrective optical elements include customized optical parameters applicable to a particular user 1014 — tracking a gaze direction of a particular user of the direct-viewing optical device during a period of optical device usage 1016 — responsive to detection of the tracked gaze direction, activating a control module to reposition or transform the corrective optical elements in a manner to produce a specified change in optical wavefront at an exit pupil of the direct-viewing optical device, wherein the specified change enhances optical acuity during varied gaze directions 1026 — implementing a second operational mode causing dynamic adjustment of one or more transformable corrective optical elements currently installed in the direct-viewing optical device, in response to a detected shift of the tracked gaze direction 1021 — implementing a first operational mode causing physical repositioning of certain corrective optical elements in response to a detected shift of the tracked gaze direction 1022 — activating a motorized component to cause translational and/or rotational physical realignment of certain corrective optical elements relative to the tracked gaze direction of the particular user 1023 — enabling a user-activated component to cause translational and/or rotational physical realignment of certain corrective optical elements relative to the tracked gaze direction of the particular user 1024 — enabling a physical realignment to cause a central viewing axis of certain corrective optical elements to be substantially parallel with the tracked gaze direction of the particular user

FIG. 40

DATA RECORDS FOR PREDETERMINED CORRECTIVE PARAMETERS

| 1200 USER ID | 1230 APPROVED DEVICE LIST | 1240 DEFAULT SETTING FOR BOTH EYES | 1250 LEFT EYE LOW-ORDER | 1260 RIGHT EYE LOW-ORDER | 1270 LEFT EYE HIGH-ORDER | 1280 RIGHT EYE HIGH-ORDER |
|---|---|---|---|---|---|---|
| KIM 1202 | ✶ 1235a | | | | | |
| RON 1204 | ✶ 1235b | | | | N/A 1275 | N/A 1285 |
| LES 1206 | ✶ 1235c | | N/A 1255 | N/A 1265 | | |
| SID 1208 | LAB ONLY 1236 | | | | | |
| MARGE 1209 | | YES 1245 | | | | |
| LINDA 1212 | ✶ 1235d | | N/A 1256 | | | |
| GARY 1214 | ✶ 1235e | | | | N/A 1276 | |
| CHRIS 1216 | MICRO-SCOPE 1237 | NO 1246 | | | | |
| JAN 1218 | FIELD DEVICES 1238 | | | | | |
| MORT 1219 | | YES 1247 | | | | |

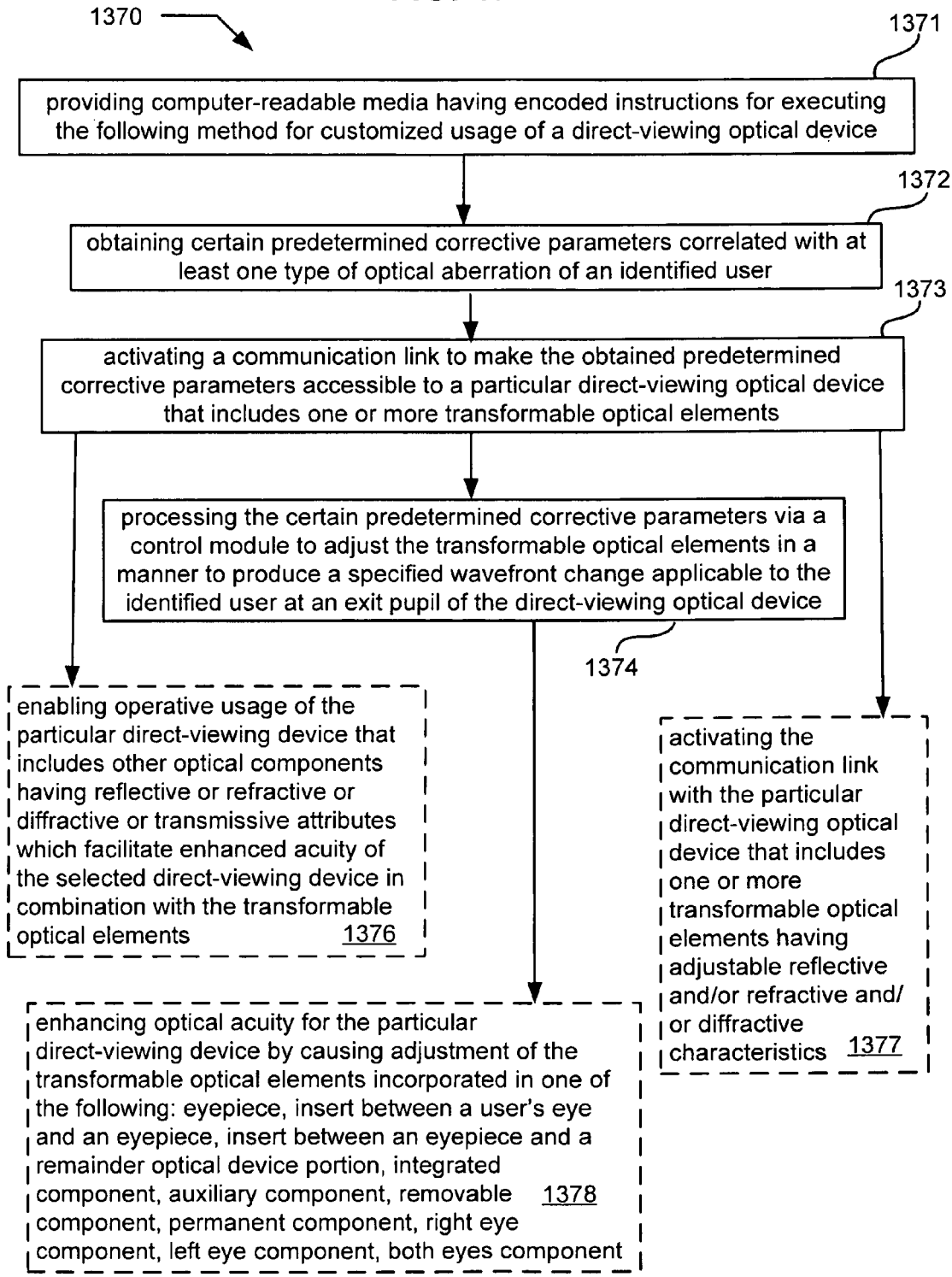

FIG. 48

DATA RECORDS FOR PREFABRICATED CORRECTIVE OPTICAL ELEMENTS 1400

| 1400 USER IDENTITY | 1430 DISPOSABLE | 1440 TRANS-FORMABLE & RE/W | 1450 RECYCLE | 1460 HIGH ORDER ONLY | 1470 BOTH LOW & HIGH ORDER | 1480 ONLY ONE DEVICE TYPE OR MODEL | 1490 MULTIPLE ACCEPTABLE DEVICES |
|---|---|---|---|---|---|---|---|
| JOHN # 00  1402 | | | YES 1452 | | YES 1472 | | YES 1491 ☆ 1492 |
| JOHN # 11  1404 | | YES 1442 | | YES 1462 | | YES 1481 △ | 1482 |
| JOHN # 22  1406 | | | YES 1454 | | YES 1474 | YES 1484 △ | |
| JOSH  1408 | | | YES 1456 | | YES 1476 | | YES 1493 ☆ |
| KARL # 00  1409 | | YES 1444 | | | YES 1477 | | YES 1494 ☆ |
| KARL # 11  1412 | | | YES 1458 | YES 1464 | | YES 1486 △ | |
| ANA # 00  1414 | | | YES 1459 | YES 1465 | | YES 1488 △ | |
| ANA # 11  1416 | YES 1432 | | | YES 1466 | YES 1478 | | YES 1496 ☆ |
| MIRA  1418 | | YES 1446 | | | | | YES 1497 ☆ |
| VISITOR  1419 | YES 1434 | | | | YES 1479 | | YES 1498 ☆ |

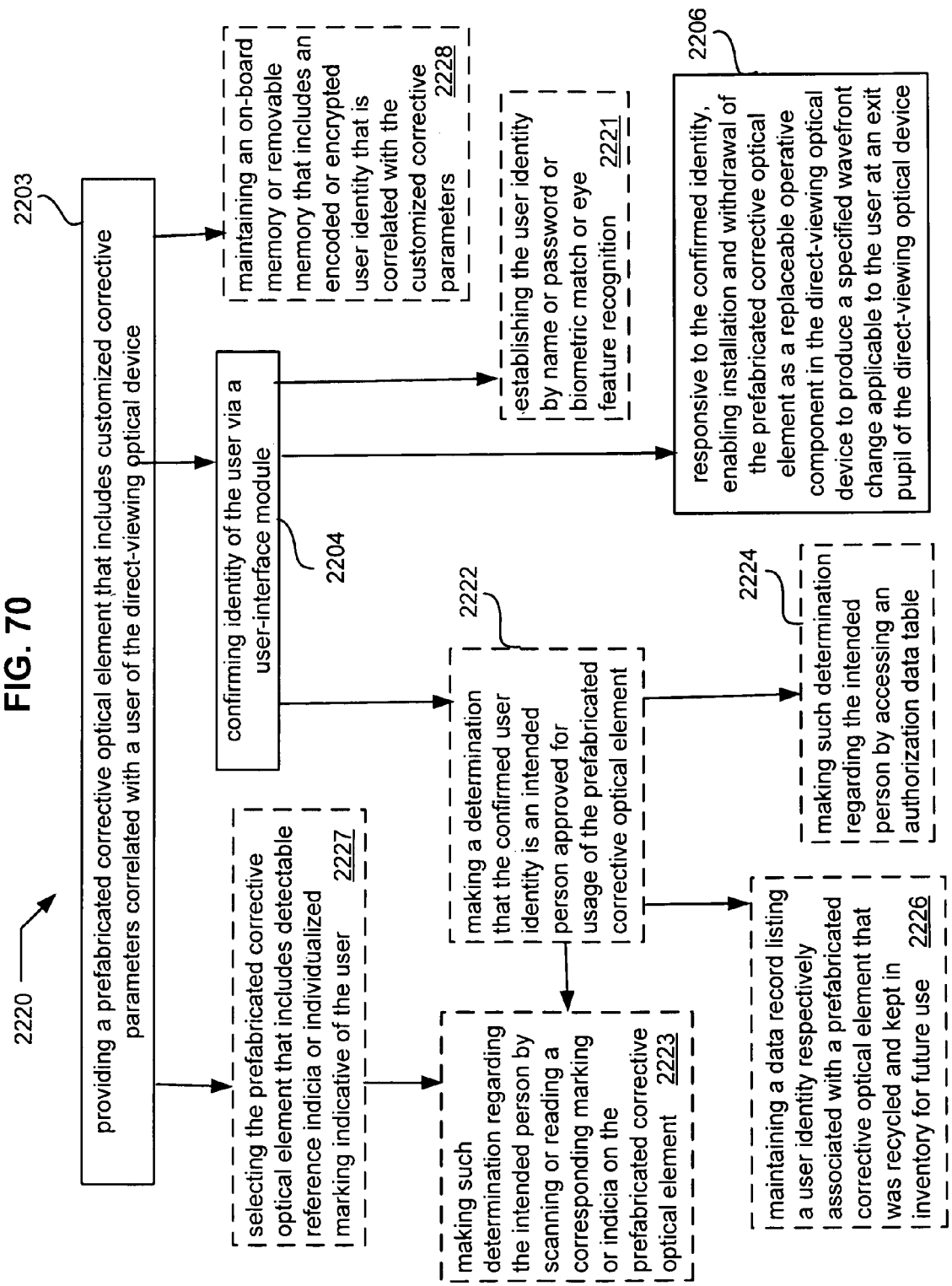

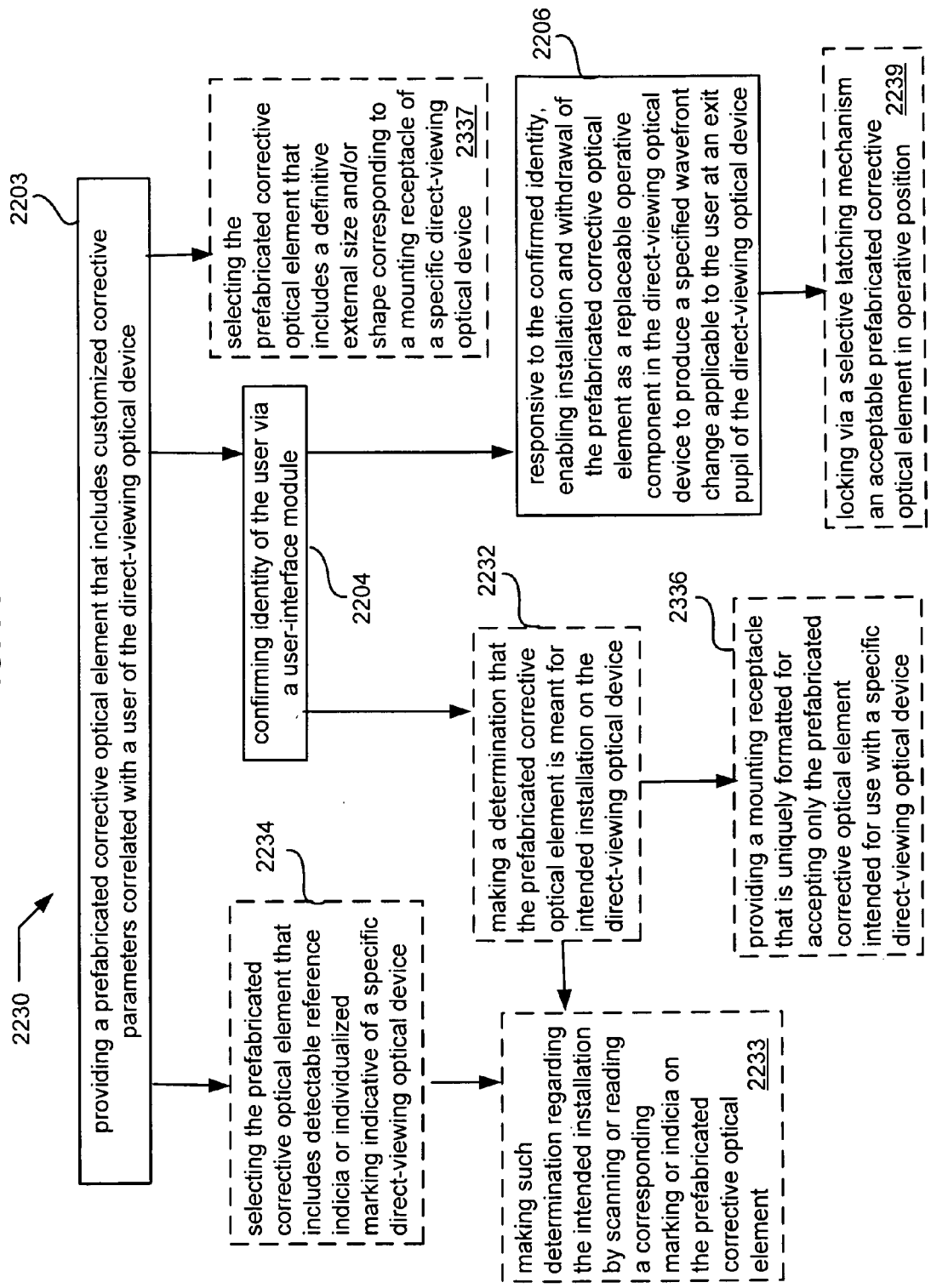

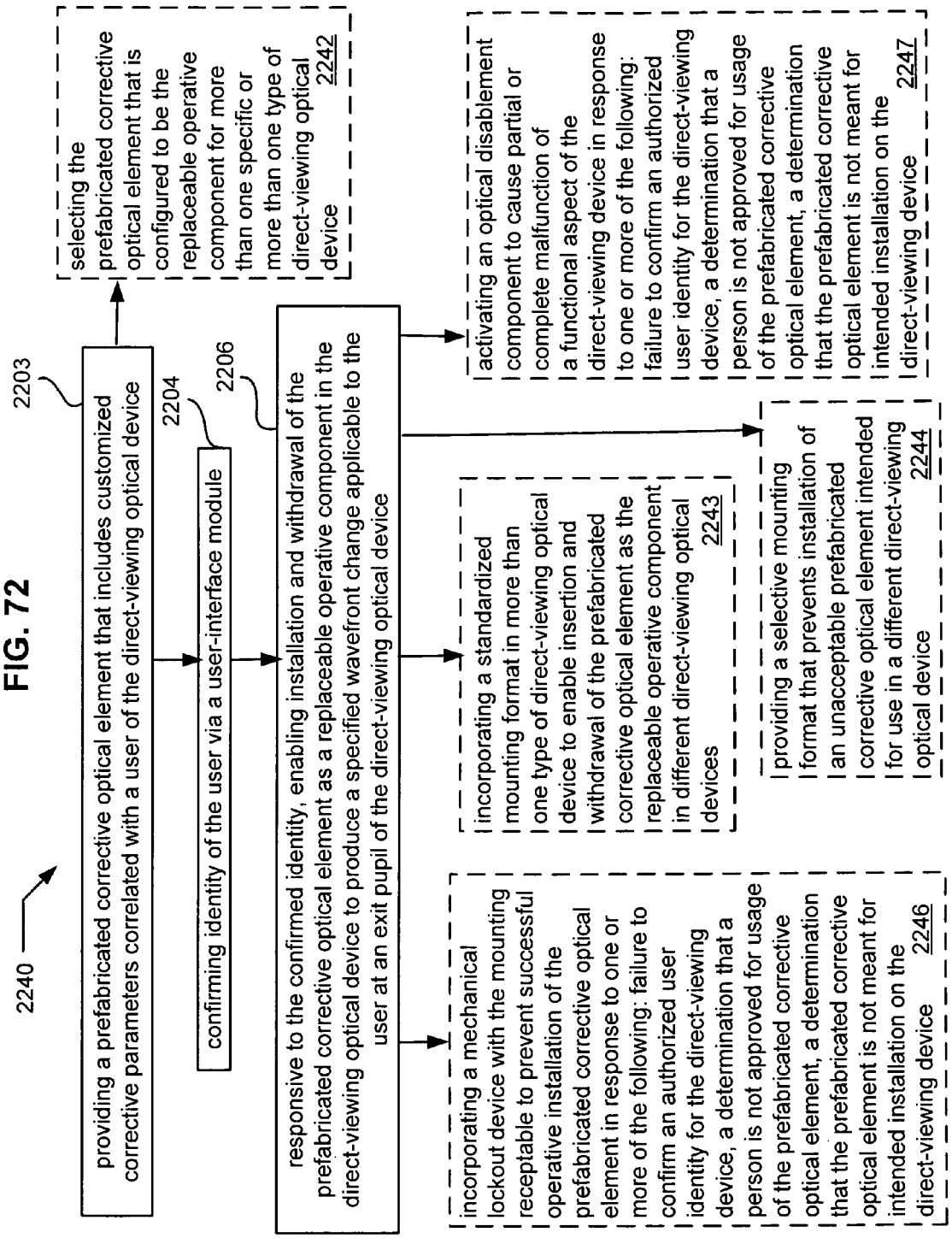

OPTICAL DEVICE WITH INTERCHANGEABLE CORRECTIVE ELEMENTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/385,688, entitled FABRICATION TECHNIQUE FOR REPLACEABLE OPTICAL CORRECTIVE ELEMENTS, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Feb. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/385,689, entitled CUSTOMIZED USER OPTIONS FOR OPTICAL DEVICE, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Feb. 2012, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,533 entitled OPTICAL DEVICE WITH ACTIVE USER-BASED ABERRATION CORRECTION, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Dec. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,520 entitled ADJUSTABLE OPTICS FOR ONGOING VIEWING CORRECTION, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Dec. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/374,517 entitled CORRECTIVE ALIGNMENT OPTICS FOR OPTICAL DEVICE, naming Kenneth G. Caldeira, Peter L. Hagelstein, Roderick A. Hyde, Edward K. Y. Jung, Jordin T. Kare, Nathan P. Myhrvold, John Brian Pendry, David Schurig, Clarence T. Tegreene, Charles Whitmer, Lowell L. Wood, Jr. as inventors, filed 29 Dec. 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

BACKGROUND

The present application relates to methods, devices, apparatus and systems regarding corrective optical components adapted for use with a direct-viewing optical device.

SUMMARY

In one aspect, an exemplary method for customized replacement of optical elements in a direct-viewing optical device may include providing a prefabricated corrective optical element that includes customized corrective parameters correlated with a user of the direct-viewing optical device; confirming identity of the user via a user-interface module; and responsive to the confirmed identity, enabling installation and withdrawal of the prefabricated corrective optical element as a replaceable operative component in the direct-viewing optical device to produce a specified wavefront change applicable to the user at an exit pupil of the direct-viewing optical device.

In one or more various aspects, related systems and apparatus include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In another aspect, an exemplary system includes but is not limited to computerized components regarding corrective optical elements and/or direct-viewing optical devices, which system has the capability to implement the various process features disclosed herein. Examples of various system and apparatus aspects are described in the claims, drawings, and text forming a part of the present disclosure.

Some exemplary customized replacement systems for optical elements in a direct-viewing optical device may include a prefabricated corrective optical element that includes customized corrective parameters correlated with a user of the direct-viewing optical device, a user-interface module operably coupled with the direct-viewing optical device and configured to establish identity of the user, and a mounting receptacle included on the direct-viewing optical device and adapted to receive the prefabricated corrective optical element as a replaceable operative component to produce a specified wavefront change applicable to the user at an exit pupil of the direct-viewing optical device.

In a further aspect, a computer program product may include computer-readable media having encoded instructions for executing a method for customized replacement of optical elements in a direct-viewing optical device, wherein the method includes detecting identity of a user of a direct-viewing optical device capable of receiving a prefabricated corrective optical element that includes customized corrective parameters correlated with the user; and responsive to the confirmed identity, activating the direct-viewing optical device after confirmed installation of the prefabricated corrective optical element as a replaceable operative component in the direct-viewing optical device to produce a specified wavefront change applicable to the user at an exit pupil of the direct-viewing optical device.

In addition to the foregoing, various other method and/or system and/or program product aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 7-14 are detailed flow charts illustrating further exemplary method aspects for adjustable optical embodiments.

FIG. 15 is a diagrammatic flow chart for exemplary computer-readable media embodiment features.

FIG. 16 shows a representative data table regarding adjustable corrective aspects for given performance viewing factors.

FIG. 29 is a diagrammatic flow chart for further exemplary computer-readable media embodiment features.

FIG. 30 is a schematic block diagram illustrating adjustable optical enhancements based on tracked gaze directions of a current user of a direct-viewing optical device.

FIG. 31 is a high level flow chart showing exemplary method aspects regarding optical alignment corrections for a direct-viewing optical device.

FIG. 40 shows representative data table records regarding predetermined optical corrective parameters.

FIGS. 42-47 are detailed flow charts illustrating additional exemplary method aspects regarding customized adjustment of transformable optical elements.

FIG. 48 shows representative data records regarding prefabricated corrective optical elements capable of replacement in a direct-viewing optical device.

FIGS. 70-72 are detailed flow charts illustrating further possible method aspects regarding interchangeable corrective optical elements for a direct-viewing optical device.

DETAILED DESCRIPTION

Figure 1:
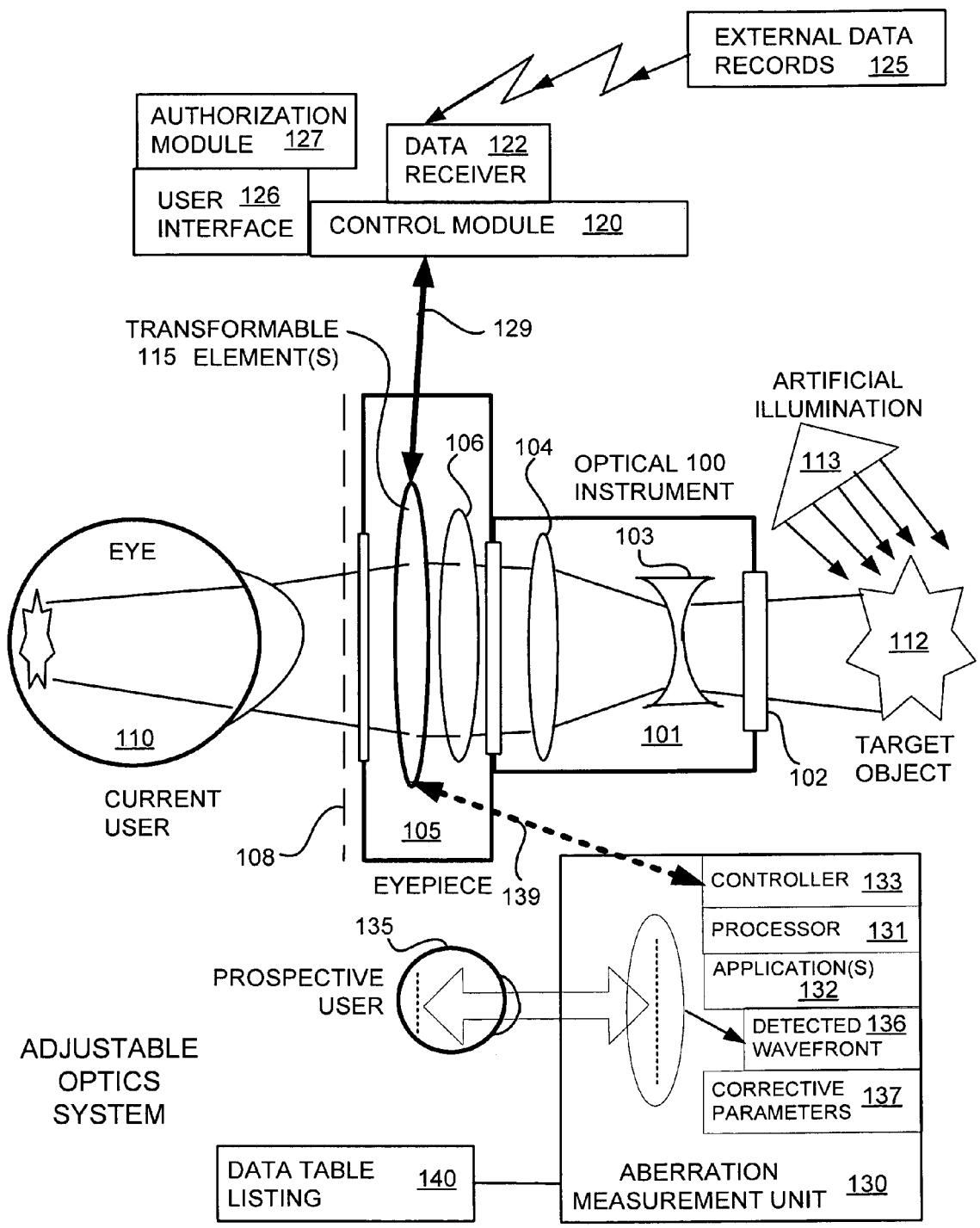
FIG. 1 is a schematic block diagram illustrating exemplary embodiment features for adjustable optics incorporated in a direct-viewing optical device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences.

In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

FIG. 1 is a schematic block diagram illustrating a direct-viewing optical device such as optical instrument 100 having a customized eyepiece 105 configured with one or more transformable optical elements 115 to enhance viewing acuity for an eye 110 of a current user. Other optical elements may also be incorporated with the optical instrument 100 to achieve a desired clear field of view of a target object 112 under various lighting conditions such as artificial illumination 113. Examples of such other optical elements are shown symbolically in the eyepiece 105 (e.g., see refractive lens 106) and also in an optical instrument body 101 (e.g., see aperture 102, diffractive lens 103, refractive lens 104) to provide operative visual coupling with the transformable optical elements 115. In some instances the transformable optical elements 115 may include an element having variable chromatic aberration properties, and/or other aberration properties.

A control module 120 may be connected via a communication link (e.g., see electrical link 129) to the transformable optical elements 115 and provides customized adjustment in accordance with optical corrective parameters associated with the current user. In that regard such optical corrective parameters and/or their respective user aberrations may be accessible via a data receiver 122 from external data records 125 for processing by the control module 120 in a manner to achieve an optimum optical wavefront at an exit pupil (see representation of approximate exit plane 108) of the optical instrument 100.

A user interface 126 together with authorization module 127 are adapted to recognize identity of the current user. The control module 120 includes circuitry and/or software that is configured to cause the transformable optical elements 115 to be adjusted based on appropriate optical corrective parameters associated with the current user.

In some system embodiments an aberration measurement unit 130 may be available for monitoring an eye 135 of a prospective user in order to obtain a new or updated data record regarding detected wavefront 136. The aberration measurement unit 130 may include processor 131, one or more applications 132, as well as controller 133 and light source (not shown) to obtain and process the newly acquired wavefront data as well as in some instances determine appropriate corrective parameters 137 for the prospective user. An optional communication link 139 may provide a direct connection between controller 133 and the transformable optical elements 115 for enabling customized adjustment during a time of usage of the optical instrument 100 by the prospective user. Some implementations may include a data table listing 140 linked with the aberration measurement unit for maintaining user preferences, previously determined wavefront data, and default corrective parameters related to different specific optical instruments or types of optical instruments.

It will be understood that the particular additional optical elements disclosed herein are for purposes of illustration only, and are intended to represent various combinations of optical elements that can be chosen and situated in a direct-viewing optical device in a manner to provide operative visual coupling with the transformable optical elements shown in FIGS. 1-5.

Figure 2:
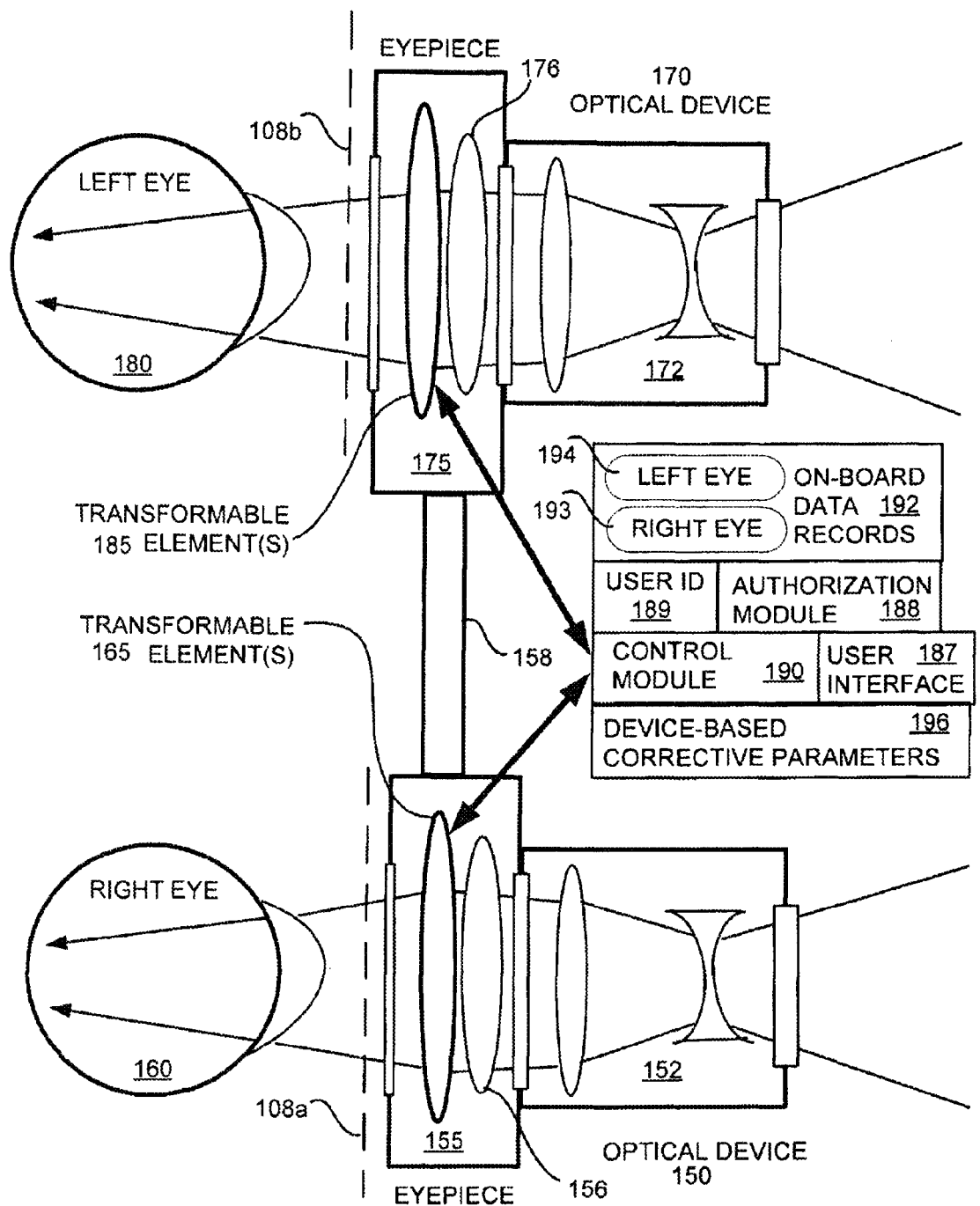
FIG. 2 is a schematic block diagram illustrating exemplary features for another adjustable optics embodiment.

FIG. 2 is schematic block diagram illustrating a composite direct-viewing optical device that includes two optical device portions 150, 170. Optical device portion 150 includes a customized eyepiece 160 configured with one or more transformable optical elements 165 to enhance viewing acuity for a right eye 160 of a current user. Additional optical elements may also be incorporated with the customized eyepiece 160 (e.g., see refractive element 156) and may be included as part of an optical body portion 152 (e.g., reflective, refractive, diffractive, transmissive elements) to achieve a desired clear field of view of under various viewing conditions.

Optical device portion 170 includes a customized eyepiece 175 configured with one or more transformable optical elements 185 to enhance viewing acuity for a left eye 180 of a current user. It will be understood that some aberrations and related corrective parameters may be respectively different for a right eye 160 and for a left eye 180 of an identified user (see on-board data records 192). In other instances the same corrective parameters may be correlated with both eyes of a current user, depending on the circumstances.

Additional optical elements may also be incorporated with the optical device portion 170 to achieve a desired clear field of view under various viewing conditions. Examples of such other optical elements are shown symbolically in the customized eyepiece 175 (e.g., see refractive lens 176) and may be included in an optical instrument body 172 (e.g., reflective, refractive, diffractive, transmissive elements), and are configured in a manner to provide operative visual coupling with the transformable optical elements 185.

An exemplary system embodiment shown in FIG. 2 may include control module 190 having user interface 187, and on-board data records 192 that include right eye 193 and left eye 194 wavefront aberrations, user preferences, and other user-related information. The control module 190 is operatively linked to both sets of transformable elements 165, 185 in order to make dynamic adjustment applicable to each eye of a current optical device user who is recognized by authorization module 188 and matched with their user ID 189. Additional records may include device-based corrective parameters 196 that ameliorate optical defects of a specific direct-viewing optical device. It will be understood that control module 190 includes circuitry and/or software configured in a manner to achieve an optimum optical wavefront for a particular user at an exit pupil (see representation of approximate exit planes 108a, 108b) of the composite direct-viewing device depicted in FIG. 2.

Figure 3:
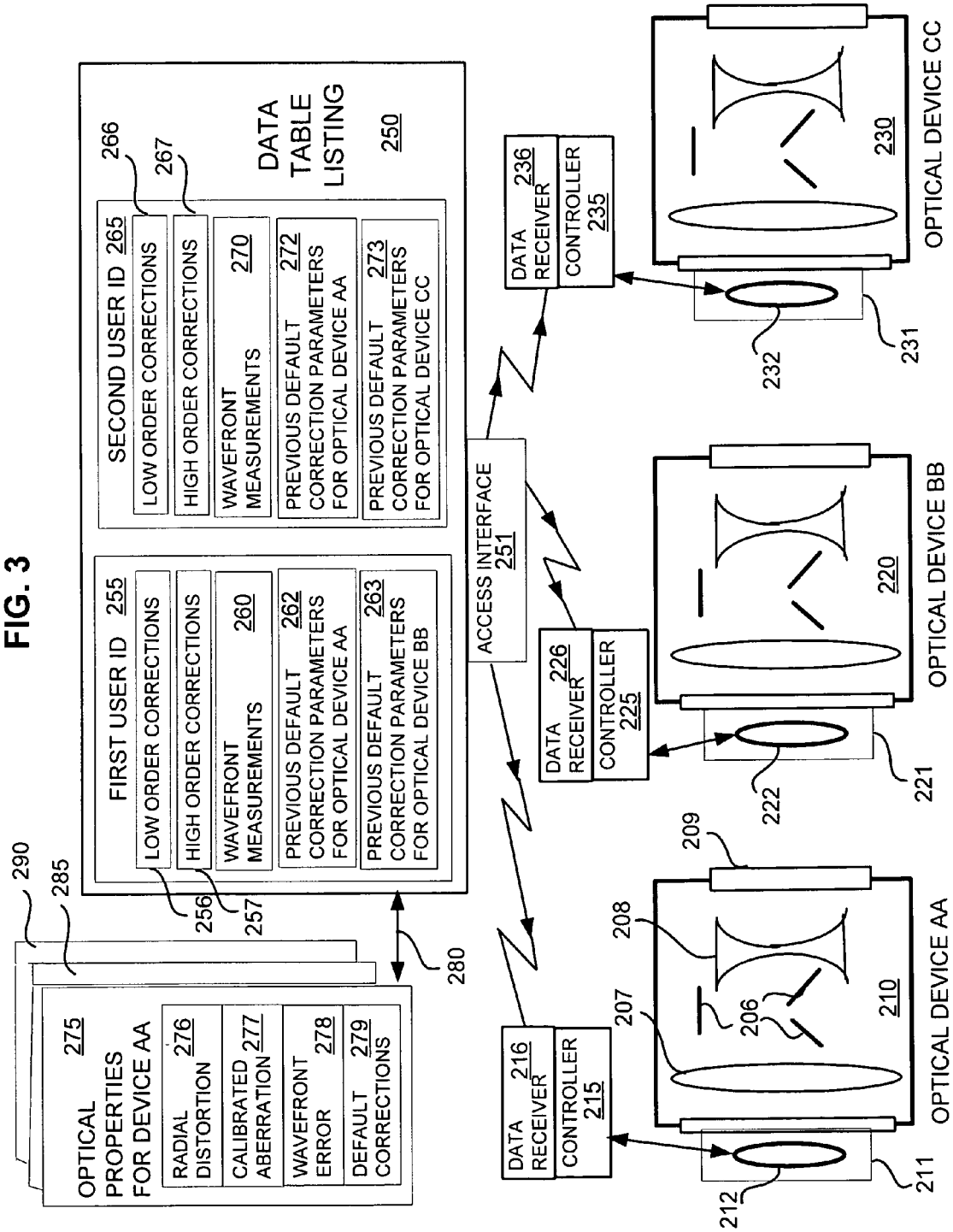
FIG. 3 is a schematic block diagram illustrating corrective optical data records that are accessible to several direct-viewing optical devices.

Referring to the schematic block diagram of FIG. 3, a possible system embodiment may include a data table listing 250 maintained for multiple approved users indicated by a first user identity 255, and a second user identity 265, inter alia. In some instances the data table listing may also provide user-related optical preferences respectively applicable to different direct-viewing optical devices 210, 220, 230.

For example, known informational data correlated with first user ID 255 may include low order corrections 256, high order corrections 257, wavefront measurements 260, and previous default corrective parameters 262 respectively for optical device AA (see 210), and previous default parameters 263 respectively for optical device BB (see 220). As another example, known informational data correlated with the second user ID 265 may include low order corrections 266, high order corrections 267, wavefront measurements 170, previous default corrective parameters 272 respectively for optical device AA (see 210), and previous default corrective parameters 273 respectively for optical device CC (see 230).

An additional data table record may be maintained regarding known optical properties for device AA (see 275), a further data table regarding known optical properties for device BB (see 285), and another data table regarding known optical properties for device CC (see 290). Such data table records may respectively indicate for each optical device AA, BB, CC various pertinent inherent optical properties such as radial distortion 276, calibrated aberration 277, wavefront error 278, and default corrections 279.

It will be understood that the informational data shown in the data tables and data records of FIG. 3 are for purposes of illustration only, and may be expanded or altered in some embodiments and may be shortened or omitted in other embodiments depending on the circumstances.

A communication link 280 may be provided between data table listing 250 and data table records 275, 285, 290 to assure data retrieval and/or data entry via an access interface 251. In that regard an exemplary embodiment includes a wired or wireless operative connection between the access interface 251 and data receiver 216 for optical device 210, and between the access interface 251 and data receiver 226 for optical device 220, and between the access interface 251 and data receiver 236 for optical device 230. It will be understood that different users may be actively engaged with their respectively located and uniquely adjusted direct-viewing devices during a same period of time. Also a single user may use specifically different direct-viewing optical devices during sequential periods of time while enjoying real-time customized optical corrective parameters associated with their previously known or currently updated wavefront aberrations.

A controller 215 may include circuitry and/or software for processing information received by data receiver 216 as a basis for customized real-time optical adjustment of transformable optical element 212 incorporated with eyepiece 211 of optical device 210. Such optical adjustment is correlated with a current user's corrective parameters, and may occur automatically or optionally in accordance with a current user's preference. As previously indicated, a body of the optical device 210 may provide additional optical elements that include reflective 206, refractive 207, diffractive 208, and/or transmissive 209 characteristics to achieve enhanced acuity for a current user.

Similarly a controller 225 may include circuitry and/or software for processing information received by data receiver 226 as a basis for customized real-time optical adjustment of transformable optical element 222 incorporated with eyepiece 221 of optical device 220. Such optical adjustment is correlated with a current user's corrective parameters, and may occur automatically or optionally in accordance with indicated preferences of a current user.

Similarly a controller 235 may include circuitry and/or software for processing information received by data receiver 236 as a basis for customized real-time optical adjustment of transformable optical element 232 incorporated with eyepiece 231 of optical device 230. Such optical adjustment is correlated with a current user's corrective parameters, and may occur automatically or optionally in accordance with indicated preferences of a current user.

Figure 4:
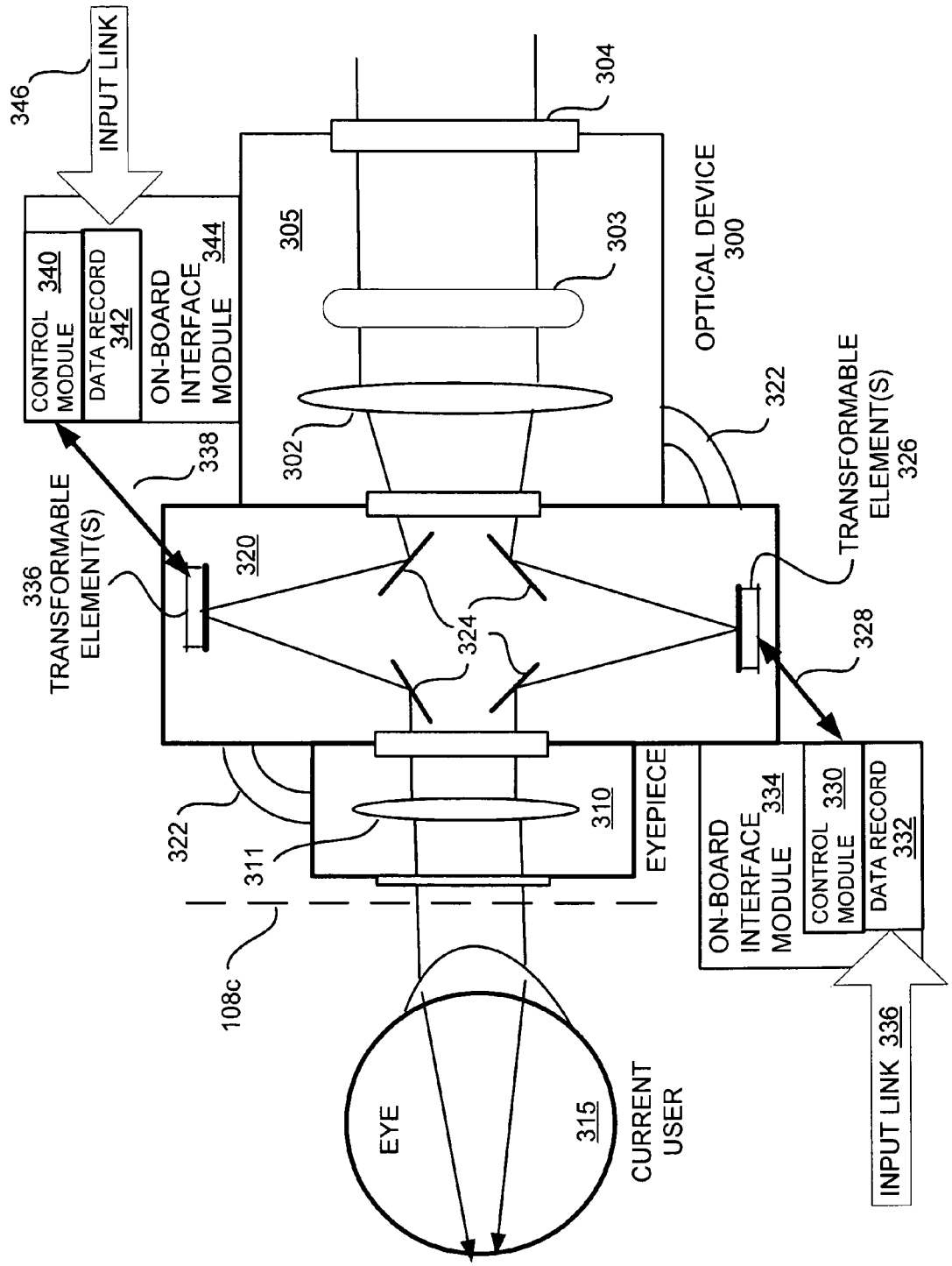
FIGS. 4-5 are schematic block diagrams illustrating additional examples of adjustable optical embodiments.

FIG. 4 is a schematic block diagram illustrating a direct-viewing optical device 300 having an eyepiece 310 and body portion 305, with a customized optical component 320 mounted and secured by brackets 322 as an integral insert between the eyepiece 105 and body portion 305. In this embodiment the customized optical component 320 is configured to include one or more transformable optical elements (e.g., reflective elements 326, 336) to enhance viewing acuity for an eye 315 of a current user. Other optical elements may also be incorporated with the optical device 300 to achieve a desired clear field of view under various viewing conditions. Examples of such other optical elements are shown symbolically in the eyepiece 310 (e.g., see refractive lens 311) and body portion 305 (e.g., see aperture 304, transmissive filter 303, refractive lens 302), and also in the customized optical component 320 (e.g., see reflective elements 324) to provide operative visual coupling with the transformable optical elements 326, 336.

Control modules 330, 340 may be respectively connected via electrical links 328, 338 to the transformable optical elements 326, 336 for customized real-time adjustment based on low-order and/or high-order aberrations associated with the current user. In that regard, a first on-board interface module 334 may include certain optical corrective parameters in data record 332 for processing by control module 330, and a second on-board interface module 344 may include other optical corrective parameters in data record 342 for processing by control module 340, in a manner to achieve an optimum optical wavefront at an exit pupil (see representation of approximate exit plane 108*c*) of the optical instrument 300. Updated user aberration data as well as user preferences, etc. may be received via input link 336 to data record 322, as well as via input link 346 to data record 342.

Figure 5:
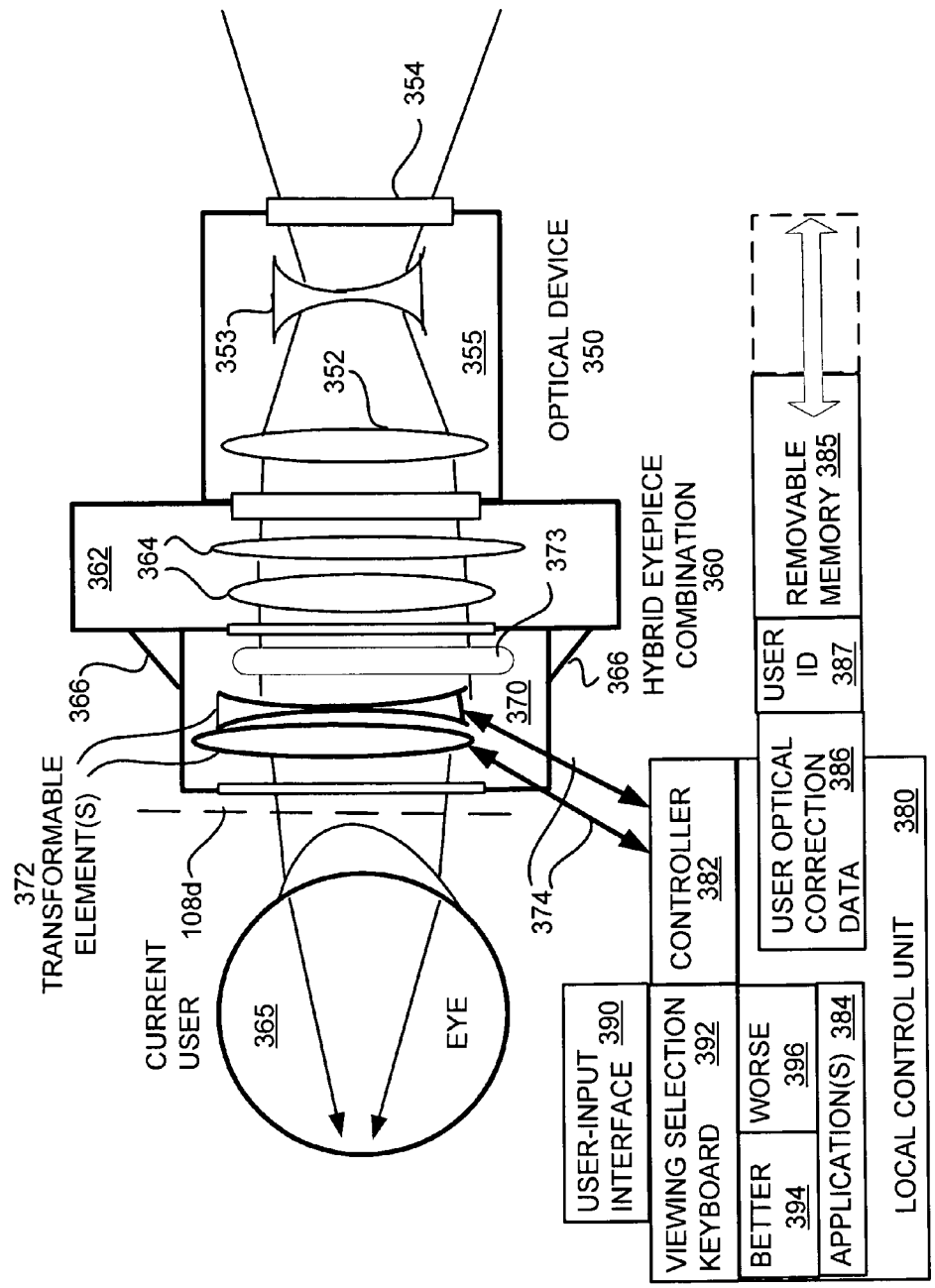

Referring to the schematic block diagram of FIG. 5, an exemplary embodiment may include a direct-viewing optical device 350 having a hybrid eyepiece combination 360 that includes a conventional eyepiece 362 with an auxiliary customized optical component 370 mountable adjacent a current user's eye 365 on adapter ring 366. This enables the auxiliary customized optical component 370 to be manually removable during a period of ordinary generic usage of the optical device 350, or optionally mounted between the conventional eyepiece 362 and a current user's eye 365 to enable dynamic adjustment of transformable elements 372 during a hyper-acuity usage period.

In this embodiment the auxiliary customized optical component 370 is configured to include one or more transformable optical elements (e.g., displaceable refractive/diffractive elements 372) to enhance viewing acuity for the eye 365 of a current user. Other optical elements may also be incorporated with the optical device 350 to achieve a desired clear field of view under various viewing conditions. Examples of such other optical elements are shown symbolically in the conventional eyepiece 362 (e.g., see different refractive elements 364) and body portion 355 (e.g., see aperture 354, diffractive lens 353, refractive lens 352), and also in the customized optical component 370 (e.g., see transmissive filter elements 373) to provide operative visual coupling with the transformable optical elements 372. Exemplary types of filter elements may include wide band, narrow band, ultra-violet (UV) blocking, polarizer, chromatic, etc. in order to optimize acuity for a current user of a particular direct-viewing optical device.

An exemplary local control unit 380 includes controller 382 and one or more program applications 384 for processing aberrational corrections correlated with the current user. In that regard, the local control unit 380 may be adapted to receive removable memory records 385 that include user optical correction data 386 along with a verifiable user ID 387. This enables the controller 382 to process such user optical correction data 386 and transmit appropriate control signals via electrical communication links 374 to the transformable elements 372 during a period of usage by the verified current user.

A further exemplary feature of local control unit 380 includes components for enabling subjective determination of optimal adjustment of the transformable elements 372. A user-input interface 390 is linked with a viewing selection keyboard 392 such that the current user can make data entries based on comparison between alternative adjustments of the transformable elements 372 for varied viewing conditions or different fields of view or selected target objects as seen through the hybrid eyepiece combination 385. The user's subjective determinations can be indicated as "better" 394 or "worse" 396 as a basis for real-time implementation by controller 362, and also can be maintained in a data record for future reference.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Figure 6:
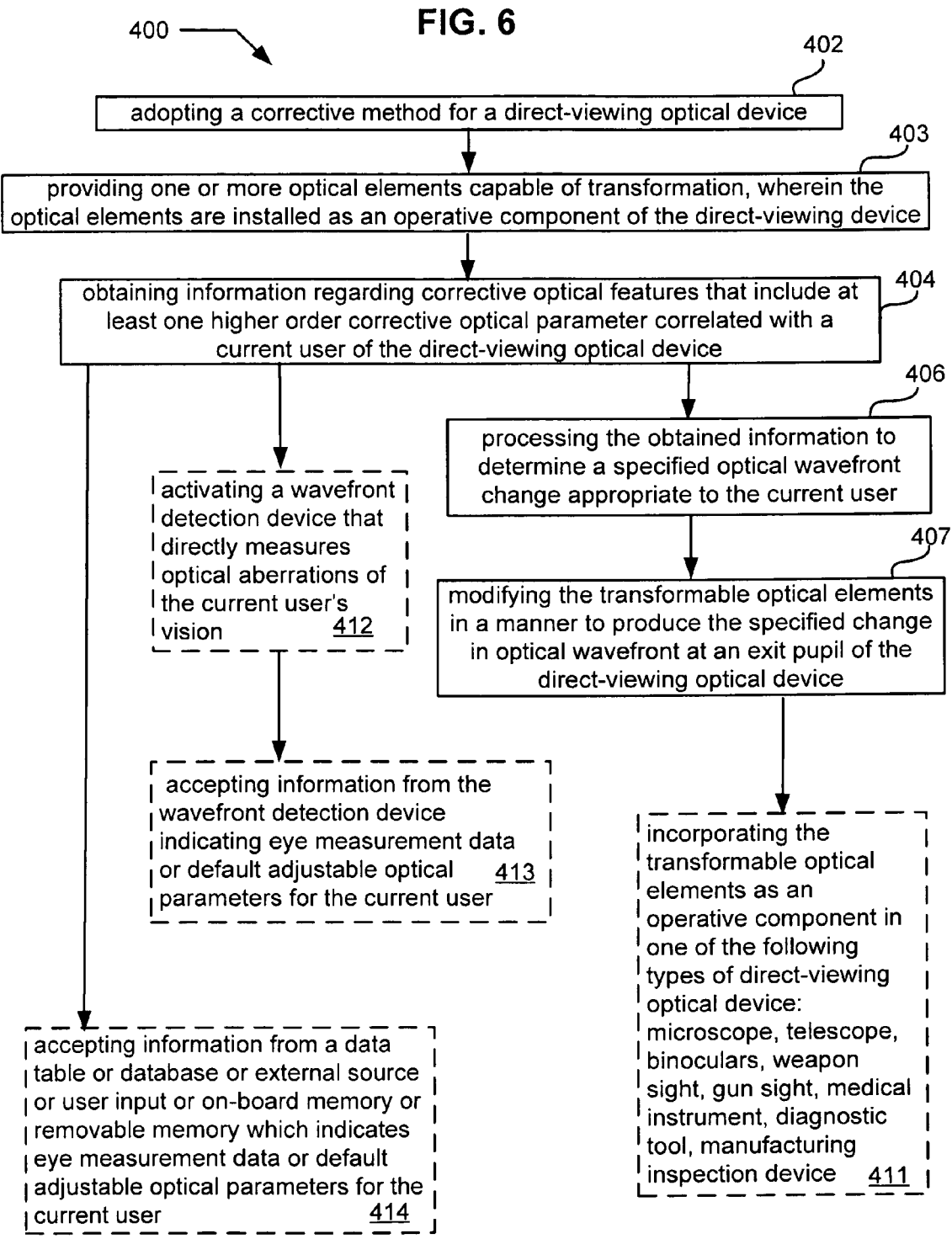
FIG. 6 is a high level flow chart that shows exemplary method aspects for providing enhanced acuity in a direct-viewing optical device.

Referring to embodiment features 400 shown in the high level flow chart of FIG. 6, an adopted corrective method for a direct-viewing optical device (see block 402) may include providing one or more optical elements capable of transformation, wherein the optical elements are installed as an operative component of the direct-viewing device (block 403); and obtaining information regarding corrective optical features that include at least one higher order corrective optical parameter correlated with a current user of the direct-viewing optical device (block 404). Related exemplary aspects include processing the obtained information to determine a specified optical wavefront change appropriate to the current user (block 406), and modifying the transformable optical elements in a manner to produce the specified change in optical wavefront at an exit pupil of the direct-viewing optical device (block 407).

In some instances further process exemplary features include incorporating the transformable optical elements as an operative component in one of the following types of direct-viewing optical device: microscope, telescope, binoculars, weapon sight, gun sight, medical instrument, diagnostic tool, manufacturing inspection device (block 411). Other process examples include activating a wavefront detection device that directly measures optical aberrations of the current user's vision (block 412), and accepting information from the wavefront detection device indicating eye measurement data or default adjustable optical parameters for the current user (block 413).

Further possible aspects shown in FIG. 6 include accepting information from a data table or database or external source or user input or on-board memory or removable memory which indicates eye measurement data or default adjustable optical parameters for the current user (block 414).

Figure 7:
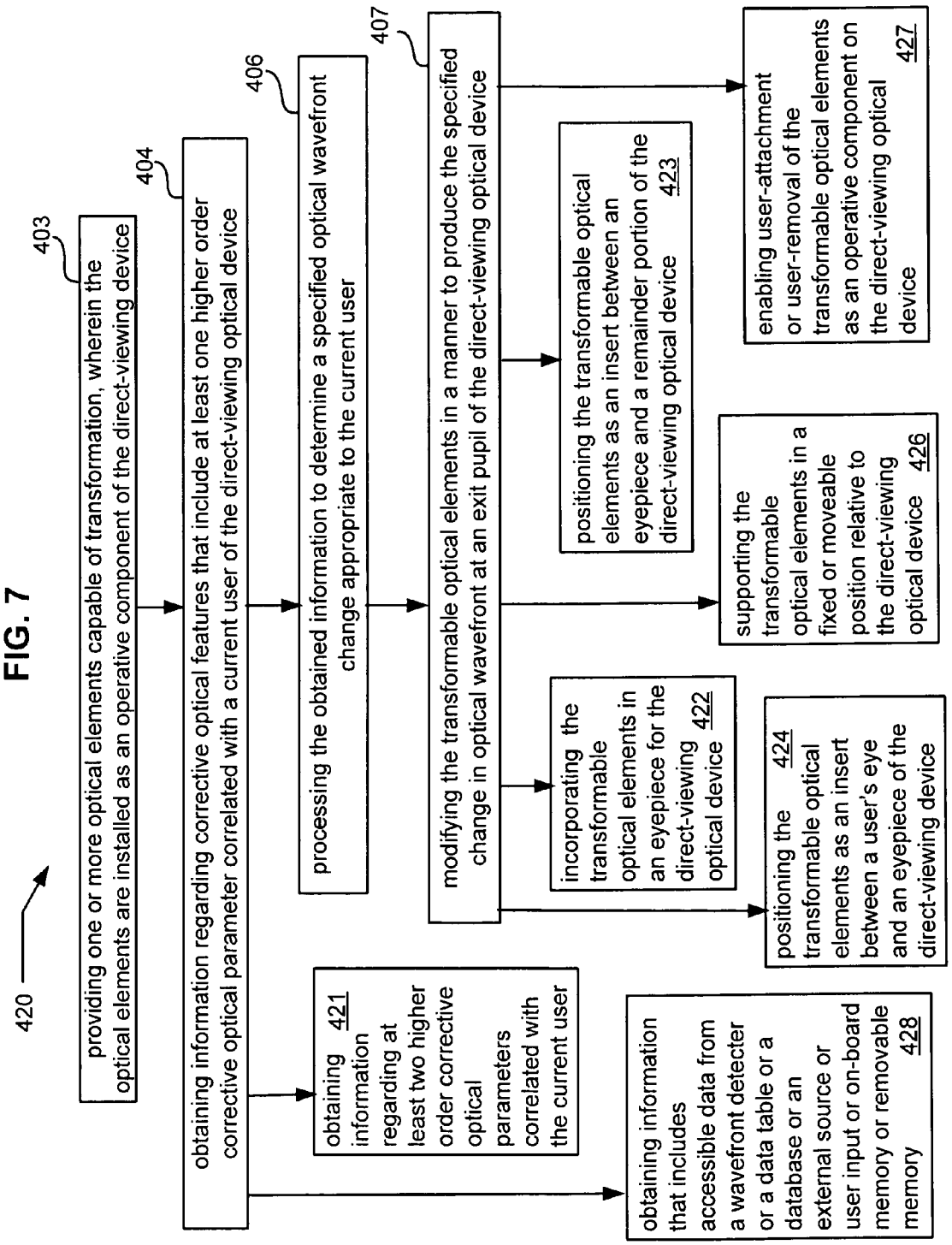

The flow chart of FIG. 7 illustrates further process embodiment features 420 that include previously described aspects 403, 404, 406, 407 in combination with obtaining information regarding at least two higher order corrective optical parameters correlated with the current user (block 421). A further process operation may include obtaining information that includes accessible data from a wavefront detector or a data table or a database or an external source or user input or on-board memory or removable memory (block 428).

Other exemplary process aspects include incorporating the transformable optical elements in an eyepiece for the direct-viewing optical device (block 422), and in some instances positioning the transformable optical elements as an insert between an eyepiece and a remainder portion of the direct-viewing optical device (block 423). Other possible process embodiments include positioning the transformable optical elements as an insert between a user's eye and an eyepiece of the direct-viewing device (block 424), as well as supporting the transformable optical elements in a fixed or moveable position relative to the direct-viewing optical device (block 426). Further possibilities include enabling user-attachment or user-removal of the transformable optical elements as an operative component on the direct-viewing optical device (block 427).

Figure 8:
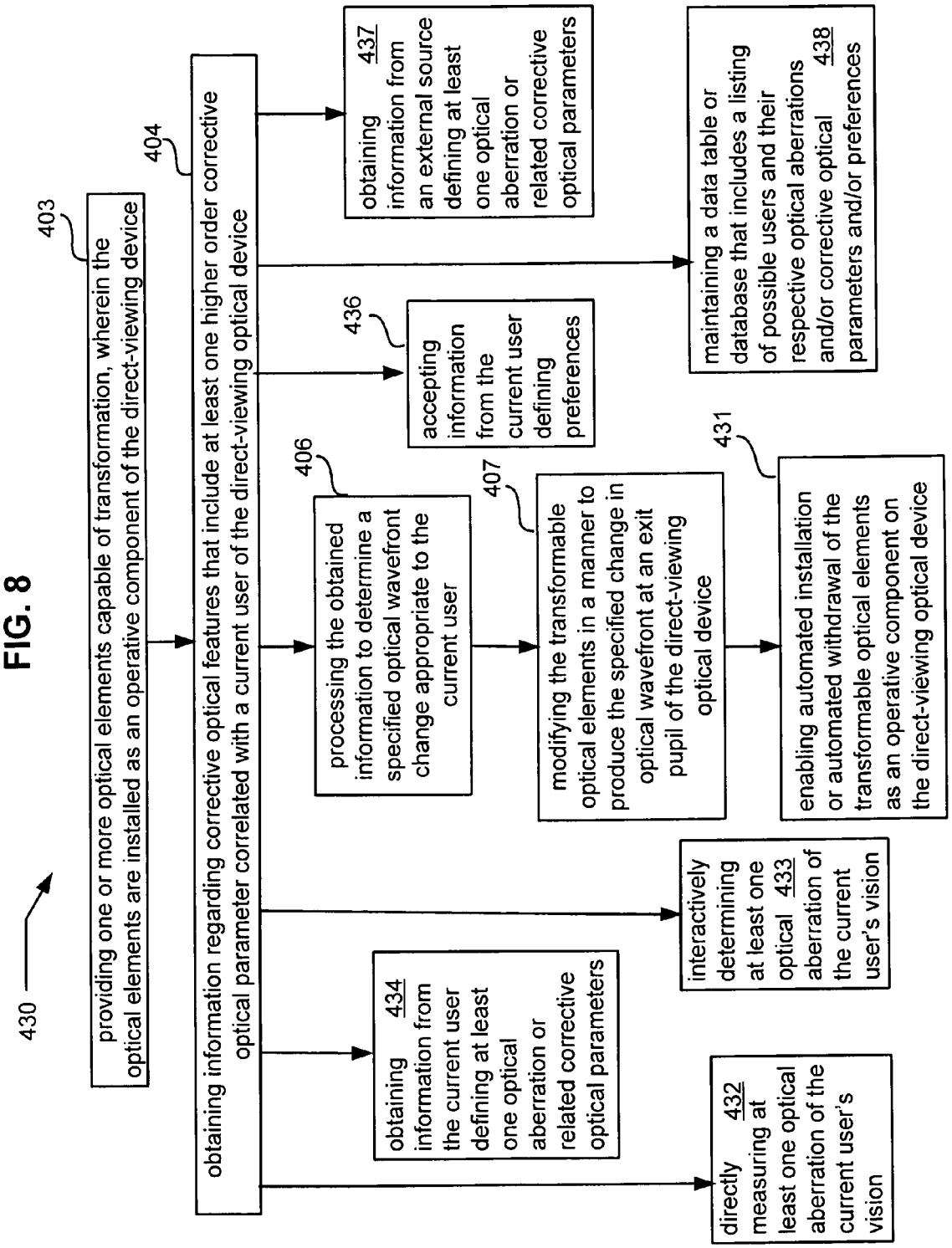

FIG. 8 shows various embodiment features 430 that include previously described aspects 403, 404, 406, 407 as well as enabling automated installation or automated withdrawal of the transformable optical elements as an operative component on the direct-viewing optical device (block 431). In some embodiments a further aspect includes directly measuring at least one optical aberration of the current user's vision (block 432). Other aspects may include interactively determining at least one optical aberration of the current user's vision (block 433), and obtaining information from the current user defining at least one optical aberration or related corrective optical parameters (block 434).

Further process enhancements may include accepting information from the current user defining preferences (block 436), and obtaining information from an external source defining at least one optical aberration or related corrective optical parameters (block 437). Additional exemplary aspects include maintaining a data table or database that includes a listing of possible users and their respective optical aberrations and/or corrective optical parameters and/or preferences (block 438).

Figure 9:
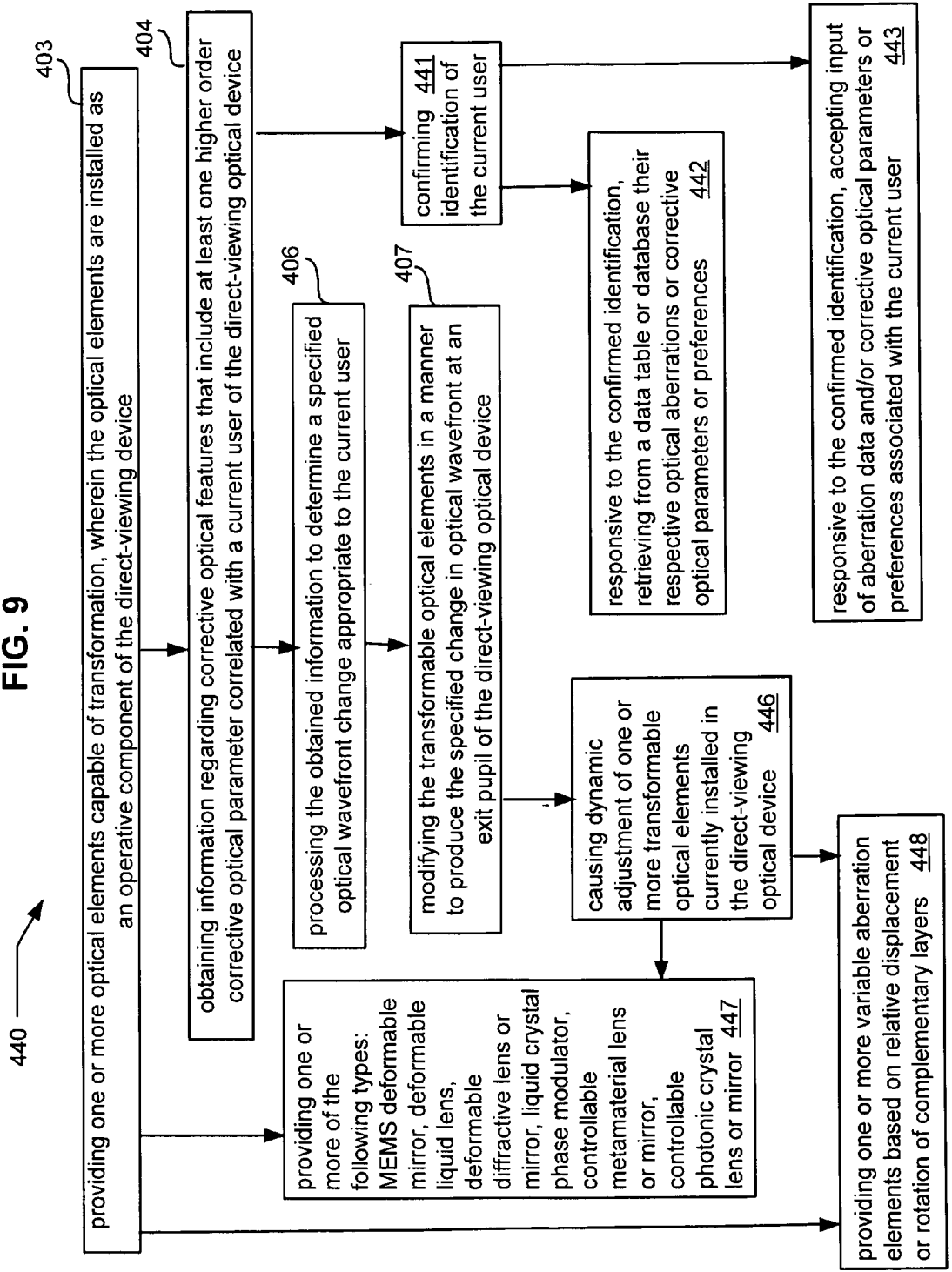

The detailed flow chart of FIG. 9 illustrates embodiment features 440 that include previously described process aspects 403, 404, 406, 407 in combination with confirming identification of the current user (block 441). An additional possible aspect responsive to the confirmed identification of the current user includes retrieving from a data table or database their respective optical aberrations or corrective optical parameters or preferences (block 443). A further possible aspect responsive to the confirmed identification of the current user includes accepting input of aberration data and/or corrective optical parameters or preferences associated with the current user (block 443).

Another illustrated process feature includes causing dynamic adjustment of one or more transformable optical elements currently installed in the direct-viewing optical device (block 446). Related exemplary features regarding the transformable optical elements include providing one or more of the following types: MEMS deformable mirror, deformable liquid lens, deformable diffractive lens or mirror, liquid crystal phase modulator, controllable metamaterial lens or mirror, controllable photonic crystal lens or mirror (block 447). In some instances a further related feature regarding the transformable optical elements includes providing one or more variable aberration elements based on relative displacement or rotation of complementary layers (block 448).

Figure 10:
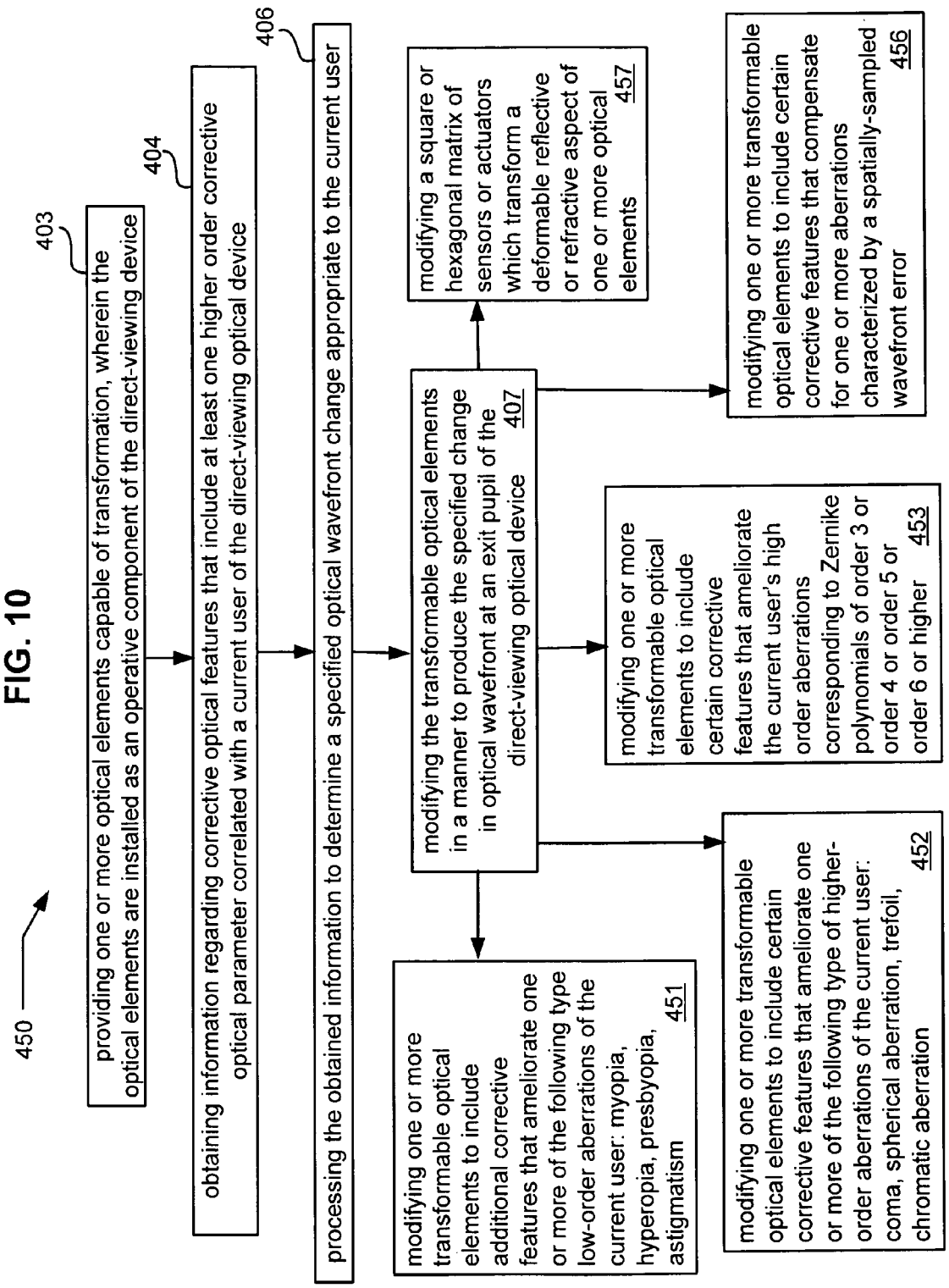

Referring to FIG. 10, additional exemplary process features 450 are shown including previously described features 403, 404, 406, 407 which may be combined with modifying one or more transformable optical elements to include additional corrective features that ameliorate one or more of the following type low-order aberrations of the current user: myopia, hyperopia, presbyopia, astigmatism (block 451). Another possible process feature include modifying one or more transformable optical elements to include certain corrective features that ameliorate one or more of the following type of higher-order aberrations of the current user: coma, spherical aberration, trefoil, chromatic aberration (block 452).

Some embodiments may provide an implementation that includes modifying one or more transformable optical elements to include certain corrective features that ameliorate the current user's high order aberrations corresponding to Zernike polynomials of order 3 or order 4 or order 5 or order 6 or higher (block 453). Other related aspects may include modifying the one or more transformable optical elements to include certain corrective features that compensate for one or more aberrations characterized by a spatially-sampled wavefront error (block 456). Further possible aspects include modifying a square or hexagonal matrix of sensors or actuators which transform a deformable reflective or refractive aspect of one or more optical elements (block 457).

Figure 11:
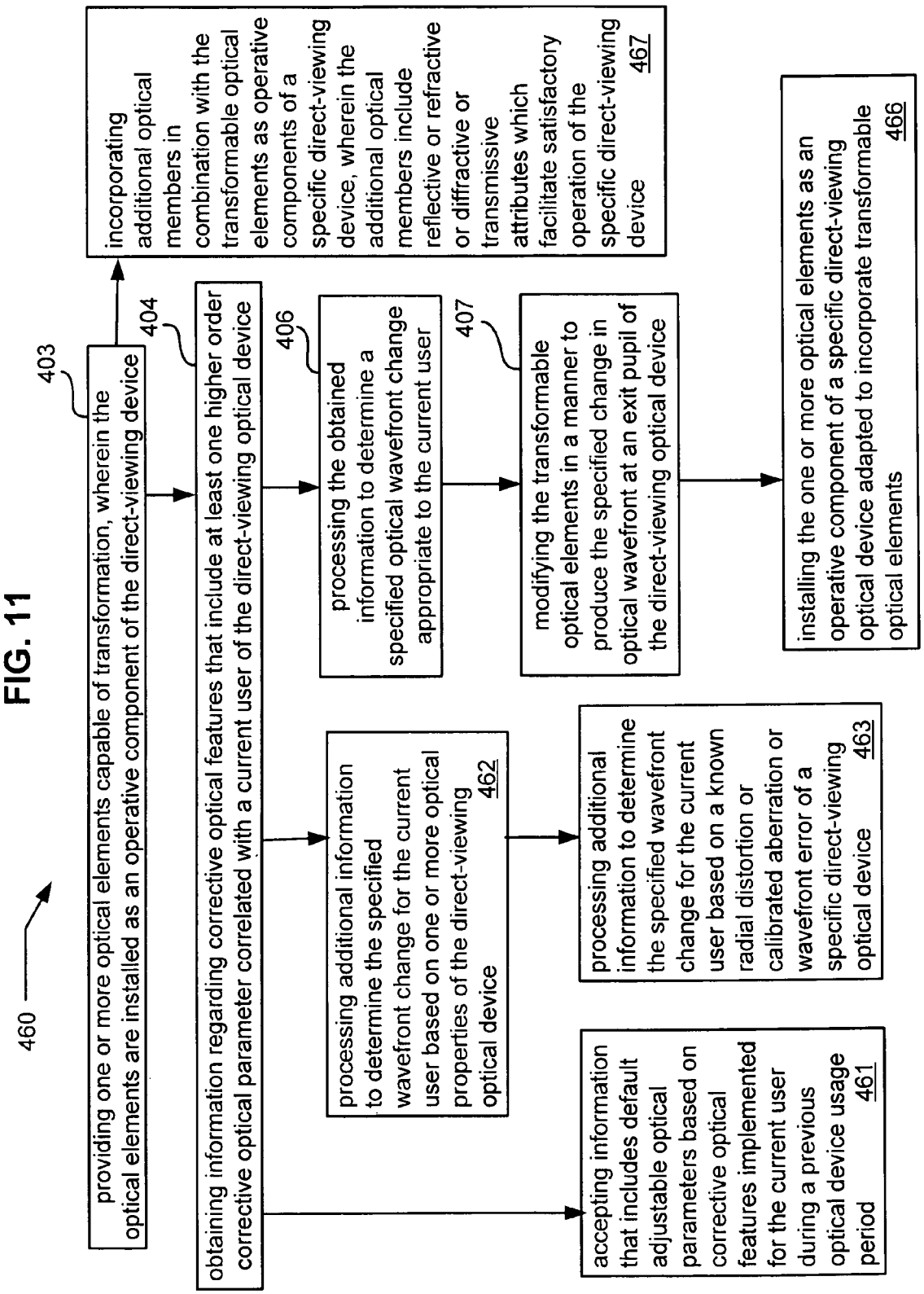

Various process features 460 depicted in the flow chart of FIG. 11 include previously described aspects 403, 404, 406, 407 as well as accepting information that includes default adjustable optical parameters based on corrective optical features implemented for the current user during a previous optical device usage period (block 461). Another possible process feature includes processing additional information to determine the specified wavefront change for the current user based on one or more optical properties of the direct-viewing optical device (block 462). A further illustrated aspect includes processing additional information indicating automatic adjustable optical parameters for the current user based on a known radial distortion or calibrated aberration or wavefront error of a specific direct-viewing optical device (block 463).

Some process embodiments include installing the one or more optical elements as an operative component of a specific direct-viewing optical device adapted to incorporate transformable optical elements (block 466). A further process aspect may include incorporating additional optical members in combination with the transformable optical elements as operative components of the specific direct-viewing device, wherein the additional optical members include reflective or refractive or diffractive or transmissive attributes which facilitate satisfactory operation of the direct-viewing device (block 467).

Figure 12:
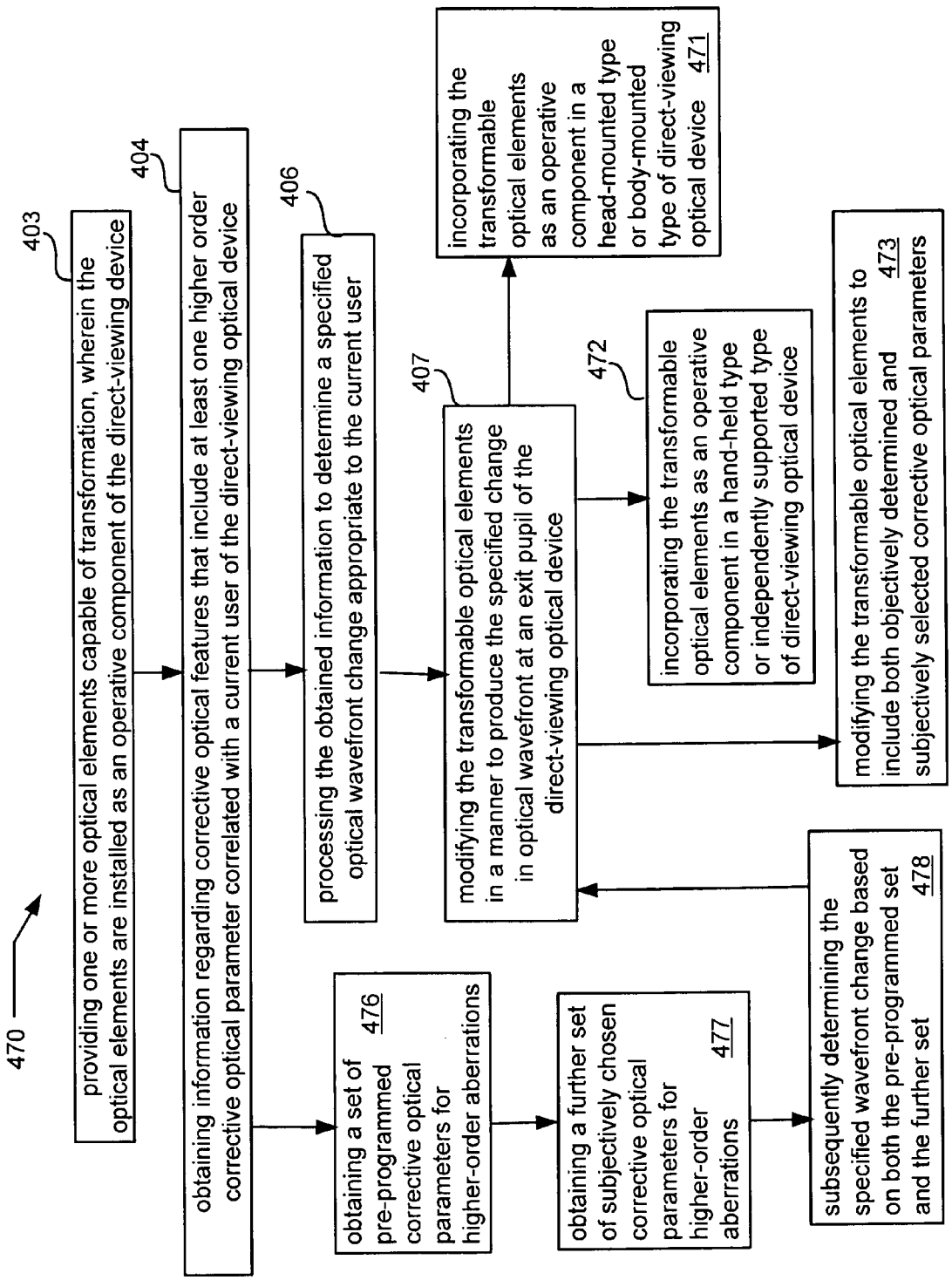

The detailed flow chart of FIG. 12 illustrates other embodiment features 470 including previously described process operations 403, 404, 406, 407 in combination with modifying the transformable optical elements to include both objectively determined and subjectively selected corrective optical parameters (block 473). Some exemplary embodiments may include incorporating the transformable optical elements as an operative component in a head-mounted type or body-mounted type of direct-viewing optical device (block 471). Other embodiments may include incorporating the transformable optical elements as an operative component in a hand-held type or independently supported type of direct-viewing optical device (block 472).

Additional related process aspects may include obtaining a set of pre-programmed corrective optical parameters for higher-order aberrations (block 476), and also obtaining a further set of subjectively chosen corrective optical parameters for higher-order aberrations (block 477), and subsequently determining the specified wavefront change based on both the pre-programmed set and the further set (block 478).

As illustrated in FIG. 13, various process features 480 may include previously described aspects 403, 404, 406, 407 as well as enabling the current user to choose subjectively between a "better or worse" comparison of possible corrective optical features to be included in the transformable optical elements (block 481). Another process aspect may include receiving information indicating a right eye or left eye or both eyes which correspond to the corrective optical features correlated with the current user (block 482).

Additional possible enhancements include maintaining a data record that includes eye measurement data and/or corrective optical features respectively correlated with one or more particular users of a specific direct-viewing optical device (block 483). A related exemplary feature includes establishing a communication link between the data record and one or more additional direct viewing devices which are available to the one or more particular users (block 484).

Also depicted in FIG. 13 are further process examples including establishing an authorization protocol to confirm identification of the current user (block 486), and implementing confirmation of the current user by name or password or biometric matching or eye feature recognition (block 487).

Referring to the detailed flow chart of FIG. 14, various exemplary process aspects 490 include previously described operations 403, 404, 406, 407 as well as incorporating the transformable optical element that includes adjustable reflective and/or refractive and/or diffractive characteristics as an integral component of a specific direct-viewing device adapted for dedicated usage by an individual user (block 491). Other process aspects may include optionally incorporating the transformable optical element as an auxiliary component of a specific direct-viewing device, wherein the transformable optical element includes adjustable reflective and/or refractive and/or diffractive characteristics respectively correlated with one of several possible users of the specific direct-viewing optical device (block 492).

Other process enhancements may include implementing dynamic adjustment of the transformable optical element currently installed in the direct-viewing optical device, wherein such dynamic adjustment includes static control or periodic control or continuous control of the transformable optical element during a real-time optical device usage period of the current user (block 493).

It will be understood from the exemplary embodiments disclosed herein that numerous individual method operations depicted in the flow charts of FIGS. 6-14 can be incorporated as encoded instructions in computer readable media in order to obtain enhanced benefits and advantages.

As another embodiment example, FIG. 15 shows a diagrammatic flow chart 500 depicting an article of manufacture which provides computer readable media having encoded instructions for executing a corrective method for a direct-viewing optical device (see 502), wherein the method includes confirming identity of a current user of a direct-viewing optical device having one or more optical elements capable of transformation (block 503), obtaining information regarding corrective optical features that include at least one higher order corrective optical parameter correlated with the current user (block 504), and processing the obtained information to determine a specified optical wavefront change appropriate to the current user (block 506). Additional programmed aspects may include enabling modification of the transformable optical elements in a manner to produce the specified change in optical wavefront at an exit pupil of the direct-viewing optical device (block 507).

Another programmed method aspect may include activating a square or hexagonal matrix of sensors or actuators which transform a deformable reflective or refractive aspect of the one or more optical elements (block 508). Additional programmed method aspects may include enabling static control or periodic control or continuous control of the transformable optical elements during a real-time optical device usage period of the current user (block 509). In some instances a static control may provide a one-time setting per user (e.g., mechanically moved optical elements). In another instance a periodic control may refresh at intervals (e.g., liquid crystal phase modulator). In a further instance a continuous control must drive continuously (e.g., piezo-electric deformable mirror).

Further possible programmed aspects may include maintaining a data table or database that includes a listing of possible users and their respective optical aberrations and/or corrective optical parameters and/or preferences (block 511). As a further aspect responsive to the confirmed identity of the current user, a programmed method may include retrieving from the data table or database their respective optical aberrations or corrective optical parameters or preferences (block 512). Some programmed embodiments may include enabling modification of the transformable optical elements to include both objectively determined and subjectively selected corrective optical parameters (block 514).

Referring to the representative set of data table records 600 illustrated in FIG. 16, various categories of performance viewing factors 610 are listed, as for example, field of view 612, brightness 614, and scene contrast 618. Ongoing variations of such factors may require adjustment of corrective optical parameters to achieve better visual acuity for a particular current user of a direct-viewing optical device. Other categories of pertinent performance viewing factors that may require adjustment of corrective optical parameters 610 may include spatial frequency content 622 and spectral attributes 624, as well as a focal length of the optical device 626 and a current aperture stop 628. In some instances a variation of the diameter of a current user's pupil 632 may cause an adverse effect that diminishes visual acuity. In the absence of an indicated corrective preference by a current user that would be applicable to a particular monitored viewing factor, a generic default correction 632 may be automatically implemented.

Some data entries regarding corrective optical parameters may be respectively maintained for multiple prospective users of a device. For example, a separate corrective parameter listing is applicable to a user ID "Bill" during his usage of optical device XX (see 615), and another separate (and possibly different) corrective parameter listing is applicable during his usage of optical device YY (see 620). Another example shows a separate corrective parameter listing applicable to a user ID "Ann" during her usage of optical device XX (see 625). A further example shows a separate corrective parameter listing applicable to a user ID "Eva" during her usage of optical device YY (see 630), and another separate (and possible different) corrective parameter listing that is applicable to her usage of optical device ZZ (see 635).

Some performance viewing factors 610 may be ignored with respect to particular devices and/or for particular user IDs, depending on individual user preferences. For example, usage of device XX by user ID "Bill" and also by user ID "Ann" does not require any correlated corrective parameter with respect to any identified target object (see 642, 644). As another example, usage of device ZZ by user ID "Eva" does not require any correlated corrective parameter with respect to any particular field of view (see 646), or with respect to variable spectral attributes (see 647). As a further example, usage of device YY by user ID "Bill" and also by user ID "Eva" does not require any correlated corrective parameters with respect to monitoring a user's pupil diameters (see 648, 649).

It will be understood that the categories and informational entries shown in the data table records of FIG. 16 are for purposes of illustration only, and may be expanded or altered in some embodiments and may be shortened or omitted in other embodiments depending on the circumstances.

Figure 17:
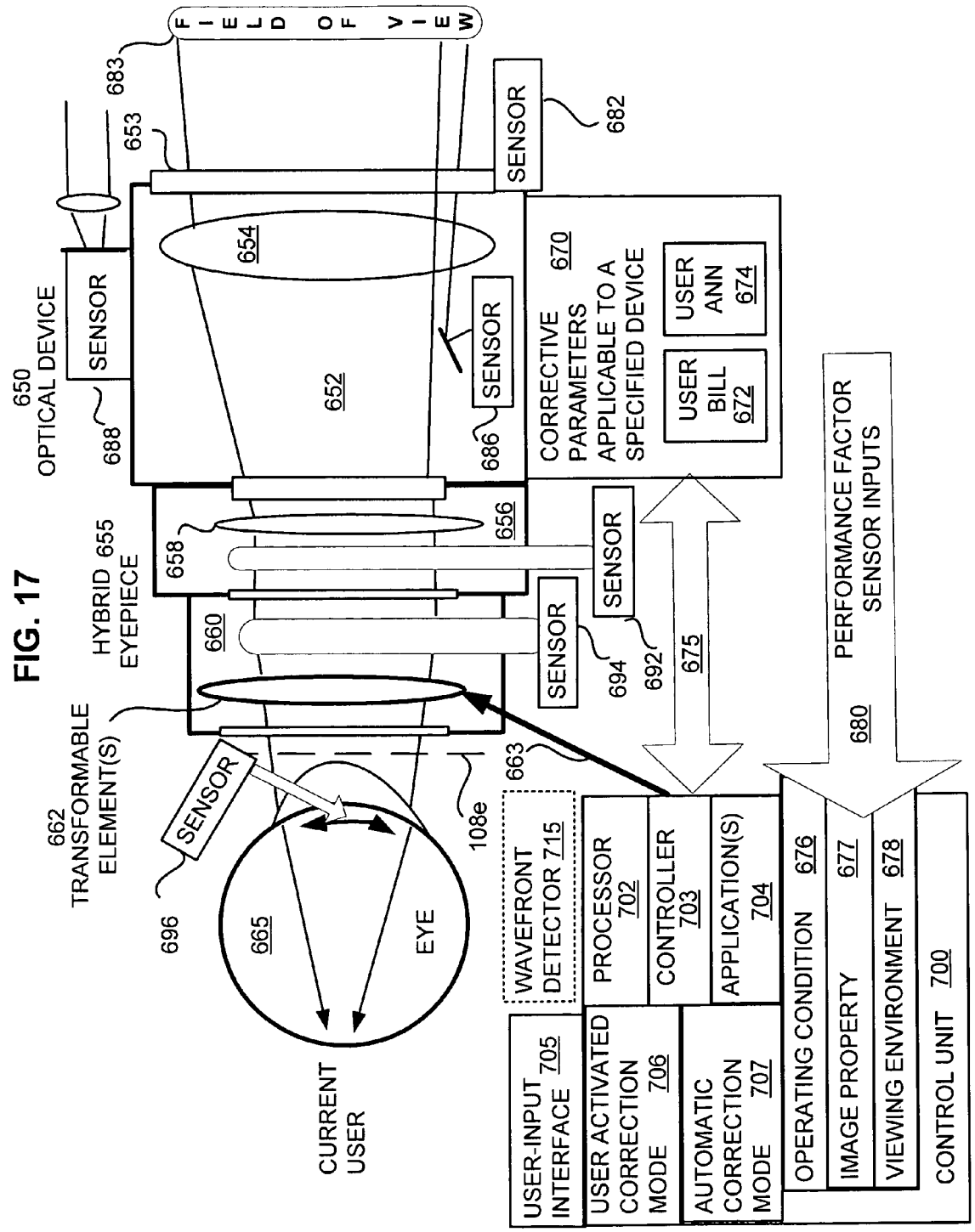
FIG. 17 is a schematic block diagram illustrating various aspects of obtaining and processing different types of optical device viewing parameters.

The schematic block diagram of FIG. 17 illustrates an embodiment for optical device 650 having a body portion 652 that includes aperture 653, other optical elements (e.g., refractive element 654) for viewing a particular field of view 683. The exemplary optical device 650 also includes a hybrid eyepiece 655 having a first eyepiece portion 656 with various optical elements (e.g., see refractive element 658), and a second eyepiece portion 660 with one or more transformable elements (e.g., see 662).

Also associated with optical device 650 is an exemplary data record 670 for corrective parameters applicable to a specified device. A separate listing of such corrective parameters may be respectively maintained for individual users of the specified optical device 650 (e.g., see user Bill 672, user Ann 674). The data record 670 is available for both "read" and "write" access through connecting link 675 to control unit 700 to enable processing of known and/or updated information that is necessary for adjusting the transformable elements 662 during a period of usage by an identified current user. An operatively coupled communication channel (e.g., see line 663) provides the static control or periodic control or continuous control of the transformable elements 662 in accordance with automatic and/or optional customized adjustment parameters initiated by the control unit 700.

The exemplary control unit 700 includes processor 702, controller 703, one or more applications 704, user-input interface 705, and in some instances may include a wavefront detector 715. It will be understood that real-time optical adjustments may be implemented pursuant to circuitry and/or software programming for an automatic correction mode 707 or a user activated correction mode 706 regarding transformable elements 662. It is therefore possible to provide a specified real-time change in optical wavefront at an exit pupil (e.g., see approximate exit pupil plane 108e) based on both objective implementation and/or subjective selection of corrective optical parameters to ameliorate low-order and/or high-order aberrations of a current user of the optical device 650.

Various sensors are symbolically shown (see 682, 686, 688, 692, 694) for monitoring and obtaining required measurements etc. that are indicative of the ongoing performance viewing factors during a current usage period of the optical device 650. An additional sensor 696 may be configured to determine a pupil diameter of a current user's eye 665 during the usage period. The various performance factor sensor outputs (e.g., see 680) are transmitted to the control unit 700 for real-time processing in order to achieve dynamic adjustment of the transformable elements 662. As indicated on the data table records 600 of FIG. 16, it may be helpful to provide different adjustment guidelines depending on the viewing parameter topics. In that regard sensor input data may be segregated for appropriated processing into different categories such as operating condition data 676, image properties 677, and viewing environment data 678.

Figure 18:
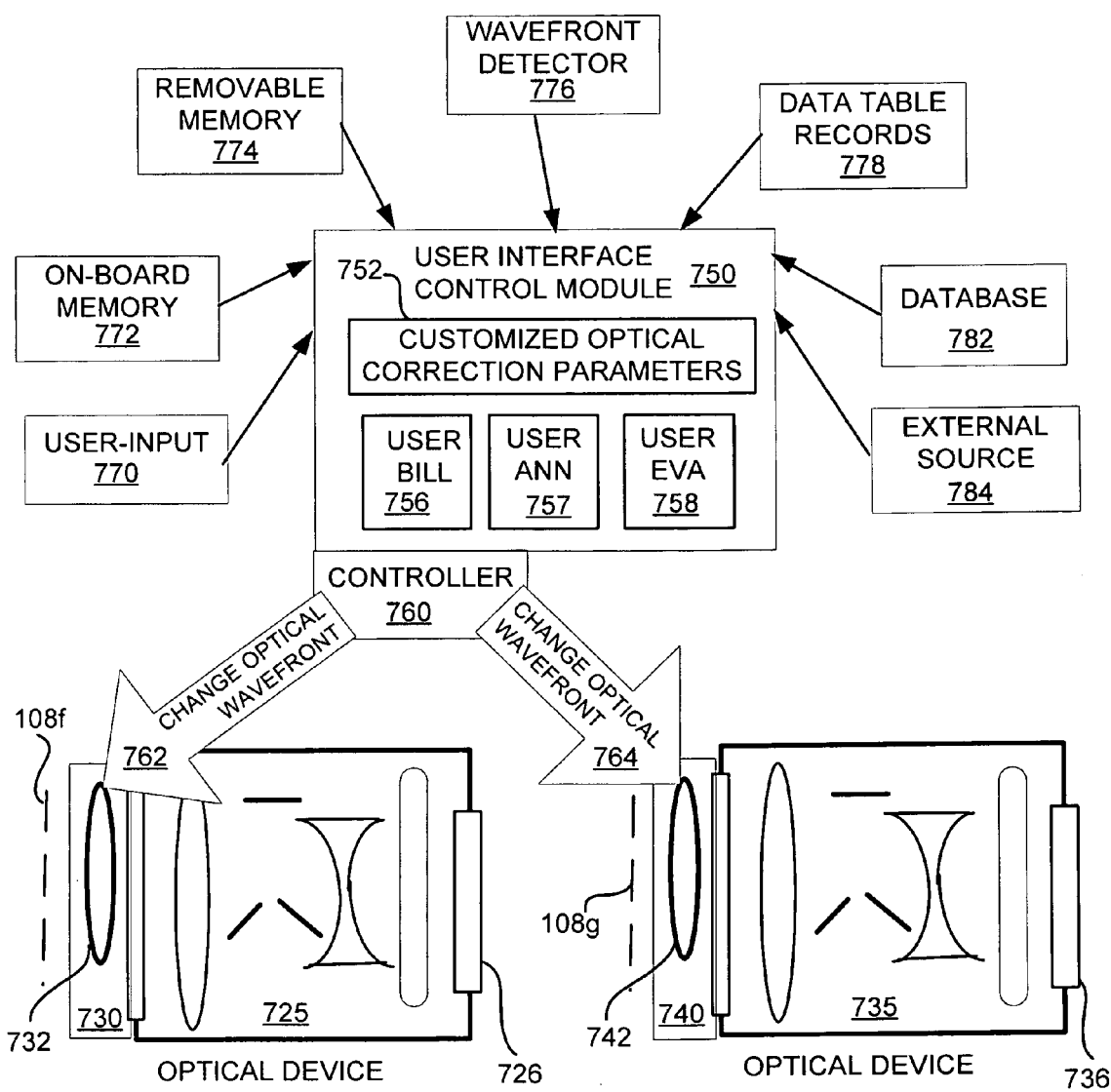
FIG. 18 is a schematic block diagram showing examples of data processing techniques for adjusting transformable optical elements in different optical devices.

Referring to the schematic block diagram of FIG. 18, various possible data processing techniques may be implemented with a user interface control module 750 with regard to customized optical correction parameters 752 related to user Bill 756, user Ann 757, and user Eva 758. Informational data regarding eye measurements and/or low/high order aberrations and/or corrective optical parameters for a prospective or current device user may be accessible to the user interface control module 750. For example, known data may be obtained from an external source 784, or a database 782, or data table records 778. Additional availability of such informational data may be obtained from user-input 770, on-board memory 772, or removable memory 774. In some instances newly updated information data may be obtained from a wavefront detector 776 directly associated with the optical direct-viewing device.

It will be understood that the illustrated interface control module 750 includes controller 760 that generates a first control signal 762 for changing an optical wavefront at an exit pupil (e.g., see approximate exit pupil plane 108f) pursuant to a real-time adjustment of transformable optical element(s) 732. Such a real-time customized adjustment provides enhanced acuity for a current user's view through aperture 726 of direct-viewing optical device 725. Similarly the illustrated controller 760 generates a second control signal 764 for changing an optical wavefront at an exit pupil (e.g., see approximate exit pupil plane 108g) pursuant to a real-time adjustment of transformable optical element(s) 742. Such a real-time customized adjustment provides enhanced acuity for another current user's view through aperture 736 of direct-viewing optical device 735.

Figure 19:
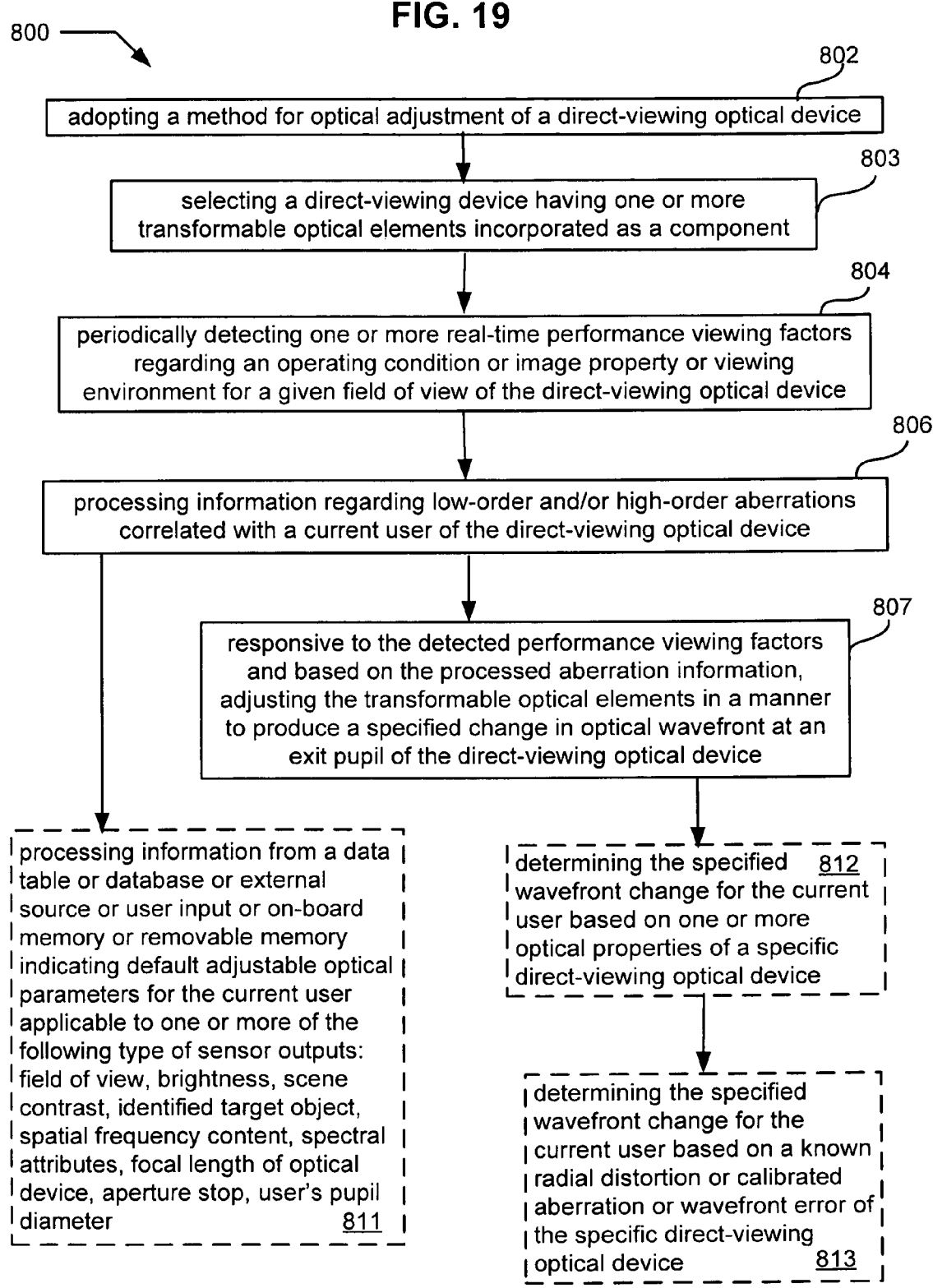
FIG. 19 is a high level flow chart showing exemplary method aspects regarding optical corrections based on optical device viewing parameters.

The high level flow chart of FIG. 19 illustrates exemplary embodiment features 800 regarding adoption of an optical adjustment method for a direct-viewing optical device (see block 802), including selecting a direct-viewing device having one or more transformable optical elements incorporated as a component (block 803), periodically detecting one or more real-time performance viewing factors regarding an operating condition or image property or viewing environment for a given field of view of the direct-viewing optical device (block 804), and processing information regarding low-order and/or high-order aberrations correlated with a current user of the direct-viewing optical device (block 806). Related process features that are responsive to the detected performance viewing factors and are based on the processed aberration information include adjusting the transformable optical elements in a manner to produce a specified change in optical wavefront at an exit pupil of the direct-viewing optical device (block 807).

Additional process aspects may include processing information from a data table or database or external source or user input or on-board memory or removable memory indicating default adjustable optical parameters for the current user applicable to one or more of the following type of sensor outputs: field of view, brightness, scene contrast, identified target object, spatial frequency content, spectral attributes, focal length of optical device, aperture stop, user's pupil diameter (block 811). Other examples include determining the specified wavefront change for the current user based on one or more optical properties of a specific direct-viewing optical device (block 812), and in some instances determining the specified wavefront change for the current user based on a known radial distortion or calibrated aberration or wavefront error of the specific direct-viewing optical device (block 813).

Figure 20:
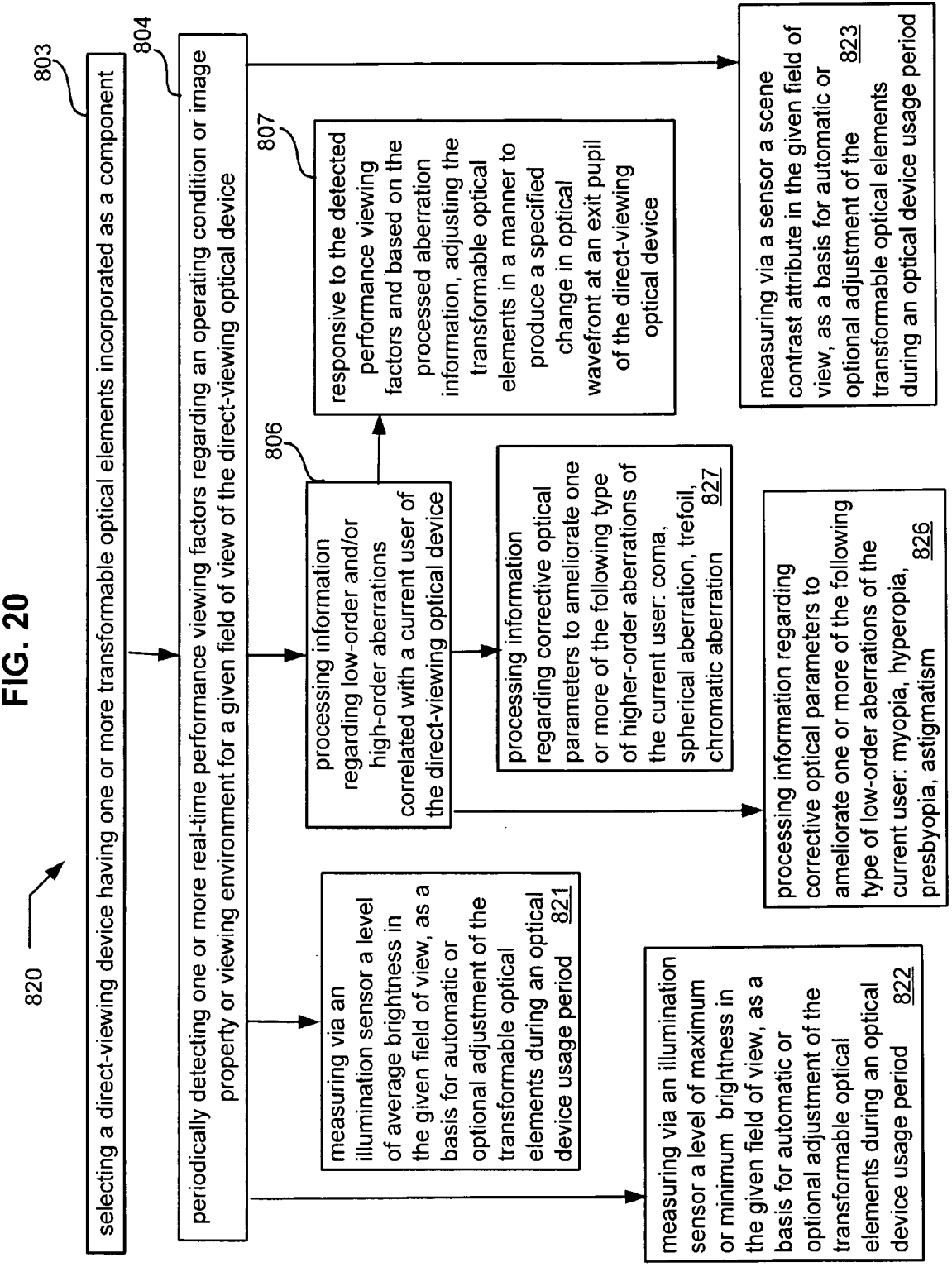
FIGS. 20-28 are detailed flow charts illustrating additional exemplary method aspects applicable to optical device viewing parameters.

Referring to the illustrated process examples 820 depicted in the flow chart of FIG. 20, an embodiment may include previously described aspects 803, 804, 806, 807 along with processing information regarding corrective optical parameters to ameliorate one or more of the following type of low-order aberrations of the current user: myopia, hyperopia, presbyopia, astigmatism (block 826). Another process example includes processing information regarding corrective optical parameters to ameliorate one or more of the following type of higher-order aberrations of the current user: coma, spherical aberration, trefoil, chromatic aberration (block 827).

Further possibilities include measuring via an illumination sensor a level of average brightness in the given field of view, as a basis for automatic or optional adjustment of the transformable optical elements during an optical device usage period (block 821). Another possible aspect includes measuring via an illumination sensor a level of maximum or minimum brightness in the given field of view, as a basis for automatic or optional adjustment of the transformable optical elements during an optical device usage period (block 822). A further process example includes measuring via a sensor a scene contrast attribute in the given field of view, as a basis for automatic or optional adjustment of the transformable optical elements during an optical device usage period (block 823).

Figure 21:
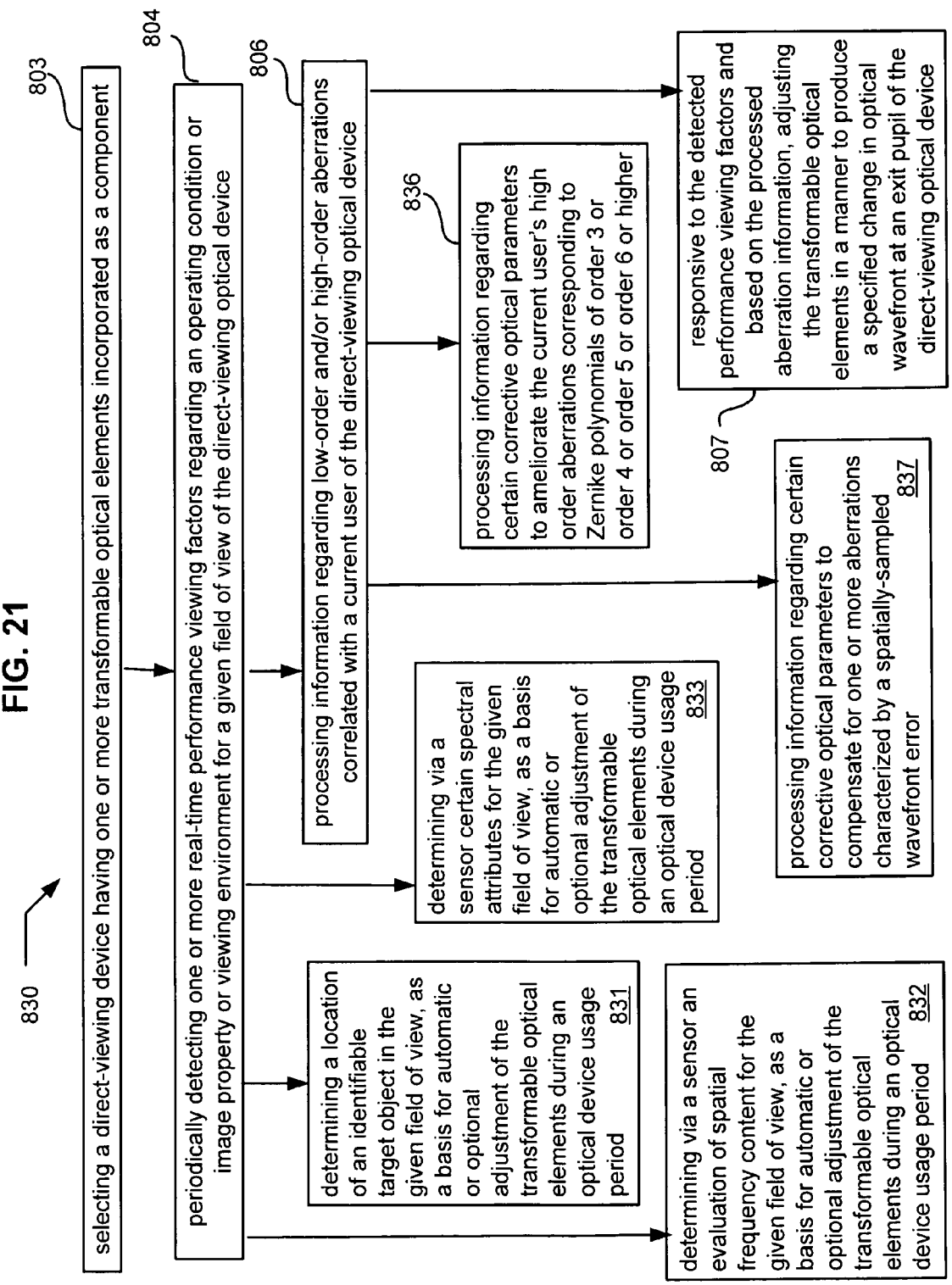

Referring to the detailed flow chart of FIG. 21, various illustrated embodiment features 830 include previously described aspects 803, 804, 806, 807 as well as additional examples such as determining a location of an identifiable target object in the given field of view, as a basis for automatic or optional adjustment of the transformable optical elements during an optical device usage period (block 831). Another example includes determining via a sensor an evaluation of spatial frequency content for the given field of view, as a basis for automatic or optional adjustment of the transformable optical elements during an optical device usage period (block 832).

In some instances an exemplary process includes determining via a sensor certain spectral attributes for the given field of view, as a basis for automatic or optional adjustment of the transformable optical elements during an optical device usage period (block 833). Another possibility includes processing information regarding certain corrective optical parameters to ameliorate the current user's high order aberrations corresponding to Zernike polynomials of order 3 or order 4 or order 5 or order 6 or higher (block 836). A further possible aspect includes processing information regarding certain corrective optical parameters to compensate for one or more aberrations characterized by a spatially-sampled wavefront error (block 837).

Figure 22:
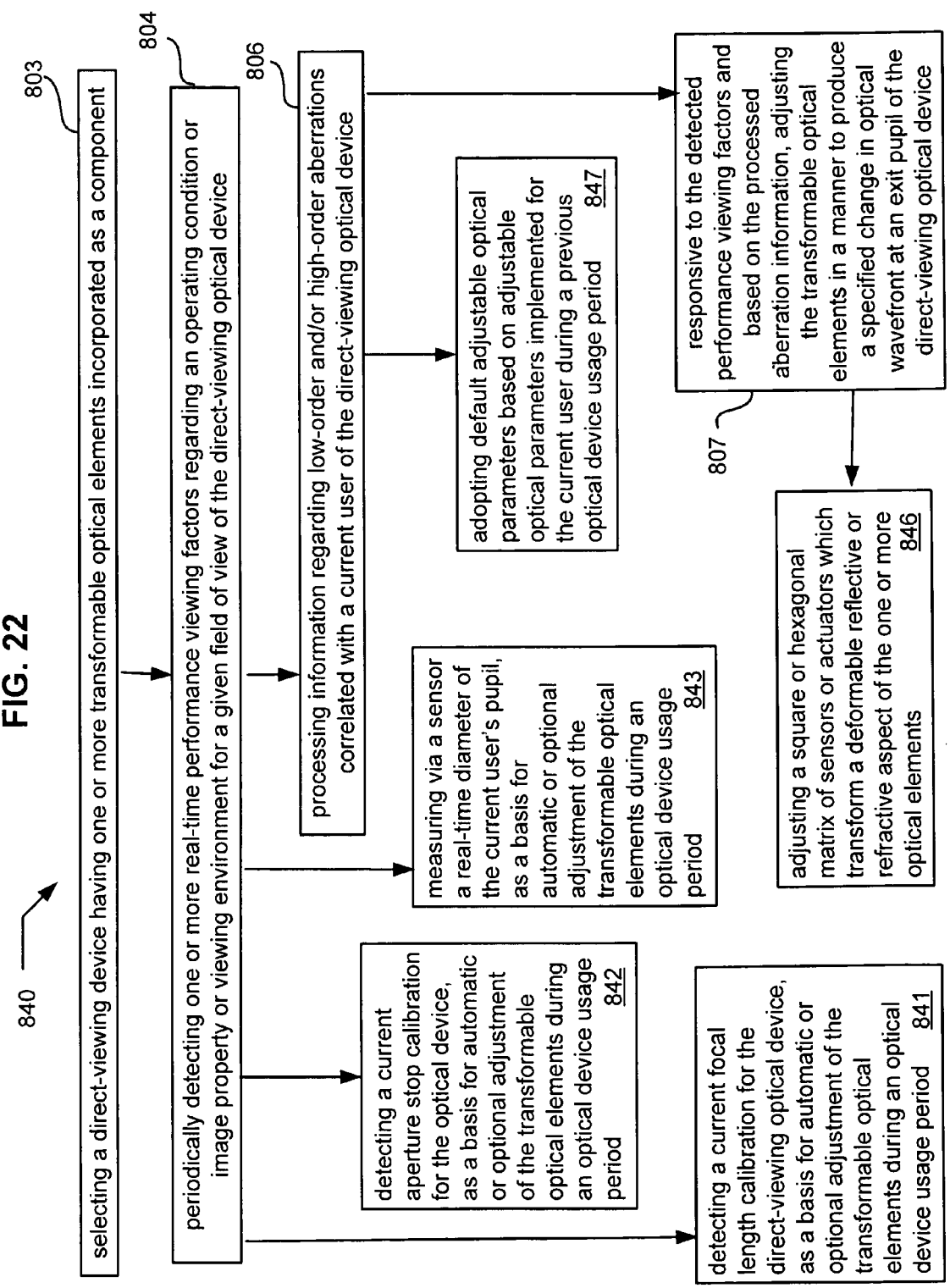

The exemplary process aspects 840 illustrated in FIG. 22 include previously described operations 803, 804, 806, 807 in combination with detecting a current focal length calibration for the direct-viewing optical device, as a basis for automatic or optional adjustment of the transformable optical elements during an optical device usage period (block 841). Another process feature may include detecting a current aperture stop calibration for the optical device, as a basis for automatic or optional adjustment of the transformable optical elements during an optical device usage period (block 842).

Another illustrated example includes measuring via a sensor a real-time diameter of the current user's pupil, as a basis for automatic or optional adjustment of the transformable optical elements during an optical device usage period (block 843). Further possibilities may include adjusting a square or hexagonal matrix of sensors or actuators which transform a deformable reflective or refractive aspect of the one or more optical elements (block 846). In some instances an example may include adopting the default adjustable optical parameters based on adjustable optical parameters implemented for the current user during a previous optical device usage period (block 847).

Figure 23:
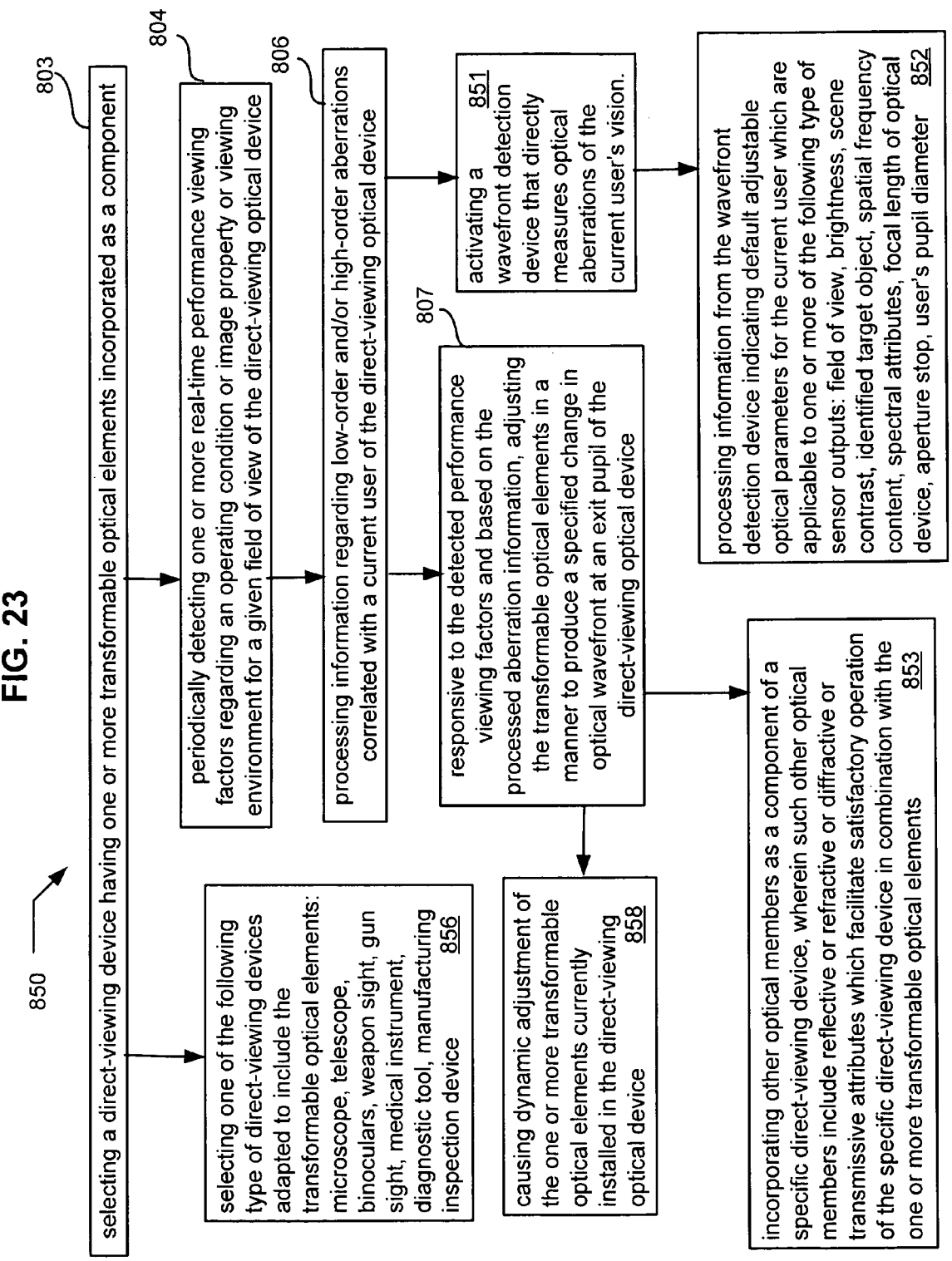

The detailed flow chart of FIG. 23 illustrates exemplary embodiment features 850 that include previously described aspects 803, 804, 806, 807 as well as activating a wavefront detection device that directly measures optical aberrations of the current user's vision (block 851). Related illustrated aspects include processing information from the wavefront detection device indicating default adjustable optical parameters for the current user which are applicable to one or more of the following type of sensor outputs: field of view, brightness, scene contrast, identified target object, spatial frequency content, spectral attributes, focal length of optical device, aperture stop, user's pupil diameter (block 852).

In some instances an enhancement may include incorporating other optical members as a component of a specific direct-viewing device, wherein such other optical members include reflective or refractive or diffractive or transmissive attributes which facilitate satisfactory operation of the specific direct-viewing device in combination with the one or more transformable optical elements (block 853). Other enhancements may include causing dynamic adjustment of the one or more transformable optical elements currently installed in the direct-viewing optical device (block 858).

Figure 24:
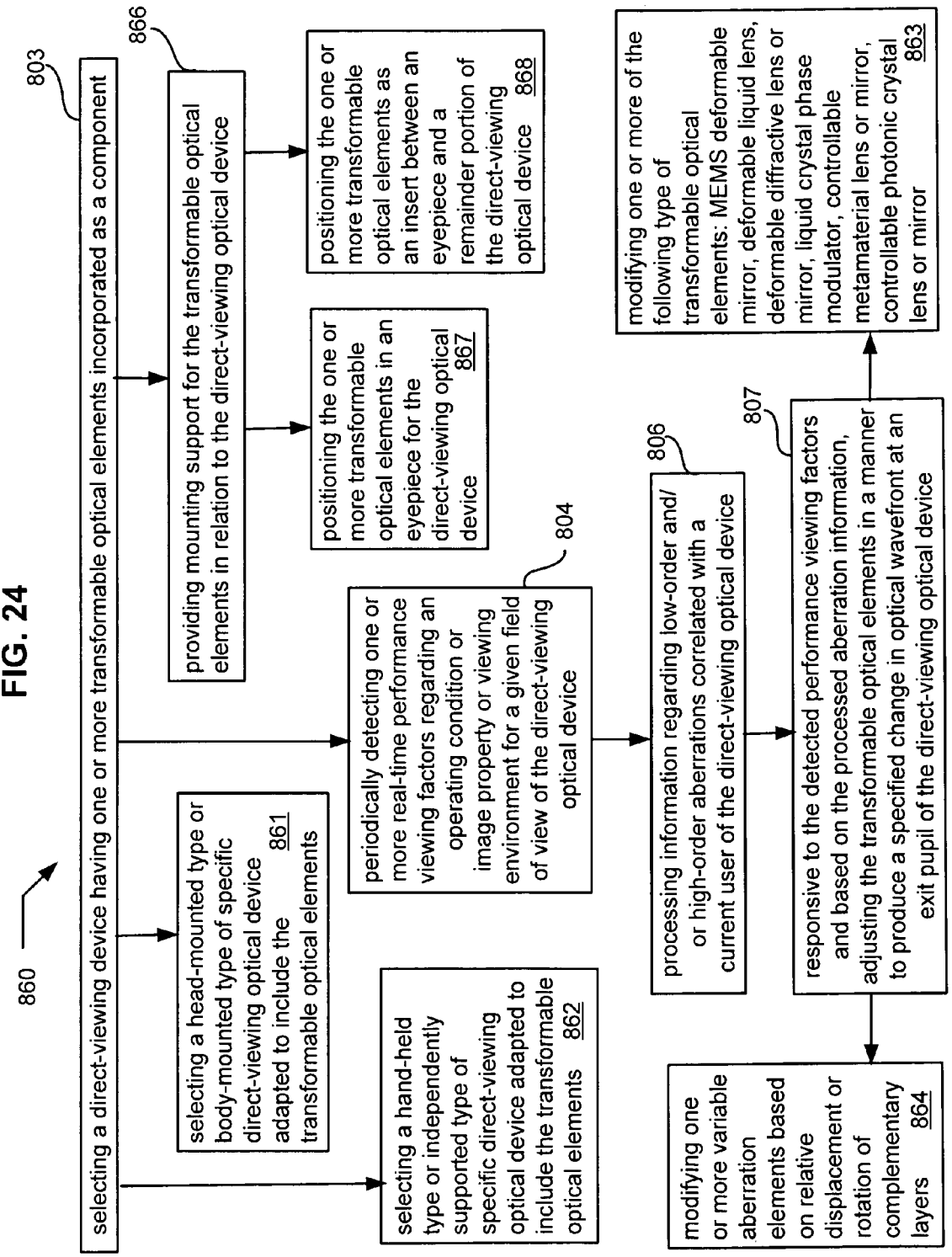

The detailed flow chart of FIG. 24 shows exemplary process aspects 860 that include previously described features 803, 804, 806, 807 in combination with selecting a head-mounted type or body-mounted type of specific direct-viewing optical device adapted to include the transformable optical elements (block 861), or in some instances in combination with selecting a hand-held type or independently supported type of specific direct-viewing optical device adapted to include the transformable optical elements (block 862).

Further process examples include modifying one or more of the following type of transformable optical elements: MEMS deformable mirror, deformable liquid lens, deformable diffractive lens or mirror, liquid crystal phase modulator, controllable metamaterial lens or mirror, controllable photonic crystal lens or mirror (block 863). Another process example includes modifying one or more variable aberration elements based on relative displacement or rotation of complementary layers (block 864).

As further illustrated in FIG. 24, other process examples include providing mounting support for the transformable optical elements in relation to the direct-viewing optical device (block 866), and in some instances positioning the one or more transformable optical elements in an eyepiece for the direct-viewing optical device (block 867). Another example includes positioning the one or more transformable optical elements as an insert between an eyepiece and a remainder portion of the direct-viewing optical device (block 868).

Figure 25:
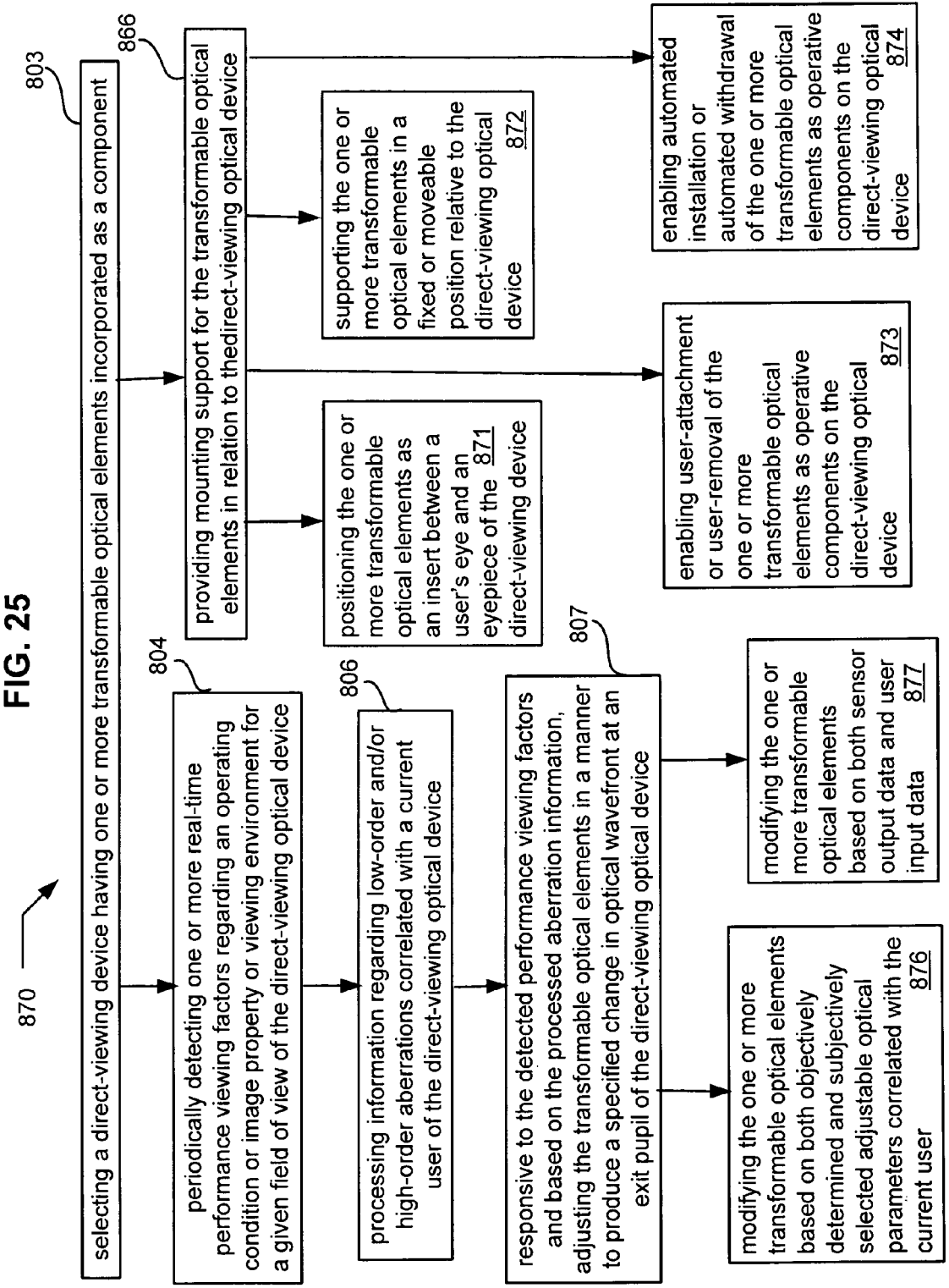

With regard to the exemplary process aspects 870 shown in FIG. 25, a possible embodiment may include previously described features 803, 804, 806, 807, 866 along with positioning the one or more transformable optical elements as an insert between a user's eye and an eyepiece of the direct-viewing device (block 871). Another possibility includes supporting the one or more transformable optical elements in a fixed or moveable position relative to the direct-viewing optical device (block 872).

A further possible aspect includes enabling user-attachment or user-removal of the one or more transformable optical elements as operative components on the direct-viewing optical device (block 873). Some enhancements may include enabling automated installation or automated withdrawal of the one or more transformable optical elements as operative components on the direct-viewing optical device (block 874).

Another possible aspect includes modifying the one or more transformable optical elements based on both objectively determined and subjectively selected adjustable optical parameters correlated with the current user (block 876). A further possibility includes modifying the one or more transformable optical elements based on both sensor output data and user input data (block 877).

Figure 26:
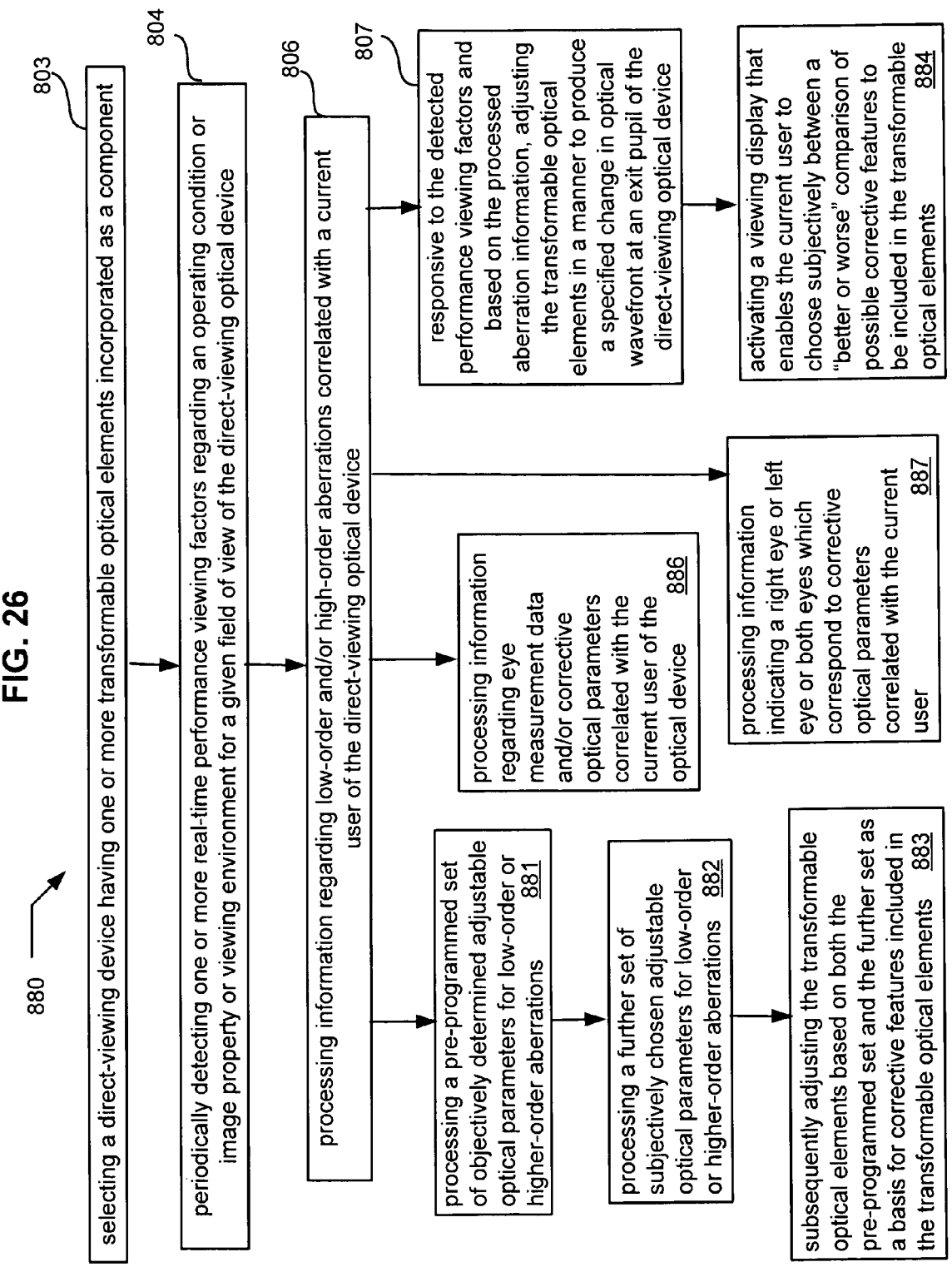

The flow chart of FIG. 26 relates to additional exemplary process features 880 that include previously described aspects 803, 804, 806, 807 along with activating a viewing display that enables the current user to choose subjectively between a "better or worse" comparison of possible corrective features to be included in the transformable optical elements.

Other illustrated process features 950 may include processing a pre-programmed set of objectively determined adjustable optical parameters for low-order or higher-order aberrations (block 881), and also processing a further set of subjectively chosen adjustable optical parameters for low-order or higher-order aberrations (block 882), and subsequently adjusting the transformable optical elements based on both the pre-programmed set and the further set as a basis for corrective features included in the transformable optical elements (block 883).

Additional aspects illustrated in FIG. 26 include processing information regarding eye measurement data and/or corrective optical parameters correlated with the current user of the optical device (block 886). Further possibilities include processing information indicating a right eye or left eye or both eyes which correspond to corrective optical parameters correlated with the current user (block 887).

Figure 27:
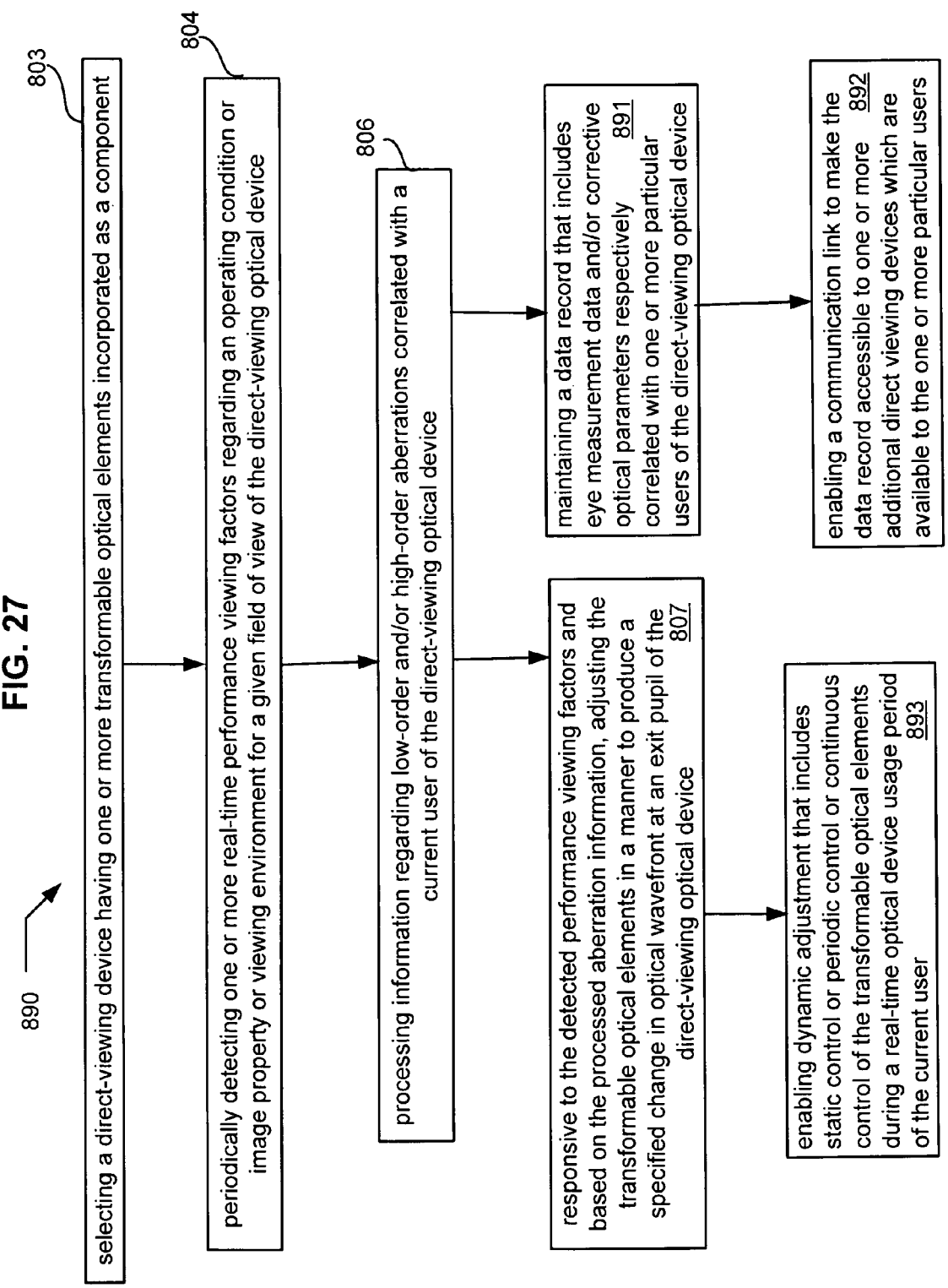

Referring to the detailed flow chart of FIG. 27, various exemplary process embodiment features 890 include previously described aspects 803, 80, 806, 807 in combination with maintaining a data record that includes eye measurement data and/or corrective optical parameters respectively correlated with one or more particular users of the direct-viewing optical device (block 891). A related process example includes enabling a communication link to make the data record accessible to one or more additional direct viewing devices which are available to the one or more particular users (block 892).

Another example includes enabling dynamic adjustment that includes static control or periodic control or continuous control of the transformable optical elements during a real-time optical device usage period of the current user (block 893).

Figure 28:
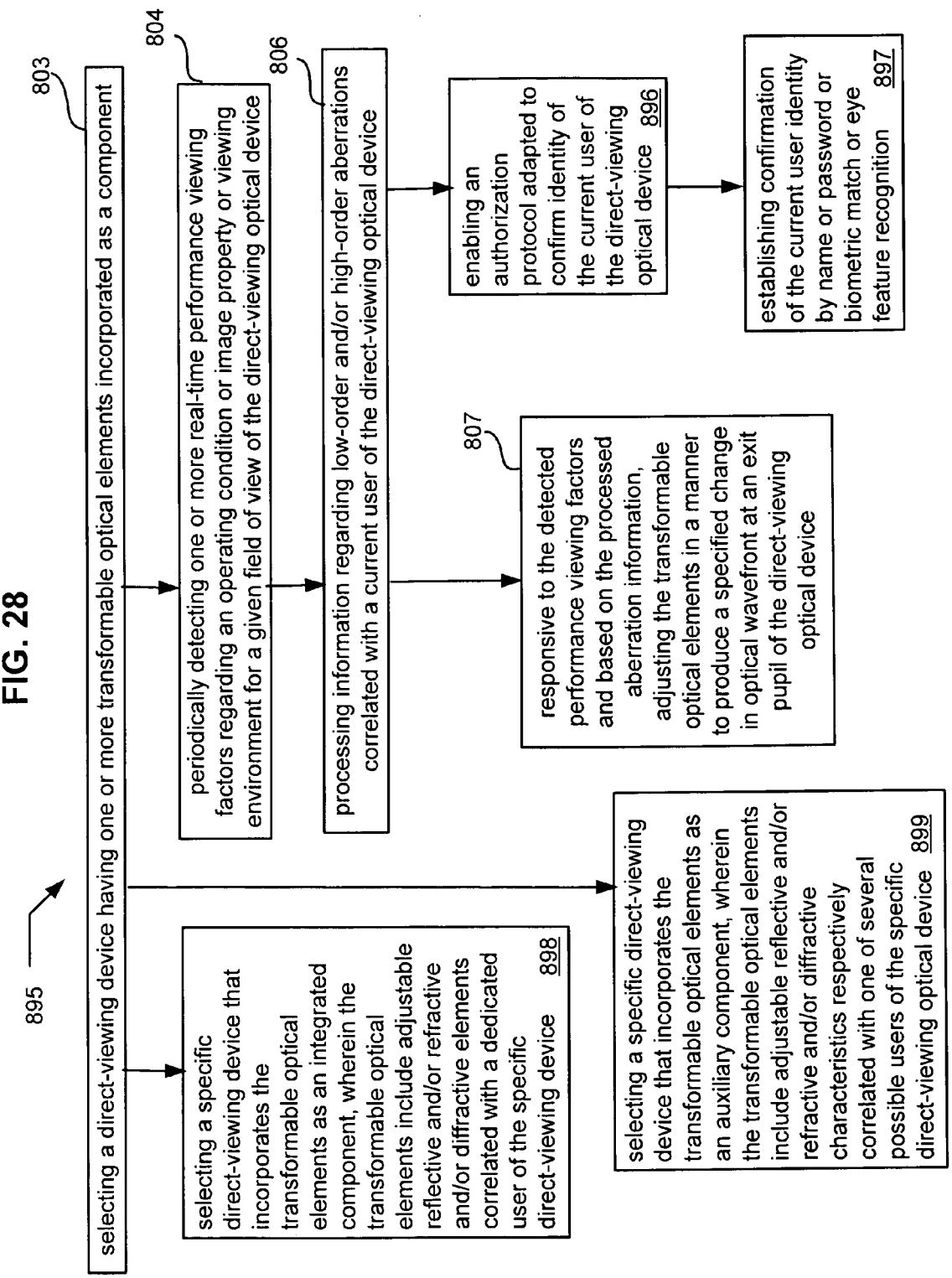

The detailed flow chart of FIG. 28 illustrates various exemplary process aspects 895 including previously described operations 803, 804, 806, 807 as well as enabling an authorization protocol adapted to confirm identity of the current user of the direct-viewing optical device (block 896). A related process aspect may include establishing confirmation of the current user identity by name or password or biometric match or eye feature recognition (block 897).

Some embodiments may further include selecting a specific direct-viewing device that incorporates the transformable optical elements as an integrated component, wherein the transformable optical elements include adjustable reflective and/or refractive and/or diffractive elements correlated with a dedicated user of the specific direct-viewing device (block 898). Another possible embodiment may include selecting a specific direct-viewing device that incorporates the transformable optical elements as an auxiliary component, wherein the transformable optical elements include adjustable reflective and/or refractive and/or diffractive characteristics respectively correlated with one of several possible users of the specific direct-viewing optical device (block 899).

It will be understood from the exemplary embodiments disclosed herein that numerous individual method operations depicted in the flow charts of FIGS. 19-28 can be incorporated as encoded instructions in computer readable media in order to obtain enhanced benefits and advantages.

As another embodiment example, FIG. 29 shows a diagrammatic flow chart 900 depicting an article of manufacture which provides computer-readable media having encoded instructions for executing an optical adjustment method for a direct-viewing optical device (block 902), wherein the method includes periodically detecting one or more real-time performance viewing factors regarding an operating condition or image property or viewing environment for a given field of view of the direct-viewing optical device that includes one or more transformable optical elements (block 903); processing information regarding low-order and/or high-order aberrations correlated with a current user of the direct-viewing optical device (block 904); and responsive to the detected performance viewing factors and based on the processed aberration information, adjusting the transformable optical elements in a manner to produce a specified change in optical wavefront at an exit pupil of the direct-viewing optical device (block 906).

Other possible programmed aspects include enabling automatic or optional adjustment of the transformable optical elements (block 911), and in some instances causing dynamic adjustment of one or more transformable optical elements currently installed in the direct-viewing optical device (block 912). Another example of a programmed aspect includes processing information regarding certain corrective optical parameters to compensate for one or more aberrations characterized by a spatially-sampled wavefront error (block 913). Further programmed method aspects may include processing information from the wavefront detection device indicating default adjustable optical parameters for the current user which are applicable to one or more of the following type of real-time performance viewing factors: field of view, brightness, scene contrast, identified target object, spatial frequency content, spectral attributes, focal length of optical device, aperture stop, user's pupil diameter (block 914).

The schematic block diagram of FIG. 30 illustrates an exemplary embodiment for an alignment optical correction system for a direct-viewing optical device 920 having a field of view 922. A customizable eyepiece 925 having a one or more transformable optical elements 930 is optically coupled with the optical device 920 for conventional viewing by a current user's eye 935. A solid line 931 indicates a reference that is perpendicular to an initial gaze direction of the eye 935. Sometimes a current user's gaze direction shifts (e.g., see eye 936) in a way that results in a changed optical path through the direct-viewing optical device 920 toward the field of view 922. A gaze direction detection module 940 is operatively coupled to control module 950 in order to transmit a monitored changed of the gaze direction of eye 936. This shifted gaze direction may adversely affect the acuity for visual objects in the field of view 922.

In response to the shifted gaze direction, an example of a first corrective operational response mode enables a control module 950 to send a control signal via communication channel 955 to the transformable optical elements 930 in order to cause an optical realignment of a central viewing axis of corrective parameters relative to shifted gaze direction 937 of eye 936. Such optical realignment is shown symbolically on FIG. 30 by revised dotted reference line 932 perpendicular to a new central viewing axis (see dotted arrow 938) of transformable optical elements 930.

It will be noted that control module 950 includes a processor 952 and one or more applications 952 for appropriate data processing to establish both an original adjustment of the transformable optical elements (i.e., based on wavefront aberrations associated with a current user), as well as an optical realignment of the transformable optical elements (i.e., based on the detected shift of the gaze direction). This first corrective operational response mode allows the customizable eyepiece 925 and its attached optical elements (e.g., 930) to remain in their usual fixed position attached to the optical device 920.

In response to the shifted gaze direction, an example of a second corrective operational response mode enables the control module 950 to send a control signal via another communication channel to stepper motor 971. As shown in an alternate view of a customizable eyepiece 965, the stepper motor 971 (or other motorized component) causes an automatic physical translation and/or rotation of the customizable eyepiece 965 and its attached optical elements (e.g., 970) on a pivotal base 962 to achieve a new physical realignment of the eyepiece 925 relative to the shifted gaze direction 961 of eye 960. Such physical realignment is shown symbolically on FIG. 30 by reference line 966 perpendicular to new central viewing axis (see arrow 967).

In some embodiments one or more of the attached optical elements (e.g., 970) may be separately configured to be physically repositioned via an adjustable mounting base (not shown) in response to the shifted gaze direction, while a supportive eyepiece body portion remains attached in a fixed position relative to the optical device 920. Optional manual repositioning may be another alternative in some embodiments, although calibrated precision control of such manual repositioning may be more difficult to achieve.

The control module 950 is operably coupled via access channel 975 to a data table listing 980 that includes information regarding optical aberrations of one or more prospective users of direct-viewing device 920. For example, data associated with a first user ID 990 may include low-order corrections 991 as well as well as high-order corrections 992. As another example, data associated with a second user ID 985 may include low-order corrections 986 as well as high-order corrections 987.

In some embodiments it may be desirable in implement both the first corrective operational response mode (i.e., optical transformation of the installed transformable optical elements) and also the second corrective operational response mode (i.e., physical realignment of the installed transformable optical elements) in order to minimize adverse optical deficiencies resulting from the shifted gaze direction of the current user. With respect to a direct-viewing optical device that does not include installed transformable optical elements, the customized non-transformable optical elements can be configured (e.g., supported on a pivotal base) to achieve physical realignment of such customized non-transformable optical elements to enhance acuity in response to a detected shift in gaze direction of the current user.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

Referring to the high-level flow chart of FIG. 31, various exemplary process features 1010 are illustrated with regard to adopting an alignment adjustment method for a direct-viewing optical device (see block 1012) which may include incorporating one or more corrective optical elements as an operative component in the direct-viewing optical device (block 1013), and may further include tracking a gaze direction of a particular user of the direct-viewing optical device during a period of optical device usage (block 1014). Another example includes responsive to detection of the tracked gaze direction, activating a control module to reposition or transform the corrective optical elements in a manner to produce a specified change in optical wavefront at an exit pupil of the direct-viewing optical device, wherein the specified change enhances optical acuity during varied gaze directions (block 1016).

Additional possible process features include implementing a first operational mode causing physical repositioning of certain corrective optical elements in response to a detected shift of the tracked gaze direction (block 1021). A related aspect may include activating a motorized component to cause translational and/or rotational physical realignment of certain corrective optical elements relative to the tracked gaze direction of the particular user (block 1022).

Also depicted in FIG. 31 is another exemplary process aspect that includes enabling a user-activated component to cause translational and/or rotational physical realignment of certain corrective optical elements relative to the tracked gaze direction of the particular user (block 1023). A further possibility includes enabling a physical realignment to cause a central viewing axis of certain corrective optical elements to be substantially parallel with the tracked gaze direction of the particular user (block 1024).

Some exemplary process embodiments include implementing a second operational mode causing dynamic adjustment of one or more transformable corrective optical elements currently installed in the direct-viewing optical device, in response to a detected shift of the tracked gaze direction (block 1026).

Figure 32:
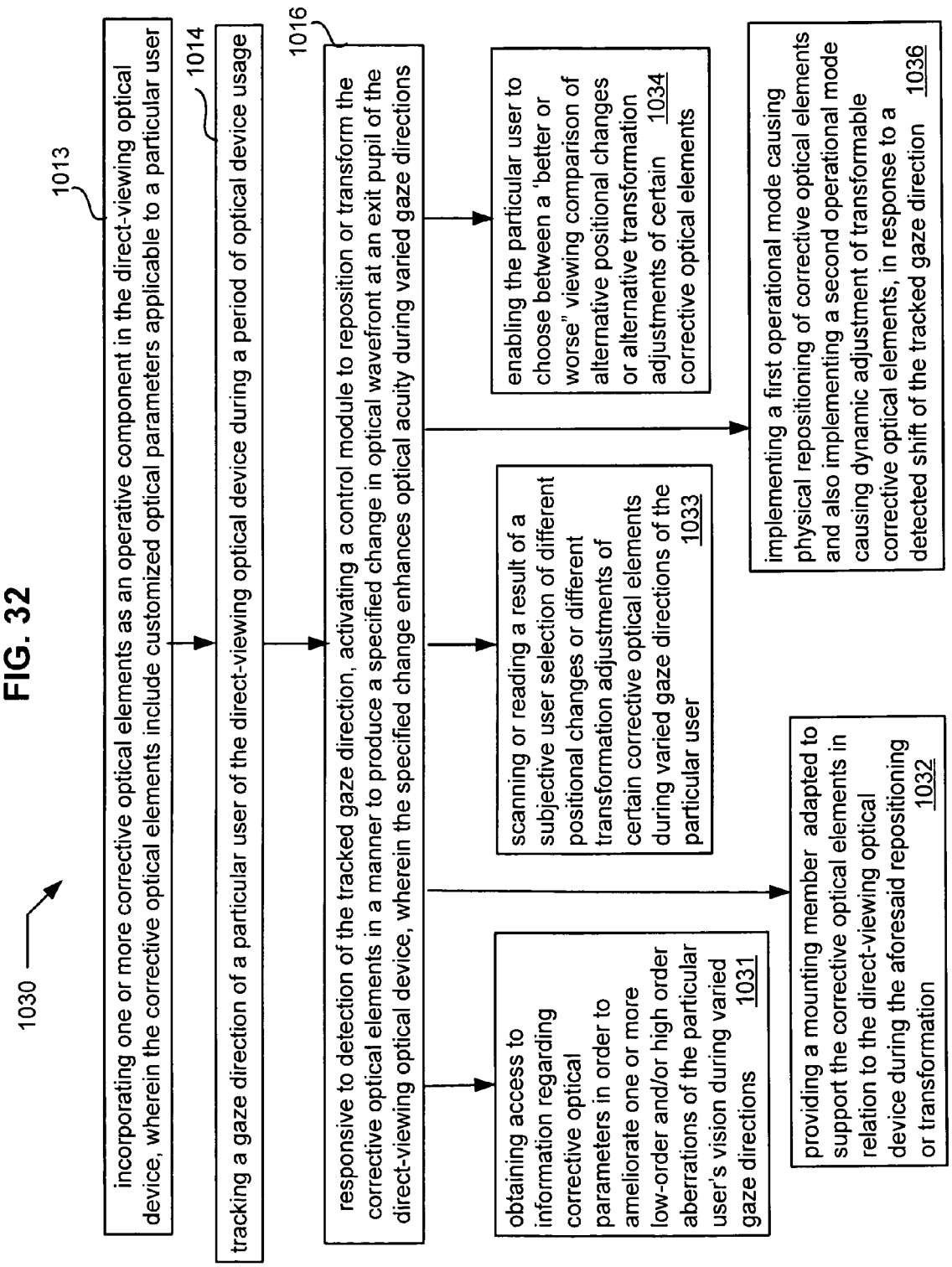
FIGS. 32-37 are detailed flow charts illustrating additional exemplary method aspects for adjustable optical alignment corrections.

The detailed flow chart of FIG. 32 illustrates various exemplary process operations 1030 including previously described aspects 1013, 1014, 1016 in combination with obtaining access to information regarding corrective optical parameters in order to ameliorate one or more low-order and/or high order aberrations of the particular user's vision during varied gaze directions (block 1031). Another aspect may include providing a mounting member adapted to support the corrective optical elements in relation to the direct-viewing optical device during the aforesaid repositioning or transformation (block 1032).

In some instances an example includes scanning or reading a result of a subjective user selection of different positional changes or different transformation adjustments of certain corrective optical elements during varied gaze directions of the particular user (block 1033). Another example may include enabling the particular user to choose between a "better or worse" viewing comparison of alternative positional changes or alternative transformation adjustments of certain corrective optical elements (block 1034).

Further aspects may include implementing a first operational mode causing physical repositioning of corrective optical elements and also implementing a second operational mode causing dynamic adjustment of transformable corrective optical elements, in response to a detected shift of the tracked gaze direction (block 1036).

Figure 33:
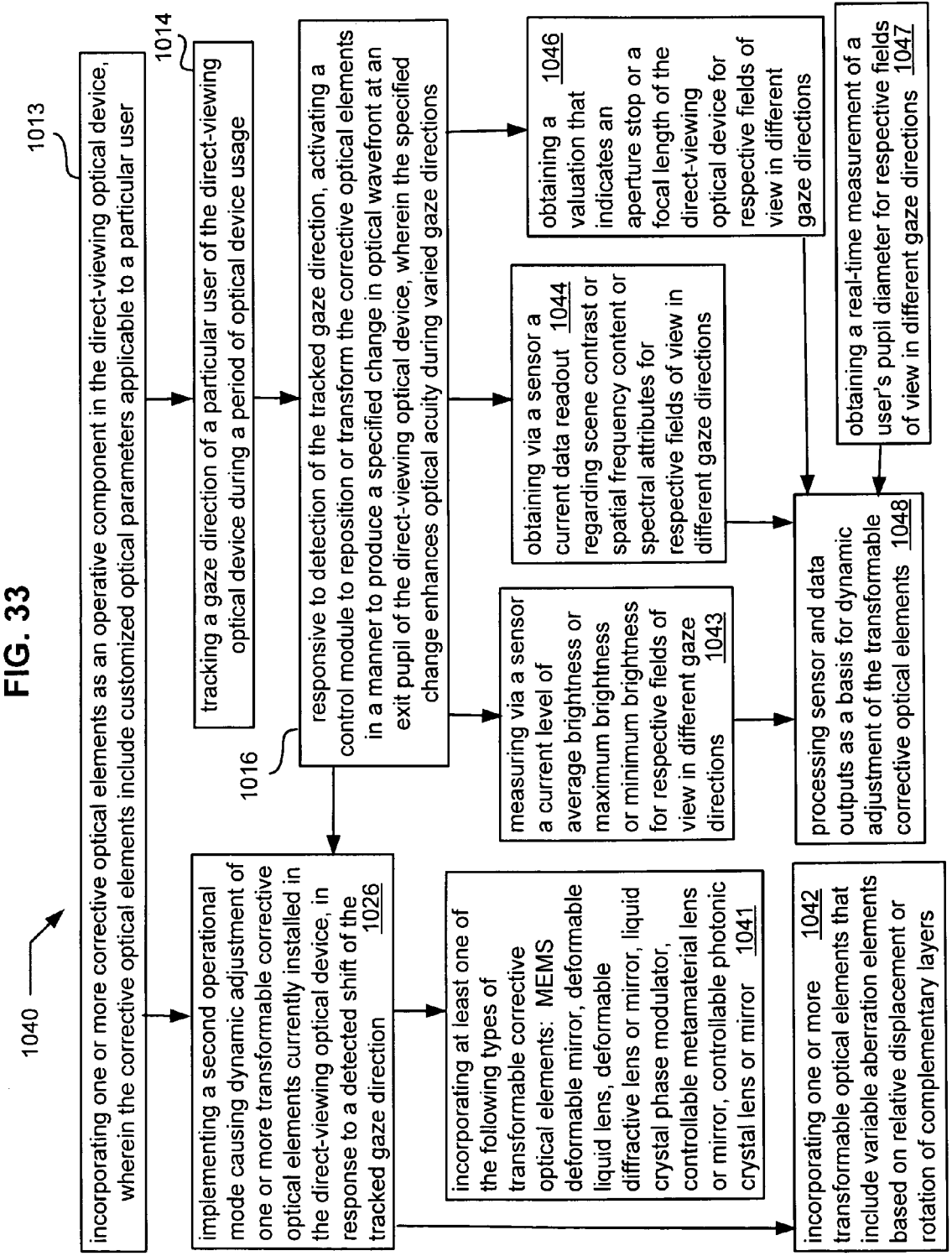

The illustrated process features 1040 of FIG. 33 include previously described aspects 1013, 1014, 1016, 1026 as well other possible aspects including incorporating at least one of the following types of transformable corrective optical elements: MEMS deformable mirror, deformable liquid lens, deformable diffractive lens or mirror, liquid crystal phase modulator, controllable metamaterial lens or mirror, controllable photonic crystal lens or mirror (block 1041). Another possibility includes incorporating one or more transformable optical elements that include variable aberration elements based on relative displacement or rotation of complementary layers (block 1042).

Additional aspects may include processing sensor and data outputs as a basis for dynamic adjustment of the transformable corrective optical elements (block 1048). A possible monitoring technique includes measuring via a sensor a current level of average brightness or maximum brightness or minimum brightness for respective fields of view in different gaze directions (block 1043). Other possibilities include obtaining via a sensor a current data readout regarding scene contrast or spatial frequency content or spectral attributes for respective fields of view in different gaze directions (block 1044).

Further techniques regarding sensor and data outputs may include obtaining a valuation that indicates an aperture stop or a focal length of the direct-viewing optical device for respective fields of view in different gaze directions (block 1046), and in some instances may include obtaining a real-time measurement of a user's pupil diameter for respective fields of view in different gaze directions (block 1047).

Figure 34:
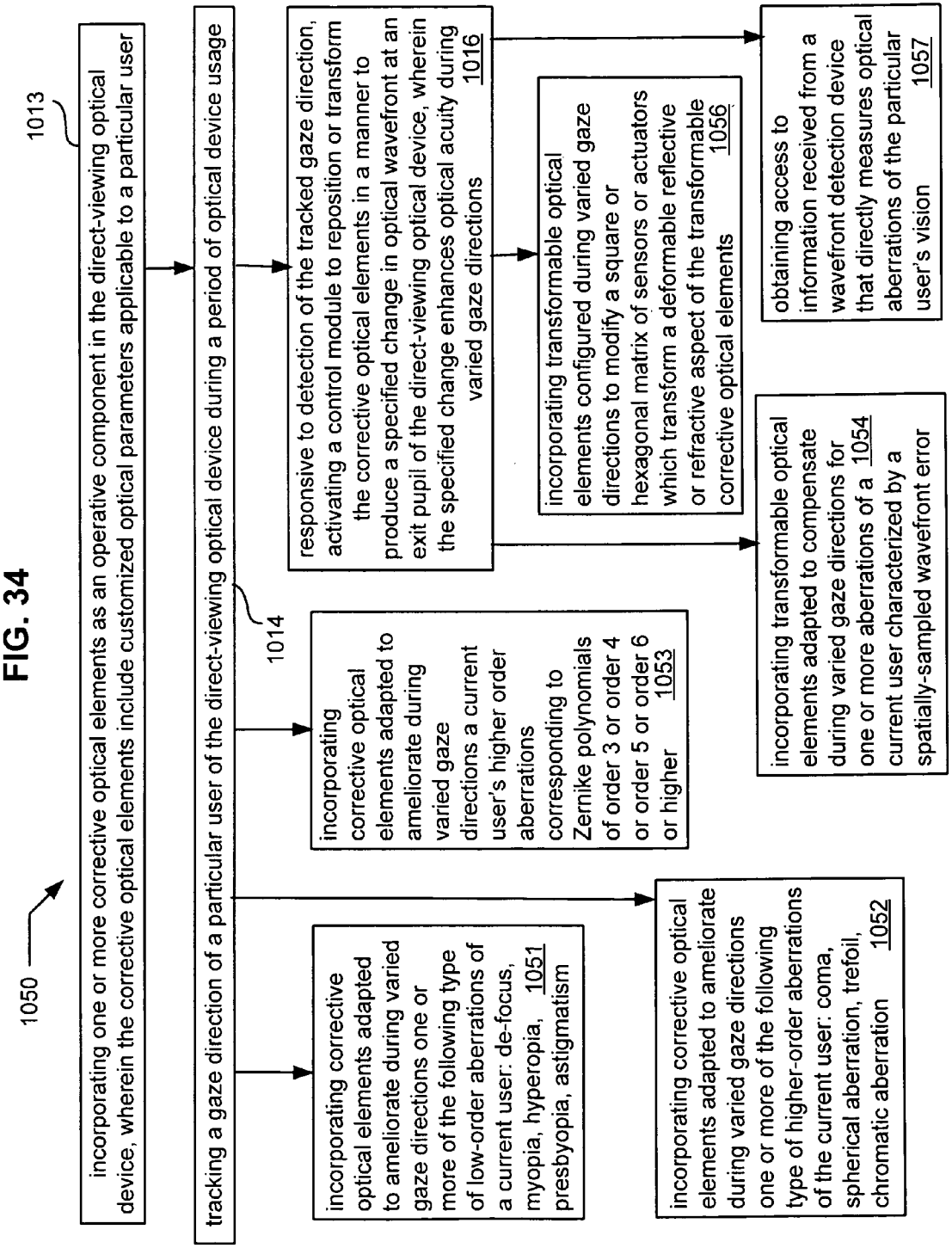

The detailed flow chart of FIG. 34 illustrates exemplary process enhancements 1050 that include previously described aspects 1013, 1014, 1016 in combination with incorporating corrective optical elements adapted to ameliorate during varied gaze directions one or more of the following type of low-order aberrations of a current user: de-focus, myopia, hyperopia, presbyopia, astigmatism (block 1041). Other exemplary process features include incorporating corrective optical elements adapted to ameliorate during varied gaze directions one or more of the following type of high-order aberrations of a current user: coma, spherical aberration, trefoil, chromatic aberration (block 1052).

Other process examples include incorporating corrective optical elements adapted to ameliorate during varied gaze directions a current user's high order aberrations corresponding to Zernike polynomials of order 3 or order 4 or order 5 or order 6 or higher (block 1053). Another example includes incorporating transformable optical elements adapted to compensate during varied gaze directions for one or more aberrations of a current user characterized by a spatially-sampled wavefront error (block 1054).

Some embodiments may include incorporating transformable optical elements configured during varied gaze directions to modify a square or hexagonal matrix of sensors or actuators which transform a deformable reflective or refractive aspect of the transformable corrective optical elements (block 1056). A further aspect may include obtaining access to information received from a wavefront detection device that directly measures optical aberrations of the particular user's vision (block 1057).

Figure 35:
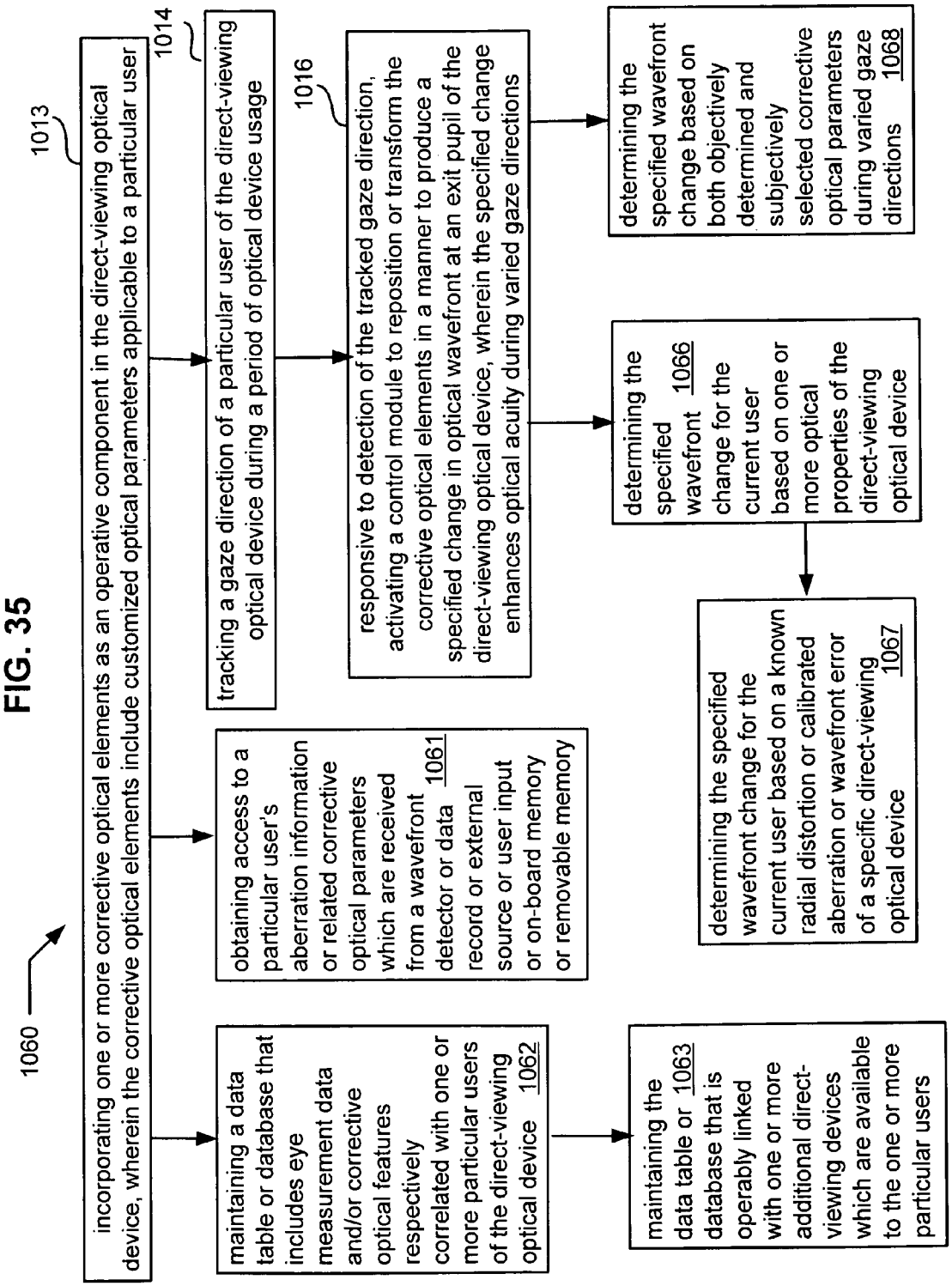

Referring to FIG. 35, exemplary embodiments may include various process operations 1060 including previously described aspects 1013, 1014, 1016 as well as obtaining access to a particular user's aberration information or related corrective optical parameters which are received from a wavefront detector or data record or external source or user input or on-board memory or removable memory (block 1061). In some instances a further aspect includes maintaining a data table or database that includes eye measurement data and/or corrective optical features respectively correlated with one or more particular users of the direct-viewing optical device (block 1062). A related aspect may include maintaining the data table or database that is operably linked with one or more additional direct-viewing devices which are available to the one or more particular users (block 1063).

Further possibilities include determining the specified wavefront change for the current user based on one or more optical properties of the direct-viewing optical device (block 1066). Related examples include determining the specified wavefront change for the current user based on a known radial distortion or calibrated aberration or wavefront error of a specific direct-viewing optical device (block 1067). An additional example includes determining the specified wavefront change based on both objectively determined and subjectively selected corrective optical parameters during varied gaze directions (block 1068).

Figure 36:
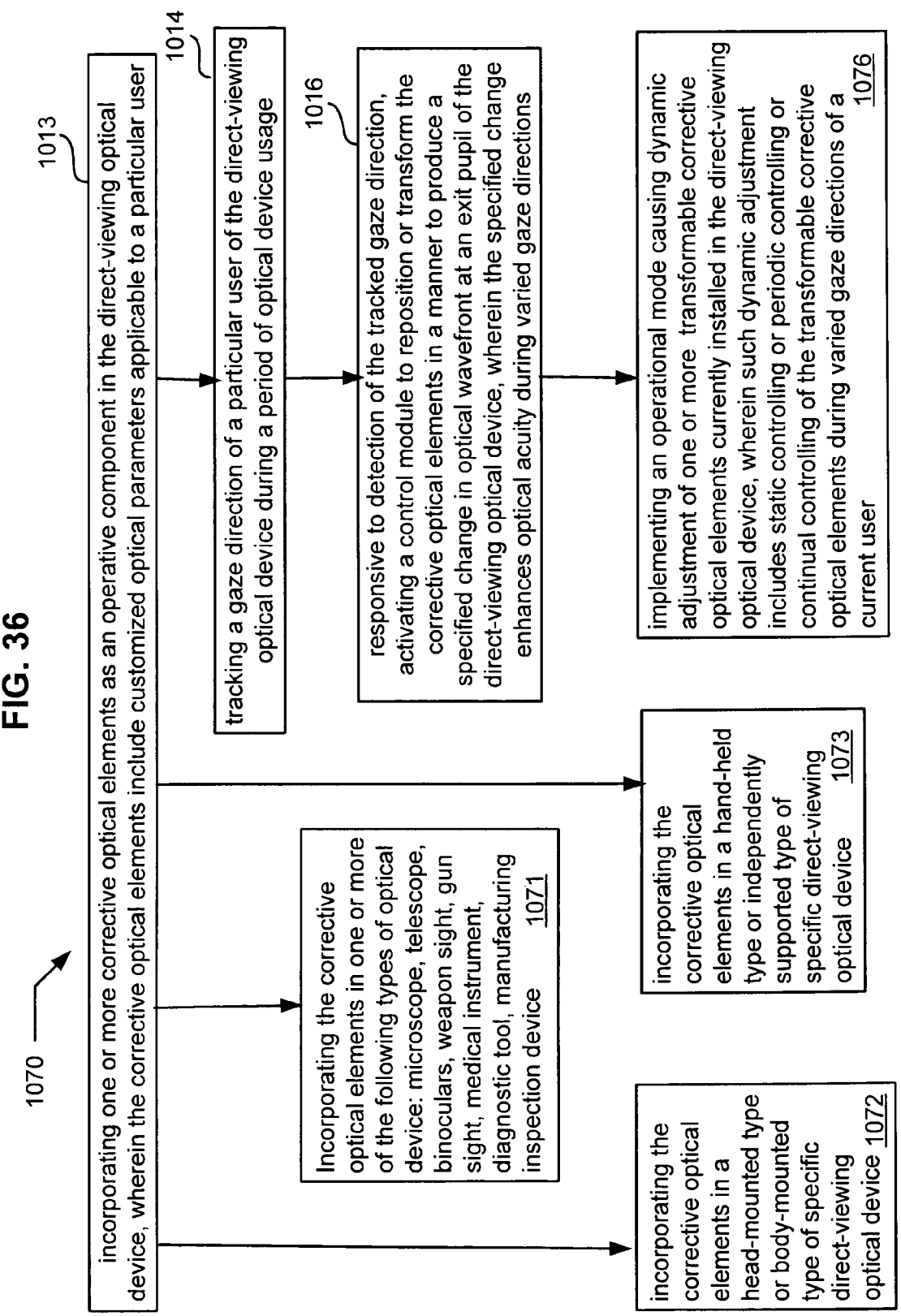

Referring to FIG. 36, various illustrated process features 1070 may be adopted including previously described aspects 1013, 1014, 1016 in combination with incorporating the corrective optical elements in one of the following types of direct-viewing optical device: microscope, telescope, binoculars, weapon sight, gun sight, medical instrument, diagnostic tool, manufacturing inspection device (block 1071). Some embodiments may include incorporating the corrective optical elements in a head-mounted type or body-mounted type of specific direct-viewing optical device (block 1072). Other examples include incorporating the corrective optical elements in a hand-held type or independently supported type of specific direct-viewing optical device (block 1073).

Further possibilities include implementing an operational mode causing dynamic adjustment of one or more transformable corrective optical elements currently installed in the direct-viewing optical device, wherein such dynamic adjustment includes static controlling or periodic controlling or continual controlling of the transformable corrective optical elements during varied gaze directions of a current user (block 1076).

Figure 37:
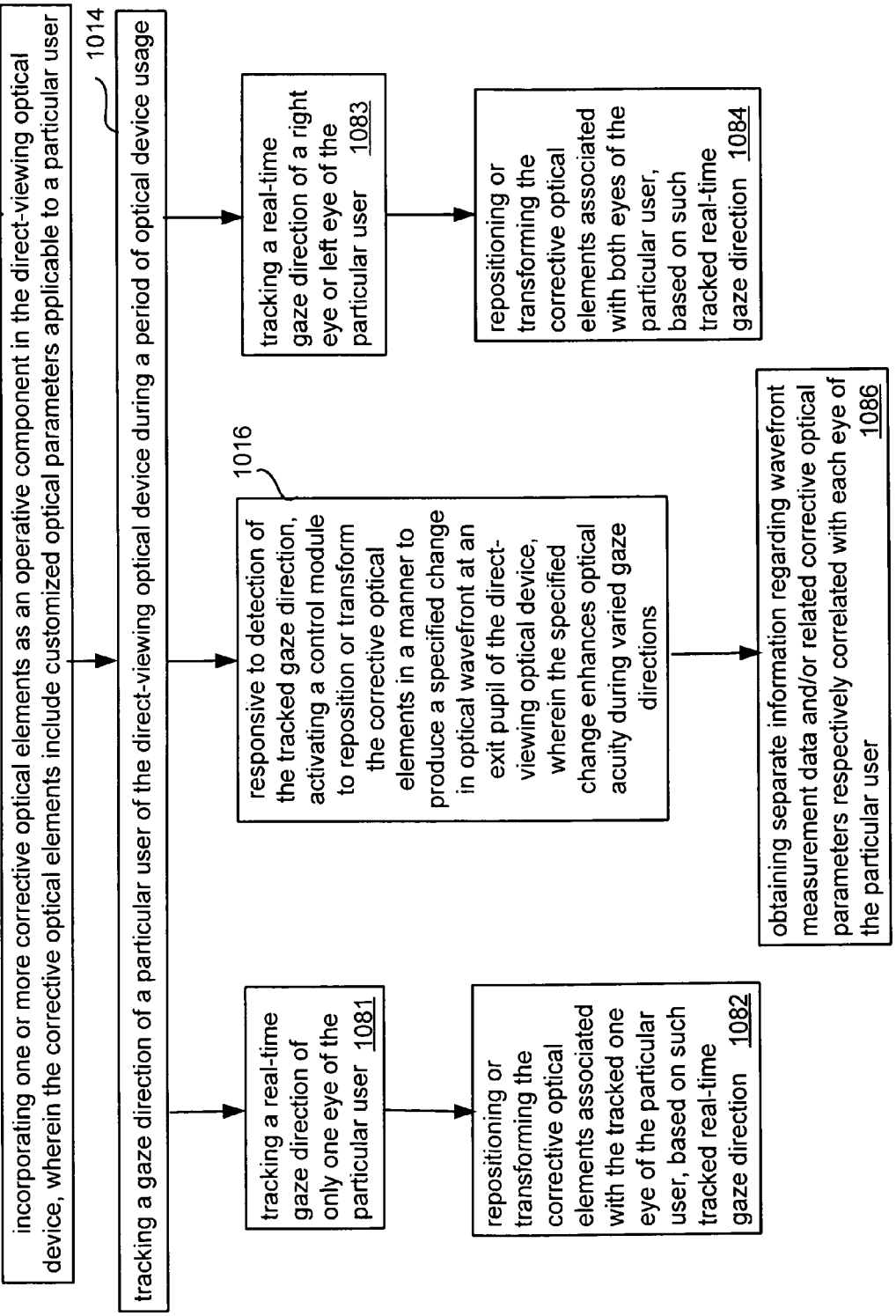

The detailed flow chart in FIG. 37 shows possible process aspects 1080 that include previously described components 1013, 1014, 1016 and also include tracking a real-time gaze direction of only one eye of the particular user (block 1081). A related aspect may include repositioning or transforming the corrective optical elements associated with the tracked one eye of the particular user, based on such tracked real-time gaze direction (block 1082).

Other possibilities include tracking a real-time gaze direction of a right eye or left eye of the particular user (block 1083), and repositioning or transforming the corrective optical elements associated with both eyes of the particular user, based on such tracked real-time gaze direction (block 1084). In some instances a further aspect may include obtaining separate information regarding wavefront measurement data and/or related corrective optical parameters respectively correlated with each eye of the particular user (block 1086).

It will be understood from the exemplary embodiments disclosed herein that numerous individual method operations depicted in the flow charts of FIGS. 31-37 can be incorporated as encoded instructions in computer readable media in order to obtain enhanced benefits and advantages.

Figure 38:
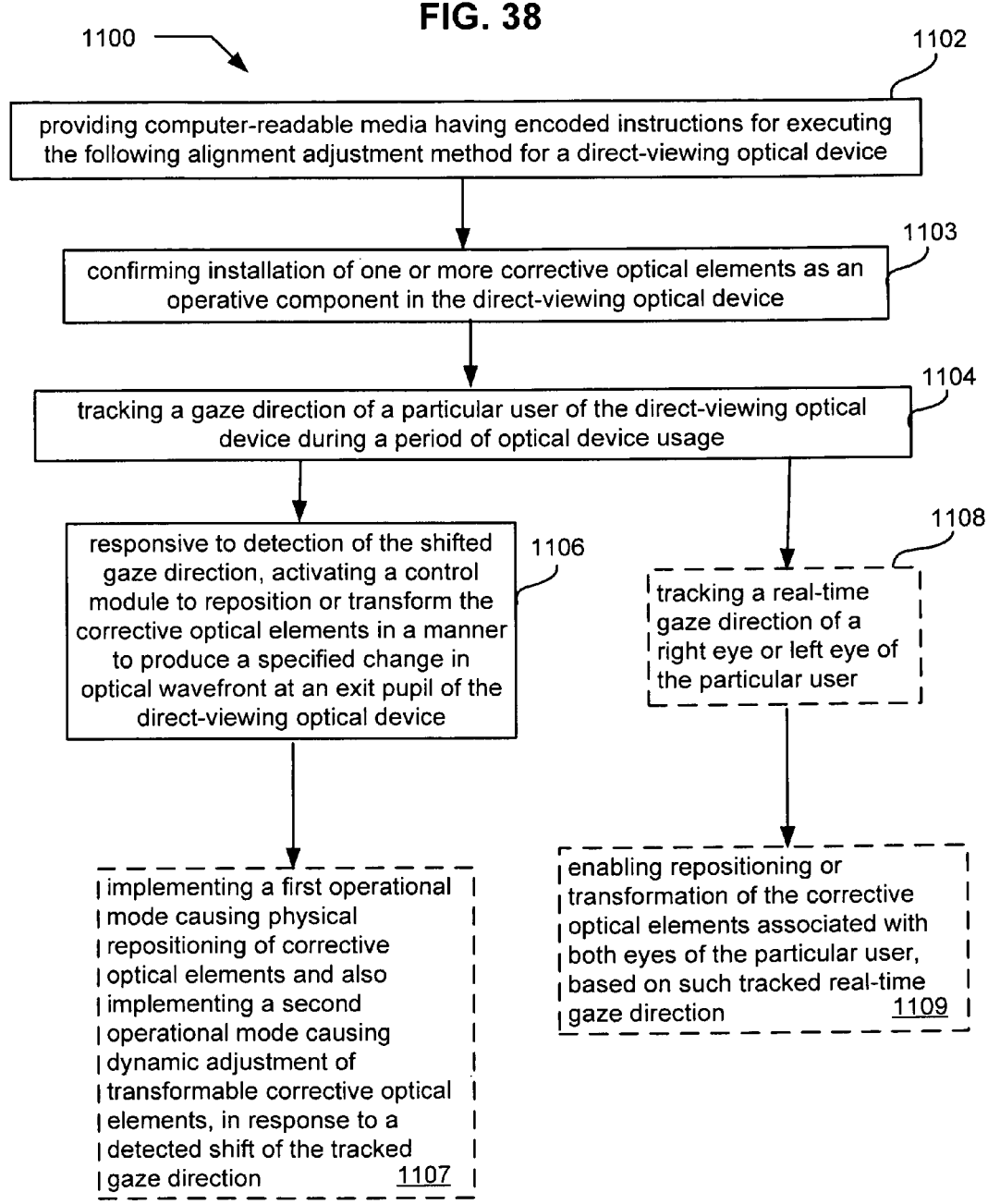
FIG. 38 is a diagrammatic flow chart for further exemplary computer-readable media embodiment features.

As another embodiment example, FIG. 38 shows a diagrammatic flow chart 1100 depicting an article of manufacture which provides computer-readable media having encoded instructions for executing an alignment adjustment method for a direct-viewing optical device (see 1102), wherein the method includes confirming installation of one or more corrective optical elements as an operative component in the direct-viewing optical device (block 1103); tracking a gaze direction of a particular user of the direct-viewing optical device during a period of optical device usage (block 1104); and responsive to detection of the shifted gaze direction, activating a control module to reposition or transform the corrective optical elements in a manner to produce a specified change in optical wavefront at an exit pupil of the direct-viewing optical device (block 1106).

Additional programmed aspects may include implementing a first operational mode causing physical repositioning of corrective optical elements and also implementing a second operational mode causing dynamic adjustment of transformable corrective optical elements, in response to a detected shift of the tracked gaze direction (block 1107). Other programmed method examples include tracking a real-time gaze direction of a right eye or left eye of the particular user (block 1108); and enabling repositioning or transformation of the corrective optical elements associated with both eyes of the particular user, based on such tracked real-time gaze direction (block 1109).

Figure 39:
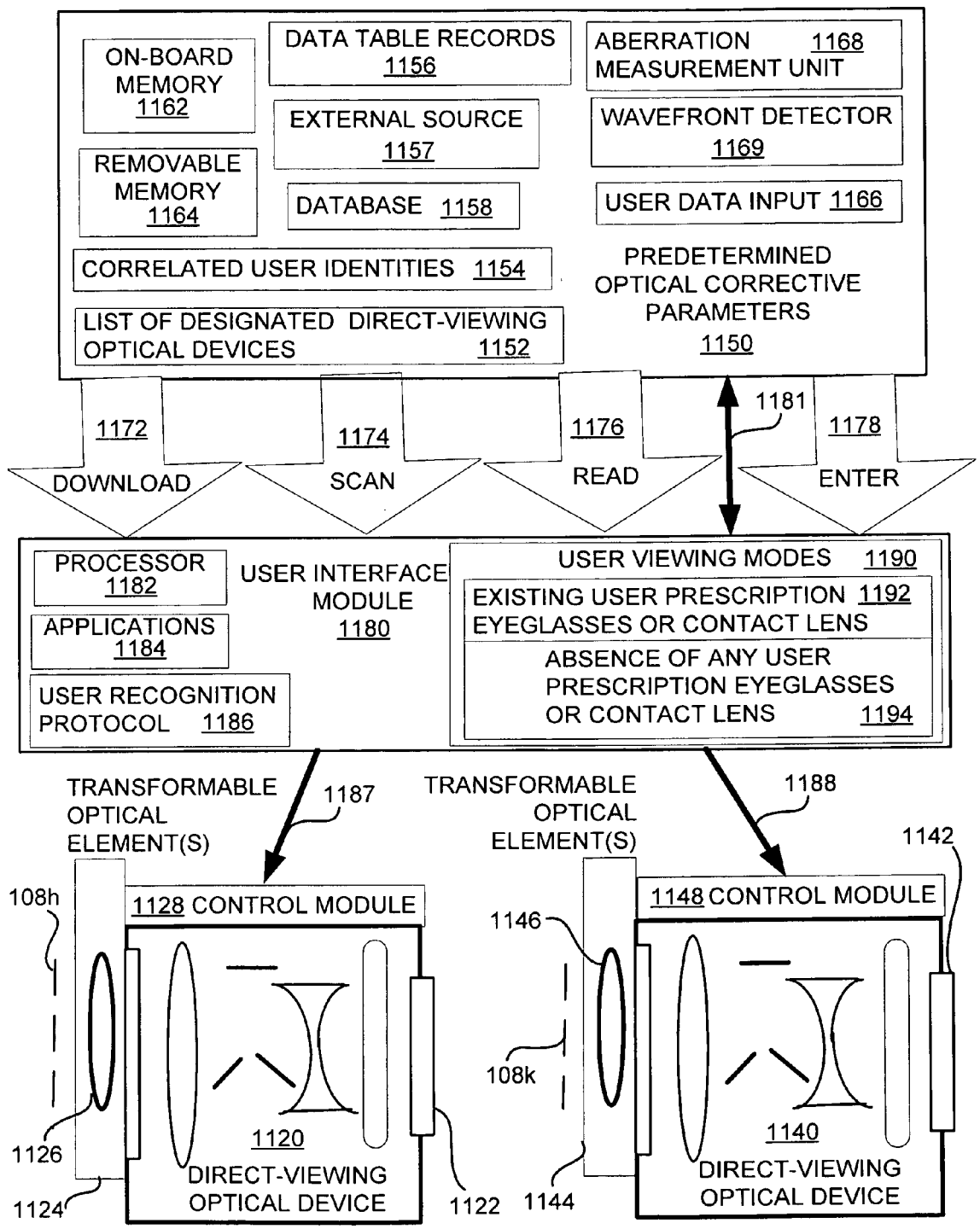
FIG. 39 is a schematic block diagram illustrating predetermined optical corrective parameters that are accessible to one or more direct-viewing optical devices.

FIG. 39 is a schematic block diagram illustrating an exemplary embodiment of a direct-viewing optical device 1120 that includes one or more types of optical elements (transmissive and/or reflective and/or refractive and/or diffractive elements shown symbolically), aperture 1122, and eyepiece component 1124 for creating an optical wavefront at an exit pupil (see representation of approximate exit plane 108*h*). A control module 1128 is operatively connected with one or more transformable elements (e.g. 1126) that are incorporated in the eyepiece component 1124.

Based on establishing an identity of a current user pursuant to a user recognition protocol 1186 for user, interface module 1180, an appropriate informational source may be accessed via communication link 1181 to obtain certain predetermined optical corrective parameters (see 1150) for a correlated user identity 1154. Some examples of such informational sources include data table records 1156, external source 1157, database 1158, as well as on-board memory 1162 and removable memory 1164. Other possible sources may include user data input 1166, wavefront detector 1169 and aberration measurement unit 1168. These examples are not intended to be exhaustive but are listed for purposes of illustration only.

A list of designated direct-viewing optical devices 1152 adapted for installation of transformable optical elements may be helpful in some embodiments to assure that additional corrective optical adjustments can take into account various types of device-based aberrations (e.g., radial distortion, calibrated aberration, wavefront error) as well as various performance viewing factors (e.g., operating condition, image property, viewing environment) for a given field of view.

The obtained predetermined optical corrective parameters 1150 can be downloaded 1172 or scanned 1174 or read 1176 or entered 1178 by circuitry or software programs (e.g., processor 1182, applications 1184) for transmittal via a communication link 1187 to control module 1128 for further processing in order to adjust the transformable optical elements 1126 to ameliorate various optical aberrations. In some instances a selection of a particular user viewing mode 1190 may be applicable for proper adjustment of the transformable optical elements 1126. For example, a selected viewing mode may already provide existing user prescription eyeglasses or contact lens 1192. As another example, a selected viewing mode may proceed based on an absence of any user prescription eyeglasses or contact lens 1194.

It will be understood that different specific direct viewing optical devices as well as different models and different types of direct-viewing optical devices may be chosen for sequential and/or concurrent use by the same approved user as well as in some instances by multiple other approved users. In that regard, user interface module 1180 may be connected via a communication link 1188 to control module 1148 that is operatively connected to one or more transformable optical elements 1146 incorporated in eyepiece component 1144 of a different direct-viewing optical device 1140 having aperture 1142 to create an optical wavefront at an exit pupil (see representation of approximate exit plane 108*k*).

It will also be understood that the predetermined optical corrective parameters 1150 may be periodically updated based on changed aberrations of an approved user, as well as in some instances based on changed aberrations of a particular direct-viewing optical device, as well as in some instances based on changed performance viewing factors of the particular direct-viewing optical device.

FIG. 40 shows representative data table records regarding predetermined optical corrective parameters for various approved users (see user ID category 1200). It may be desirable to make periodic queries to each approved user regarding ongoing preferences and changes to the various types of predetermined optical corrective parameters correlated with such approved user. Possible data categories include an approved device list 1230, and a default setting for both eyes 1240. Additional data categories may be provided for corrective parameter settings for left eye low-order aberrations 1250, right eye low-order aberrations 1260, left eye high-order aberrations 1270, and right eye high-order aberrations 1280.

It will be understood that some of these corrective parameter categories may not be applicable (N/A) to certain approved users. For example only low order aberration corrections are needed for Ron 1204 who is approved for non-precision direct viewing devices (see 1275, 1285). As another example, only high-order aberration corrections are needed for Les 1206 who always wears his low-order aberration contact lens (see 1255, 1265). As a further example, Gary 1214 only uses his "good vision" right eye for all approved direct-vision optical devices (see 1256, 1276).

Some user IDs may require additional data access via hyperlinks 1235 for respective details regarding several different direct-viewing devices. For example, see Kim 1202 with hyperlink 1235a, Ron 1204 with hyperlink 1235b, and Les 1206 with hyperlink 1235c. Similarly see Linda 1212 with hyperlink 1235d, and Gary 1214 with hyperlink 1235e.

Some users may require access to only one direct-viewing optical device (e.g. precision microscope 1237 for Chris 1216), wherein both low-order and high-order aberration corrections are separately required for each eye (see "no" default setting 1246). Another user Sid 1208 is approved for "lab only" type of direct-viewing optical devices (see 1236). Yet a further user Jan 1218 is approved for "field devices" only (see 1238). Some users such as Marge 1209 and Mort 1219 have the same aberrations for both right and left eyes, thereby having their own respective default setting for both eyes (see 1245, 1247). It will be understood that some types of direct-viewing optical devices (e.g. binoculars) are typically viewed with both eyes, while other types of direct-viewing optical devices may typically be configured for viewing by only one eye at a time.

Of course the data category examples disclosed herein (see FIG. 40) are not intended to be limiting, and are provided for purposes of illustration only. Some of the illustrated data categories may be eliminated and new categories may be added depending on the circumstances. Data searching and retrieval and related processing may be accomplished by circuitry and/or programmed software to enable real-time adjustment of transformable optical elements for a current approved user of a particular direct-viewing optical device.

Figure 41:
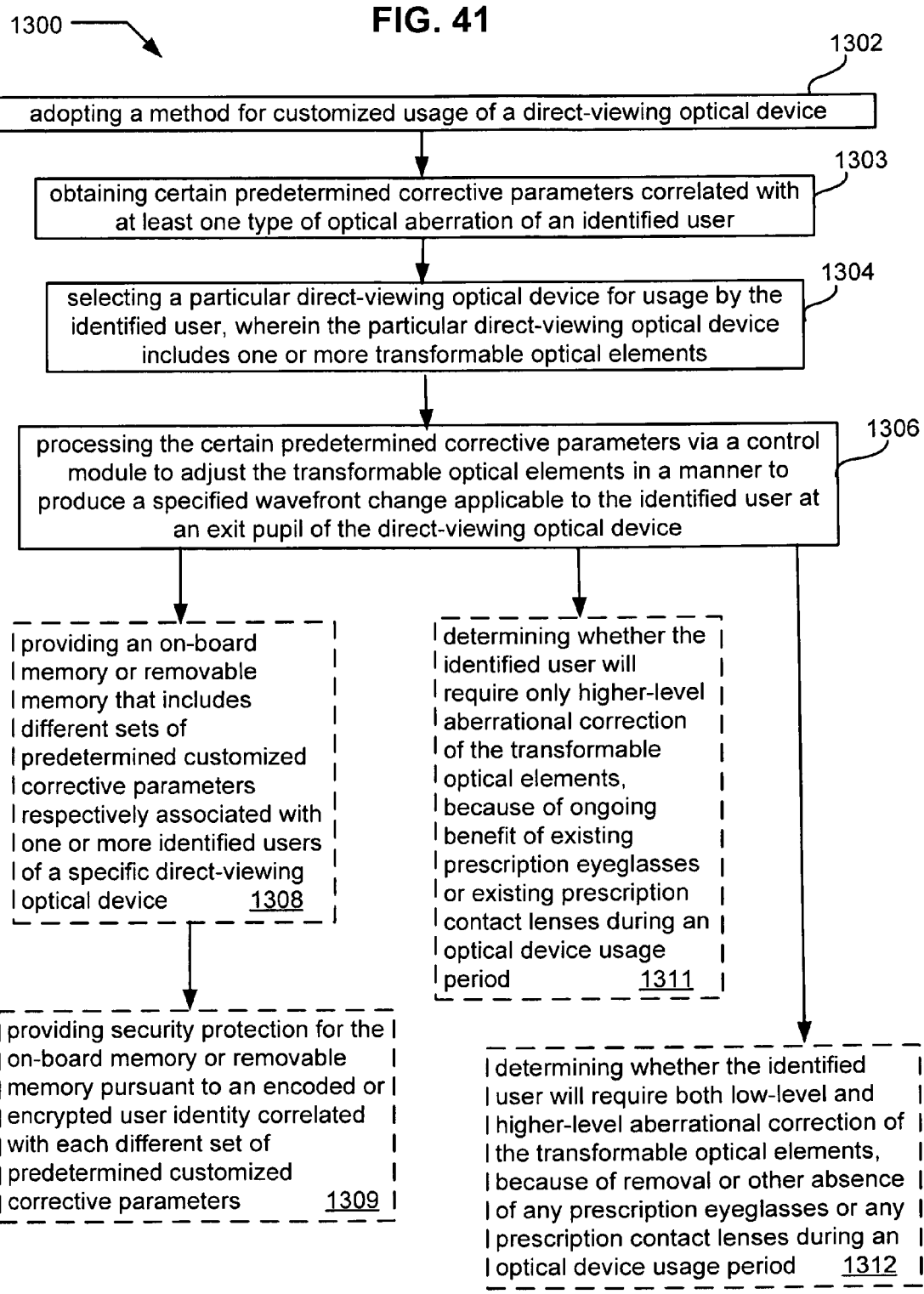
FIG. 41 is a high level flow chart showing exemplary method aspects regarding adjustment of transformable optical elements in accordance with predetermined optical corrective parameters.

Referring to the high-level flow chart of FIG. 41, various possible embodiment features 1300 are depicted in connection with adopting a method for customized usage of a direct-viewing optical device (see operation 1302). Such an exemplary method may include obtaining certain predetermined corrective parameters correlated with at least one type of optical aberration of an identified user (block 1303); selecting a particular direct-viewing optical device for usage by the identified user, wherein the particular direct-viewing optical device includes one or more transformable optical elements (block 1304); and processing the certain predetermined corrective parameters via a control module to adjust the transformable optical elements in a manner to produce a specified wavefront change applicable to the identified user at an exit pupil of the direct-viewing optical device (block 1306).

Other possible aspects include providing an on-board memory or removable memory that includes different sets of predetermined customized corrective parameters respectively associated with one or more identified users of a specific direct-viewing optical device (block 1308). Related aspects may include providing security protection for the on-board memory or removable memory pursuant to an encoded or encrypted user identity correlated with each different set of predetermined customized corrective parameters (block 1309).

Another depicted example includes determining whether the identified user will require only higher-level aberrational correction of the transformable optical elements, because of ongoing benefit of existing prescription eyeglasses or existing prescription contact lenses during an optical device usage period (block 1311). A further example includes determining whether the identified user will require both low-level and higher-level aberrational correction of the transformable optical elements, because of removal or other absence of any prescription eyeglasses or any prescription contact lenses during an optical device usage period (block 1312).

Figure 42:
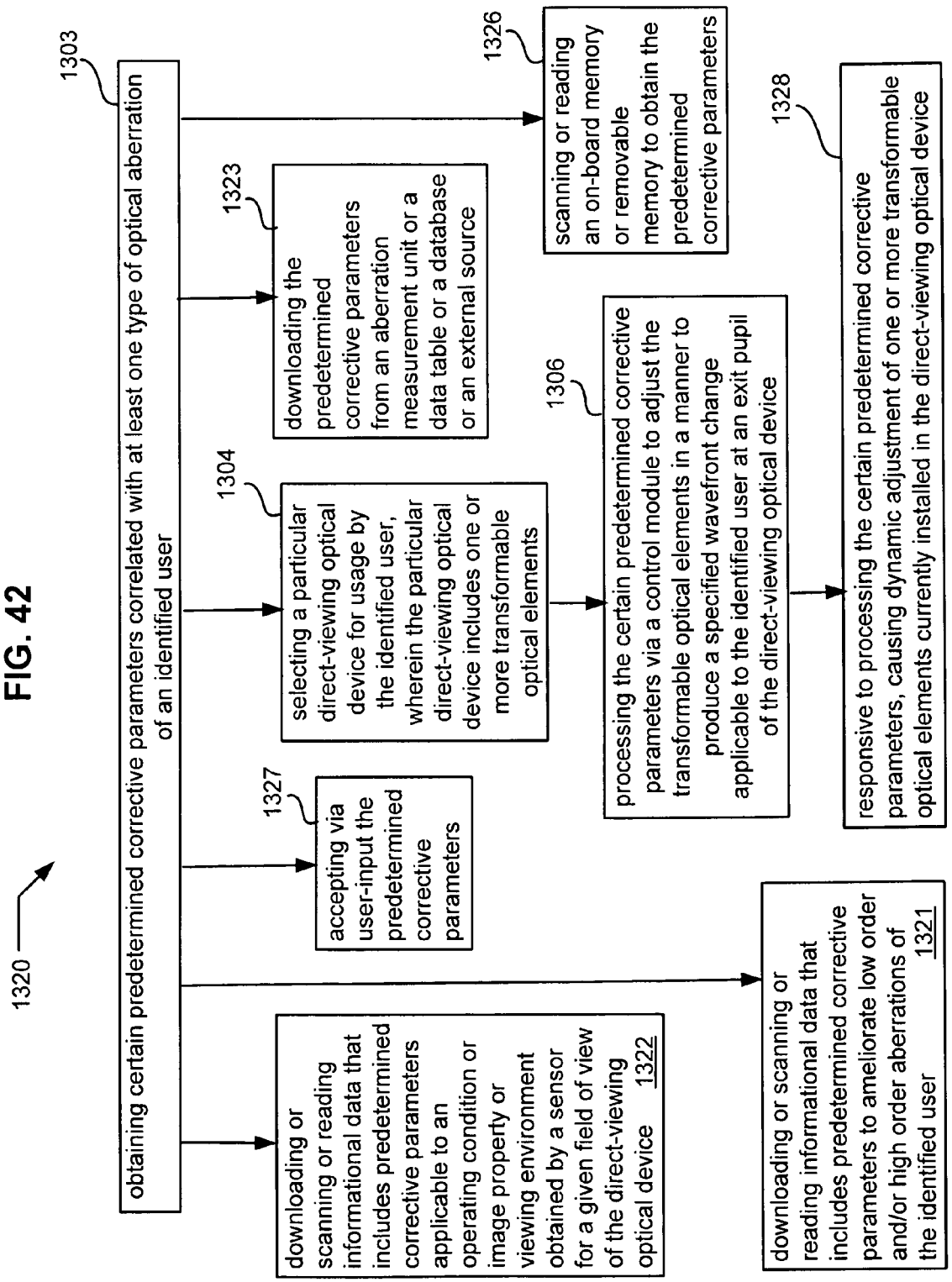

The detailed flow chart of FIG. 42 illustrates some embodiment aspects 1320 that include previously described operations 1303, 1304, 1306 in combination with downloading or scanning or reading informational data that includes predetermined corrective parameters to ameliorate low order and/or high order aberrations of the identified user (block 1321). Other possibilities include downloading or scanning or reading informational data that includes predetermined corrective parameters applicable to an operating condition or image property or viewing environment obtained by a sensor for a given field of view of the direct-viewing optical device (block 1322). In some instances a further method feature may include downloading the predetermined corrective parameters from an aberration measurement unit or a data table or a database or an external source (block 1323).

Additional depicted examples include scanning or reading an on-board memory or removable memory to obtain the predetermined corrective parameters (block 1326), and in some instances accepting via user-input the predetermined corrective parameters (block 1327). Another possible implementation aspect includes responsive to processing the certain predetermined corrective parameters, causing dynamic adjustment of one or more transformable optical elements currently installed in the direct-viewing optical device (block 1328).

Figure 43:
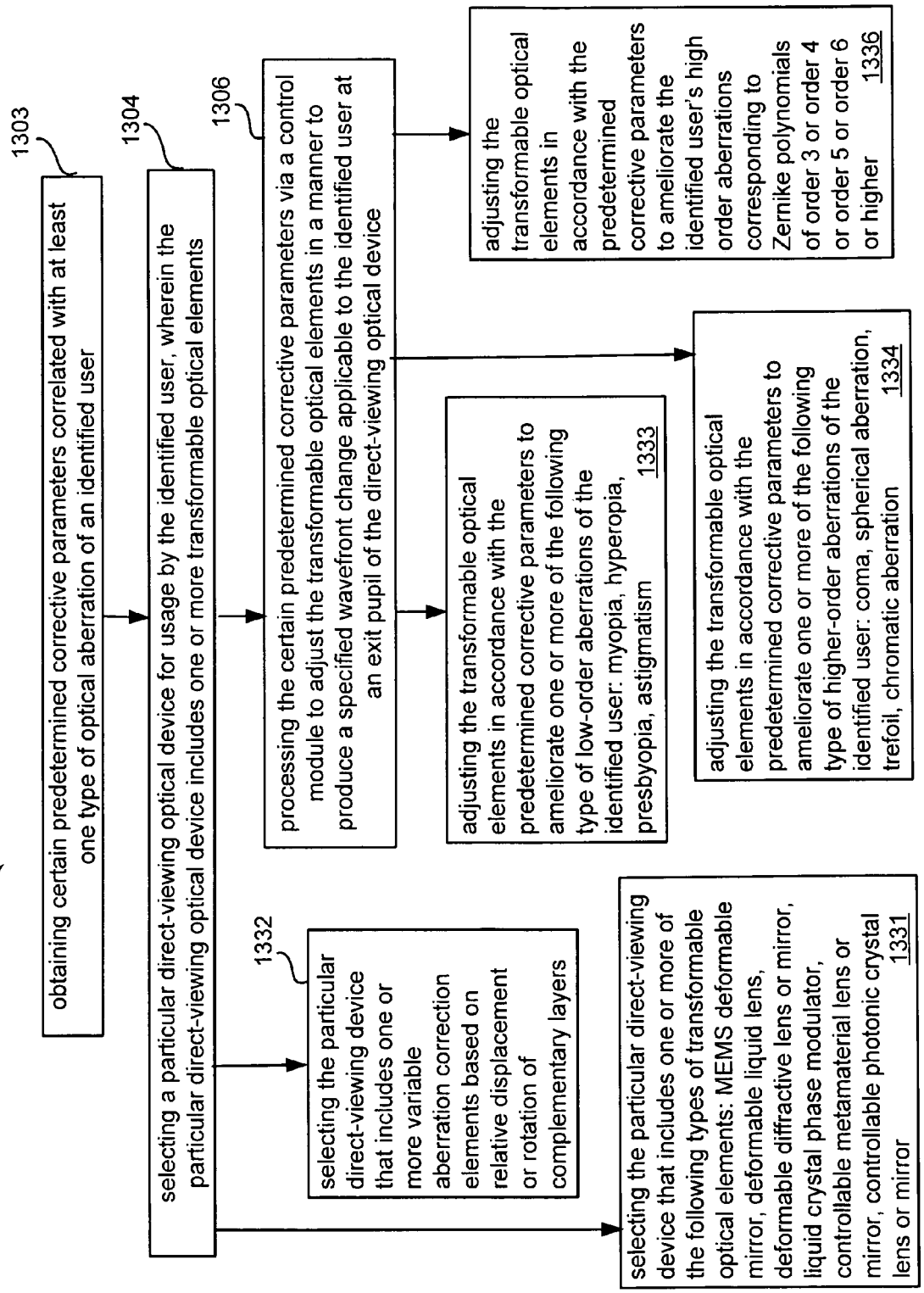

The illustrated process embodiment features 1330 shown in FIG. 43 include previously described aspects 1303, 1304, 1306 as well as selecting the particular direct-viewing device that includes one or more of the following types of transformable optical elements: MEMS deformable mirror, deformable liquid lens, deformable diffractive lens or mirror, liquid crystal phase modulator, controllable metamaterial lens or mirror, controllable photonic crystal lens or mirror (block 1331). A further example includes selecting the particular direct-viewing device that includes one or more variable aberration correction elements based on relative displacement or rotation of complementary layers (block 1332). Some embodiments may include adjusting the transformable optical elements in accordance with the predetermined corrective parameters to ameliorate one or more of the following type of low-order aberrations of the identified user: myopia, hyperopia, presbyopia, astigmatism (block 1333).

Additional possibilities include adjusting the transformable optical elements in accordance with the predetermined corrective parameters to ameliorate one or more of the following type of higher-order aberrations of the identified user: coma, spherical aberration, trefoil, chromatic aberration (block 1334). Another depicted example includes adjusting the transformable optical elements in accordance with the predetermined corrective parameters to ameliorate the identified user's high order aberrations corresponding to Zernike polynomials of order 3 or order 4 or order 5 or order 6 or higher (block 1336).

Figure 44:
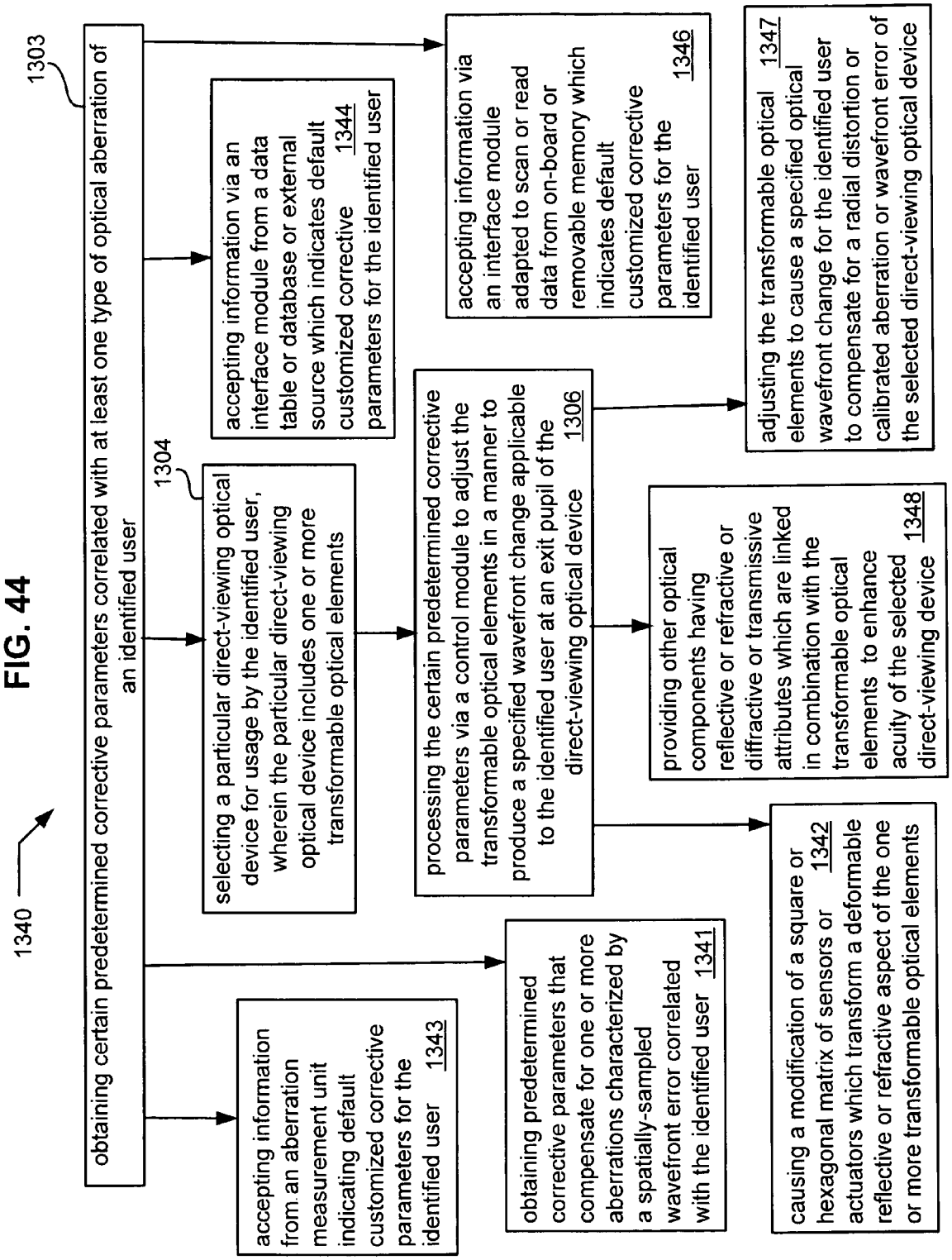

Referring to illustrated aspects 1340 shown in FIG. 44, some implementation aspects may include previously described method features 1303, 1304, 1306 in combination with obtaining predetermined corrective parameters that compensate for one or more aberrations characterized by a spatially-sampled wavefront error correlated with the identified user (block 1341). Yet another possibility includes causing a modification of a square or hexagonal matrix of sensors or actuators which transform a deformable reflective or refractive aspect of the one or more transformable optical elements (block 1342). Some embodiments may include accepting information from an aberration measurement unit indicating default customized corrective parameters for the identified user (block 1343).

An additional enhancement feature may include accepting information via an interface module from a data table or database or external source which indicates default customized corrective parameters for the identified user (block 1344). A further aspect may include accepting information via an interface module adapted to scan or read data from on-board or removable memory which indicates default customized corrective parameters for the identified user (block 1346).

Also shown in FIG. 44 are other exemplary process operations including adjusting the transformable optical elements to cause a specified optical wavefront change for the identified user to compensate for a radial distortion or calibrated aberration or wavefront error of the selected direct-viewing optical device (block 1347). Some embodiments may also include providing other optical components having reflective or refractive or diffractive or transmissive attributes which are linked in combination with the transformable optical elements to enhance acuity of the selected direct-viewing device (block 1348).

Figure 45:
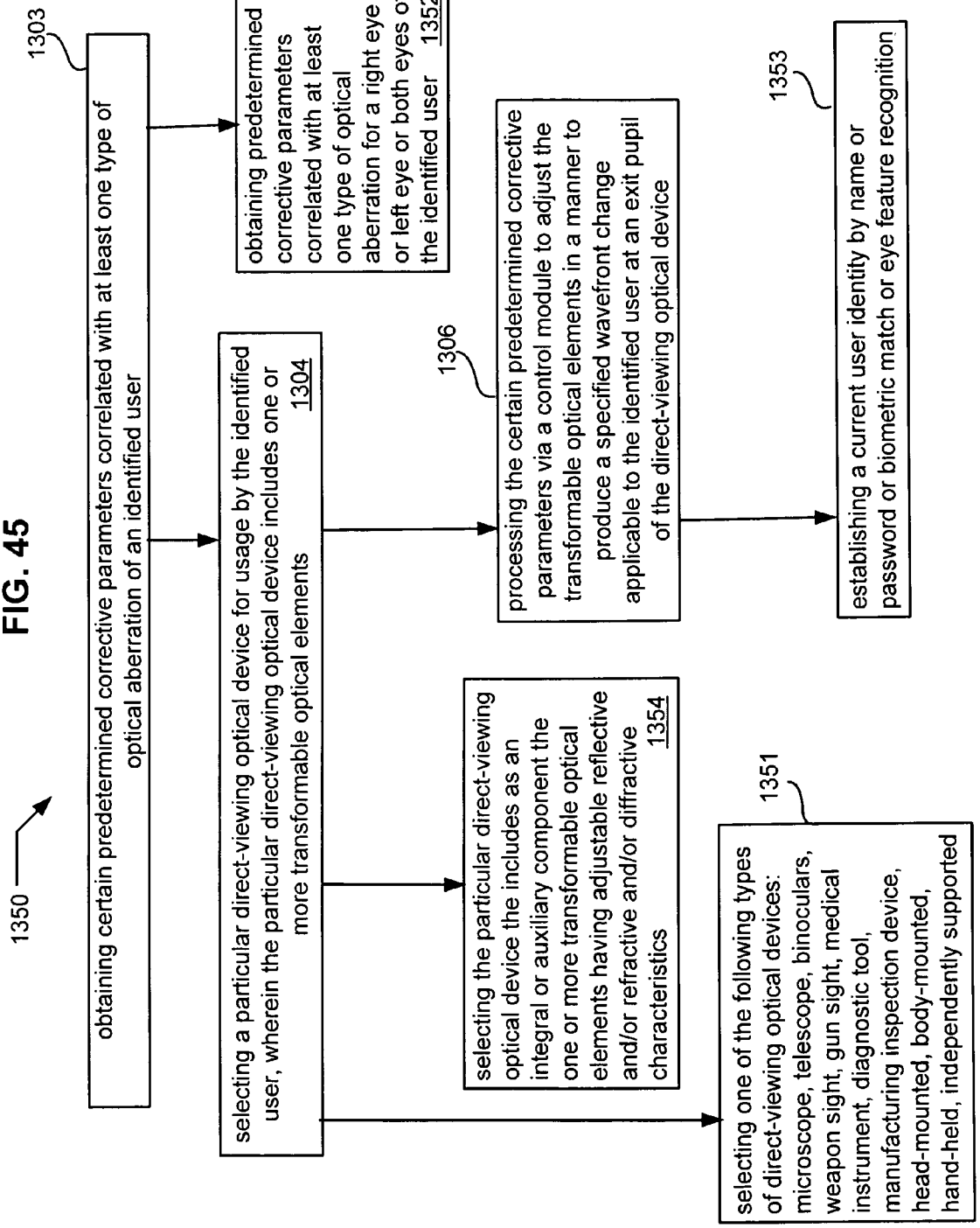

FIG. 45 is a detailed flow chart showing possible aspects 1350 such as previously described method features 1303, 1304, 1306 as well as selecting one of the following types of direct-viewing optical devices: microscope, telescope, binoculars, weapon sight, gun sight, medical instrument, diagnostic tool, manufacturing inspection device, head-mounted, body-mounted, hand-held, independently supported (block 1351). Another feature includes obtaining predetermined corrective parameters correlated with at least one type of optical aberration for a right eye or left eye or both eyes of the identified user (block 1352).

Additional illustrated examples include establishing a current user identity by name or password or biometric match or eye feature recognition (block 1353). Other possibilities include selecting the particular direct-viewing optical device that includes as an integral or auxiliary component the one or more transformable optical elements having adjustable reflective and/or refractive and/or diffractive characteristics (block 1354).

Figure 46:
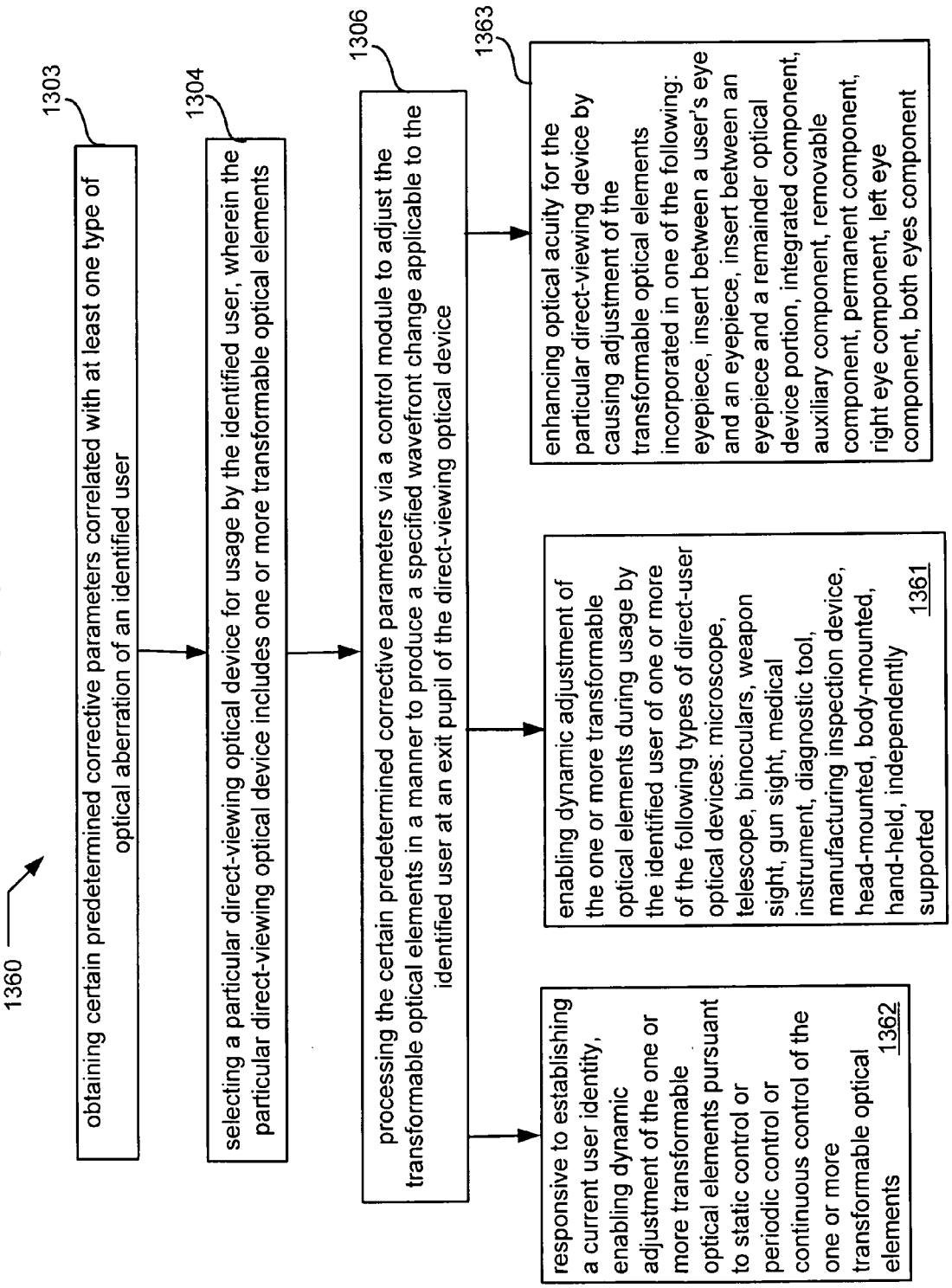

The illustrated aspects 1360 of FIG. 46 include previously described operations 1303, 1304, 1306 that may be combined with enabling dynamic adjustment of the one or more transformable optical elements during usage by the identified user of one or more of the following types of direct-user optical devices: microscope, telescope, binoculars, weapon sight, gun sight, medical instrument, diagnostic tool, manufacturing inspection device, head-mounted, body-mounted, hand-held, independently supported (block 1361). Other enhancements may include responsive to establishing identity of a current user, enabling dynamic adjustment of the one or more transformable optical elements pursuant to static control or periodic control or continuous control of the one or more transformable optical elements (block 1362). A further illustrated example includes enhancing optical acuity for the particular direct-viewing device by causing adjustment of the transformable optical elements incorporated in one of the following: eyepiece, insert between a user's eye and an eyepiece, insert between an eyepiece and a remainder optical device portion, integrated component, auxiliary component, removable component, permanent component, right eye component, left eye component, both eyes component (block 1363).

It will be understood from the various embodiments disclosed herein that many individual method operations depicted in the flow charts of FIGS. 41-46 can be incorporated as encoded instructions in computer readable media in order to obtain enhanced benefits and advantages.

As a further embodiment example, FIG. 47 shows a diagrammatic flow chart 1370 depicting an article of manufacture which provides computer-readable media having encoded instructions for executing a method for customized usage of a direct-viewing optical device (see 1371), wherein the method includes obtaining certain predetermined corrective parameters correlated with at least one type of optical aberration of an identified user (block 1372); activating a communication link to make the obtained predetermined corrective parameters accessible to a particular direct-viewing optical device that includes one or more transformable optical elements (block 1373); and processing the certain predetermined corrective parameters via a control module to adjust the transformable optical elements in a manner to produce a specified wavefront change applicable to the identified user at an exit pupil of the direct-viewing optical device (block 1374).

Other possible programmed aspects include enabling operative usage of the particular direct-viewing device that includes other optical components having reflective or refractive or diffractive or transmissive attributes which facilitate enhanced acuity of the selected direct-viewing device in combination with the transformable optical elements (block 1376). Another programmed example includes activating the communication link with the particular direct-viewing optical device that includes one or more transformable optical elements having adjustable reflective and/or refractive and/or diffractive characteristics (block 1377).

In some programmed embodiments, an exemplary method aspect may include enhancing optical acuity for the particular direct-viewing device by causing adjustment of the transformable optical elements incorporated in one of the following: eyepiece, insert between a user's eye and an eyepiece, insert between an eyepiece and a remainder optical device portion, integrated component, auxiliary component, removable component, permanent component, right eye component, left eye component, both eyes component (block 1377).

FIG. 48 shows representative data records for various types of prefabricated corrective optical elements associated with one or more approved users (see listing of user identities 1400). Possible category types of prefabricated corrective optical elements include disposable 1430, transformable or rewritable 1440, and recyclable 1450. Additional category types may include corrective parameters for "high-order only" aberrations (see 1460), or for both "low-order & high-order" aberrations (see 1470). Other possible category types include prefabricated corrective optical elements adapted for "only one device type or model" (see 1480), or adapted for "multiple acceptable devices" (see 1490).

It will be understood that some approved users may be associated with several different prefabricated corrective optical elements that are available for possible present and/or future use, while others may be associated with only a single prefabricated corrective optical element available for possible present and/or future use. For example, an approved user John has three user identities (John #00, John #11, John #22) that are each respectively associated with a different prefabricated corrective optical element. The first optical element (see 1402) is recyclable 1452 and corrects both low-order and high-order aberrations 1472 during usage by John in multiple acceptable devices 1491. A hyperlink 1492 enables access to additional informational data and usage guidelines, etc. for each of the multiple acceptable devices 1491.

The second optical element (see 1404) is adapted to be transformable or rewriteable 1442 and corrects high-order aberrations 1462 during installed usage by John in a specified device type or model 1481. A hyperlink 1482 enables access to additional informational data and usage guidelines, etc. for the specified direct-viewing optical device. The third optical element (see 1406) is recyclable and corrects both low-order and high-order aberrations 1474 during installed usage by John in a different specified device type or model 1484. A separate hyperlink is provided to enable access to pertinent data and guidelines for the specified device type or model 1484.

Another illustrated example indicates that an approved user Karl has two user identities (Karl #00, Karl #11) that are each respectively associated with a different prefabricated corrective optical corrective element. The first optical element (see 1409) is transformable or rewritable 1444 and corrects both low-order and high-order aberrations 1477 during usage by Karl in multiple acceptable devices 1494. The second optical element (see 1412) is recyclable 1458 and corrects high-order aberrations 1464 during installed usage by Karl in a specified device type or model 1486. Separate hyperlinks are enabled to provide pertinent data and guidelines respectively for the multiple acceptable devices 1494 and the one specified type or model 1486.

A further illustrated example indicates that an approved user Ana has two user identities (Ana #00, Ana #11) that are each respectively associated with a different prefabricated corrective optical corrective element. The first optical element (see 1414) is recyclable 1459 and corrects both low-order and high-order aberrations 1478 during usage by Ana in multiple acceptable devices 1496. The second optical element (see 1416) is disposable 1432 and corrects high-order aberrations 1465 during installed usage by Ana in a specified device type or model 1488. Separate hyperlinks are enabled to provide pertinent data and guidelines respectively for the multiple acceptable devices 1496 and the one specified type or model 1488.

As another example, an approved user Josh has a single user identity 1408 associated with an optical element that is recyclable 1456 and corrects both low-order and high-order aberrations 1476 during installed usage by Josh in multiple acceptable devices 1493. As a further example, an approved user Mira has a single user identity 1418 associated with an optical element that is transformable or rewritable 1446 and corrects only high-order aberrations 1466 during installed usage by Mira in multiple acceptable devices 1497. As a further example, an approved visitor has a single user identity 1419 associated with an optical element that is disposable 1434 and corrects both low-order and high-order aberrations 1479 during installed usage by the visitor in multiple acceptable devices 1498. Separate hyperlinks are enabled to provide pertinent data and guidelines for the respective multiple acceptable devices approved for Josh, Mira, and the visitor.

Of course the disclosed data record examples of FIG. 48 are for purposes of illustration only and are not intended to be limiting. Some of the data categories may be eliminated and other categories may be added depending on the circumstances.

Figure 49:
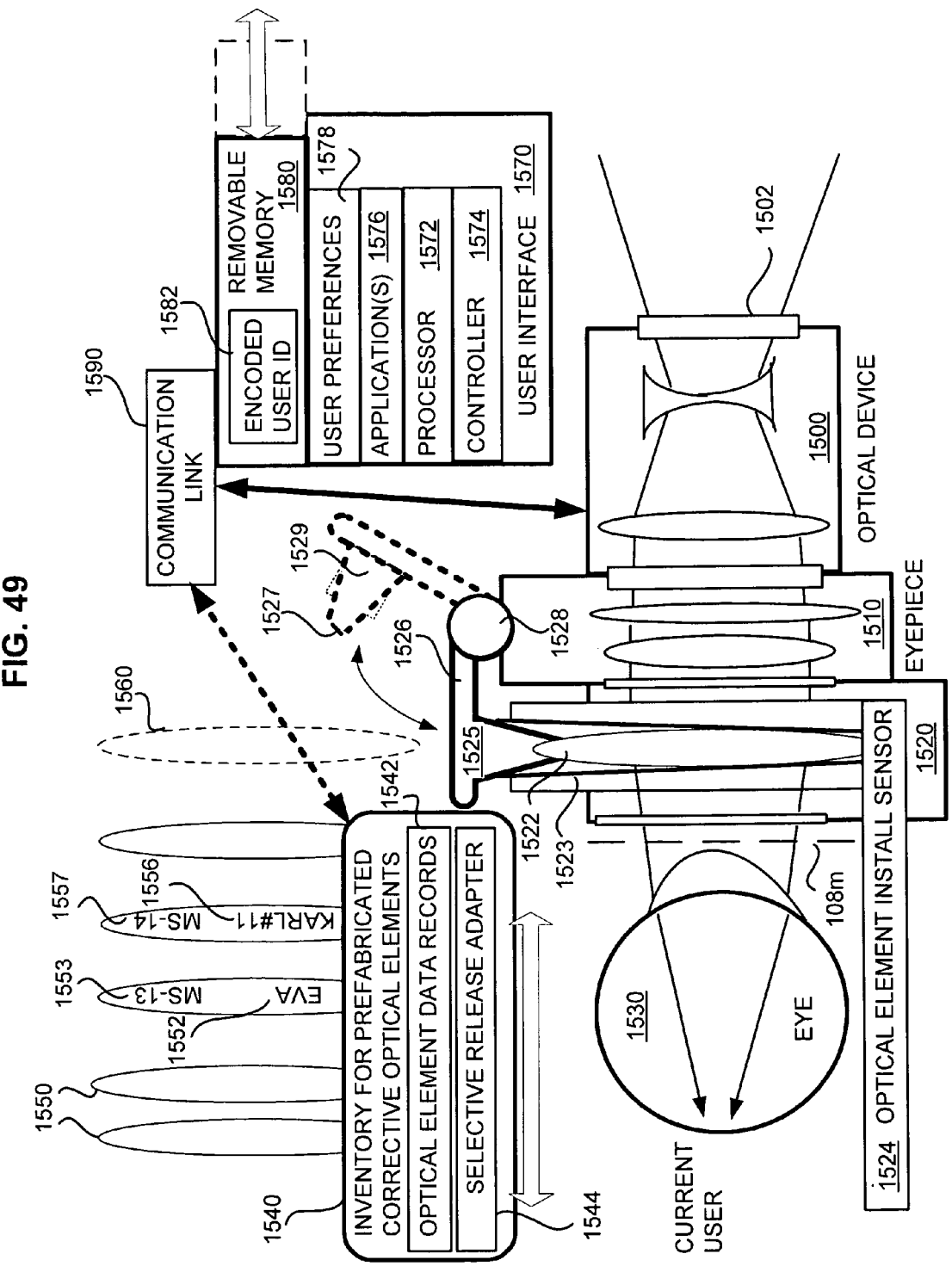
FIG. 49 is a schematic block diagram illustrating embodiment features incorporated in an exemplary inventory system for prefabricated corrective optical elements.

FIG. 49 is a schematic block diagram illustrating various exemplary embodiment features regarding a direct-viewing optical device 1500 that includes aperture 1502, eyepiece 1510, and component 1520 configured to receive an interchangeable optical element 1522 that creates an optical wavefront at an exit pupil (see representation of approximate exit plane 108*m*). The interchangeable optical element 1522 is prefabricated to include corrective optical parameters that ameliorate aberrations associated with a current user's eye 1530. An optical element sensor 1524 is adapted to determine whether interchangeable optical element 1522 is installed or withdrawn from a mounting receptacle 1523 in component 1520.

The exemplary mounting receptacle 1523 includes an inner wall having a size and/or shape adapted to receive a matching definitive exterior casing or frame of the interchangeable optical element 1522. The illustrated latching mechanism 1525 includes a lever arm 1526 attached through a pivotal base 1528 to the eyepiece 1510 to facilitate manual or automated movement between an open position (shown in phantom 1529) and a closed position (e.g., spring-loaded) where a cap portion 1527 securely holds the interchangeable optical element 1522 for optimum optical viewing alignment. Other types of latching mechanisms (e.g., magnetic, friction-fit, etc.) may be incorporated in component 1520 in a manner to achieve secure installation without interference with normal operation and usage of the direct-viewing optical device 1500.

Some embodiments include an inventory unit (see 1540) for safekeeping of various types of interchangeable optical elements 1550, 1553, 1557 respectively correlated with approved users of the optical device 1500. Each interchangeable optical element may include detectable reference indicia or individualized marking 1552, 1556 correlated with an approved user (e.g. Eva) or a user identity (e.g., Karl #11). In some instances each interchangeable optical element may further include detectable reference indicia or individualized marking 1553, 1557 correlated with one or more associated direct-viewing devices such as a microscope (e.g., MS-13) or a different microscope (e.g., MS-14). Of course the reference indicia or individualized marking may be recognizable or detectable by unaided vision, or perhaps miniaturized or encoded or machine readable depending on the nature of the device or usage guidelines or security environment.

Accessible optical element data records 1542 (e.g., see FIG. 48) may be included with the inventory unit 1540. When the inventory unit 1540 is moved (see directional arrow) to an unload position relative to component 1520, a selective release adapter 1544 may be activated for manual or automated transfer and installation of an interchangeable optical element that is vertically positioned (see optical element shown in phantom 1560) above the mounting receptacle 1523.

In order to facilitate coordinated maintenance, selection, installation and withdrawal of various prefabricated corrective optical elements, a wireless or wired communication link 1590 may be provided from a user interface 1520 to the optical device 1500 as well as to the inventory unit 1540. The exemplary user interface 1520 includes processor 1572, controller 1574, one or more program applications 1576 as well as a record of user preferences 1578 regarding usage of the various prefabricated corrective optical elements 1550, 1553, 1557, 1560, 1522. The user interface 1570 may also be adapted to receive removable memory 1580 that could include updated informational data as well as an encoded user ID 1582 for establishing an identity confirmation of an approved user who is interested in using the direct-viewing optical device 1500.

Figure 50:
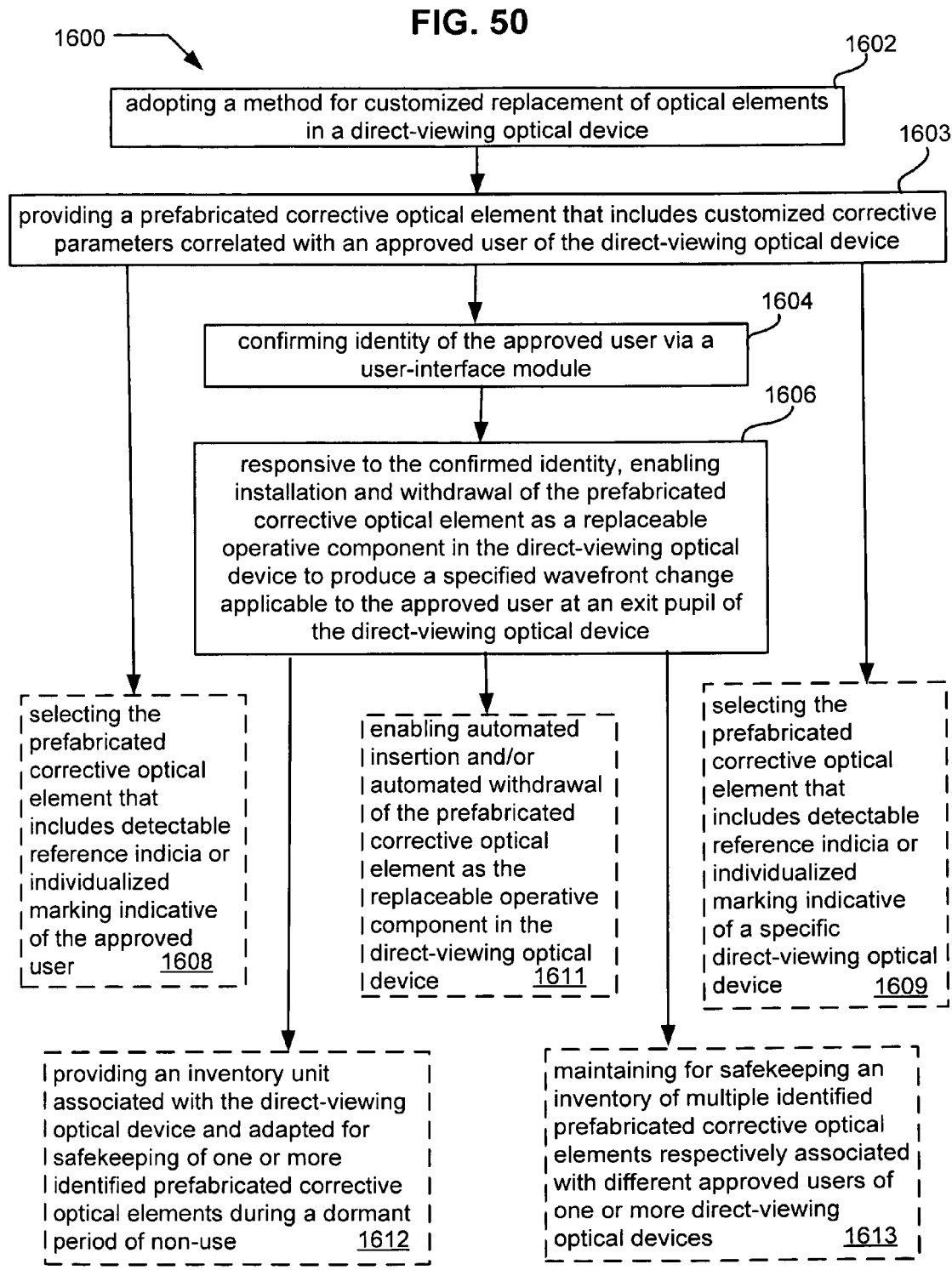
FIG. 50 is a high level flow chart that shows exemplary method aspects for incorporating prefabricated corrective optical elements in a direct-viewing optical device.

The high level flow chart of FIG. 50 depicts possible embodiment features 1600 regarding adoption of a method for customized replacement of optical elements in a direct-viewing optical device (block 1602) that includes providing a prefabricated corrective optical element that includes customized corrective parameters correlated with an approved user of the direct-viewing optical device (block 1603), and confirming identity of the approved user via a user interface module (block 1604). A further process feature responsive to the confirmed identity includes enabling installation and withdrawal of the prefabricated corrective optical element as a replaceable operative component in the direct-viewing optical device to produce a specified wavefront change applicable to the approved user at an exit pupil of the direct-viewing optical device (block 1606).

Additional exemplary aspects include selecting the prefabricated corrective optical element that includes a definitive external size and/or shape corresponding to a mounting receptacle of a specific direct-viewing optical device (block 1608). A further possible aspect include selecting the prefabricated corrective optical element that includes detectable reference indicia or individualized marking indicative of the approved user (block 1609). Some implementations may also include enabling automated insertion and/or automated withdrawal of the prefabricated corrective optical element as the replaceable operative component in the direct-viewing optical device (block 1611).

Yet another possibility includes providing an inventory unit associated with the direct-viewing optical device and adapted for safekeeping of one or more identified prefabricated corrective optical elements during a dormant period of non-use (block 1612). In some instances an embodiment may include maintaining for safekeeping an inventory of multiple identified prefabricated corrective optical elements respectively associated with different approved users of one or more direct-viewing optical devices (block 1613).

Figure 51:
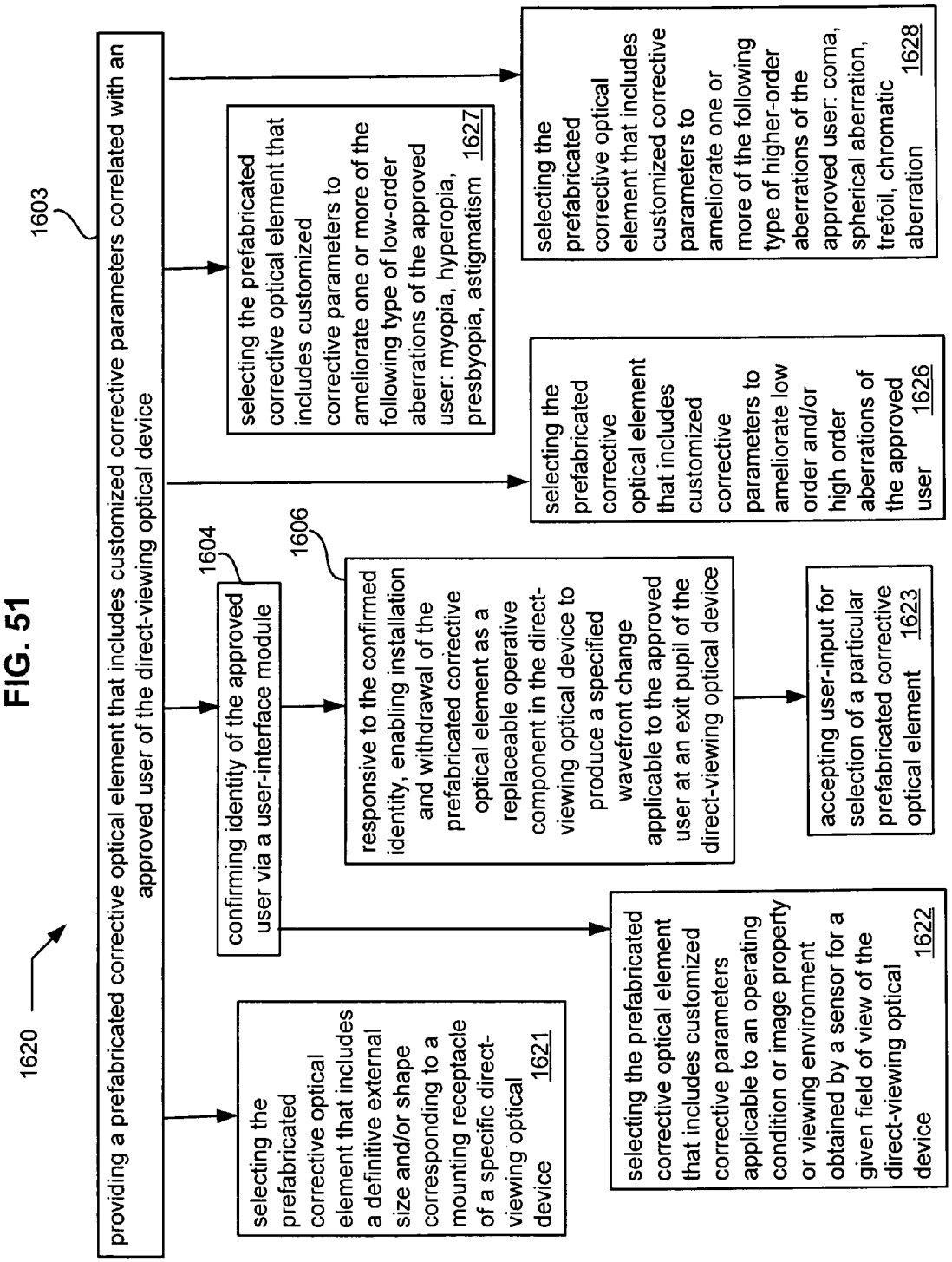
FIGS. 51-57 are detailed flow charts illustrating further exemplary method aspects for usage of interchangeable corrective optical elements in a direct-viewing optical device.

Referring to the detailed flow chart of FIG. 51, various process aspects 1620 may include previously described operations 1603, 1604, 1606 as well as selecting the prefabricated corrective optical element that includes a definitive external size and/or shape corresponding to a mounting receptacle of a specific direct-viewing optical device (block 1621). Other process aspects include selecting the prefabricated corrective optical element that includes customized corrective parameters applicable to an operating condition or image property or viewing environment obtained by a sensor for a given field of view of the direct-viewing optical device (block 1622). An additional process feature may include accepting user-input for selection of a particular prefabricated corrective optical element (block 1623).

Further possible enhancements include selecting the prefabricated corrective optical element that includes customized corrective parameters to ameliorate low order and/or high order aberrations of the approved user (block 1626), and may further include selecting the prefabricated corrective optical element that includes customized corrective parameters to ameliorate one or more of the following type of low-order aberrations of the approved user: myopia, hyperopia, presbyopia, astigmatism (block 1627). Some embodiments may include selecting the prefabricated corrective optical element that includes customized corrective parameters to ameliorate one or more of the following type of higher-order aberrations of the approved user: coma, spherical aberration, trefoil, chromatic aberration (block 1628).

Figure 52:
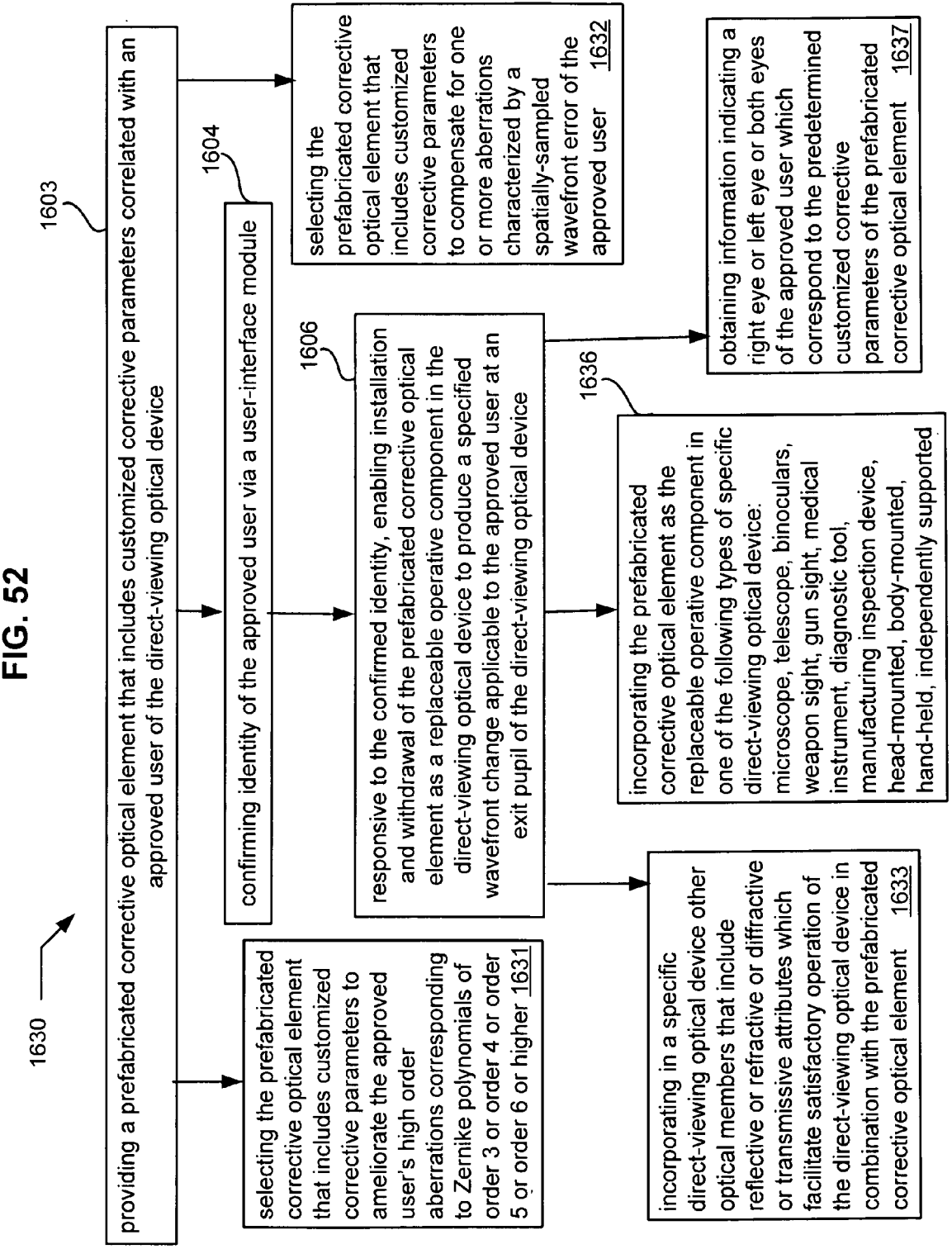

The detailed flow chart of FIG. 52 depicts exemplary process features 1630 such as previously described aspects 1603, 1604, 1606 combined with selecting the prefabricated corrective optical element that includes customized corrective parameters to ameliorate the approved user's high order aberrations corresponding to Zernike polynomials of order 3 or order 4 or order 5 or order 6 or higher (block 1631). Another depicted process feature includes selecting the prefabricated corrective optical element that includes customized corrective parameters to compensate for one or more aberrations characterized by a spatially-sampled wavefront error of the approved user (block 1632). Some exemplary aspects may include incorporating in a specific direct-viewing optical device other optical members that include reflective or refractive or diffractive or transmissive attributes which facilitate satisfactory operation of the direct-viewing optical device in combination with the prefabricated corrective optical element (block 1633).

Additional possibilities include incorporating the prefabricated corrective optical element as the replaceable operative component in one of the following types of specific direct-viewing optical device: microscope, telescope, binoculars, weapon sight, gun sight, medical instrument, diagnostic tool, manufacturing inspection device, head-mounted, body-mounted, hand-held, independently supported (block 1636). Yet other embodiments may include obtaining information indicating a right eye or left eye or both eyes of the approved user which correspond to the predetermined customized corrective parameters of the prefabricated corrective optical element (block 1637).

Figure 53:
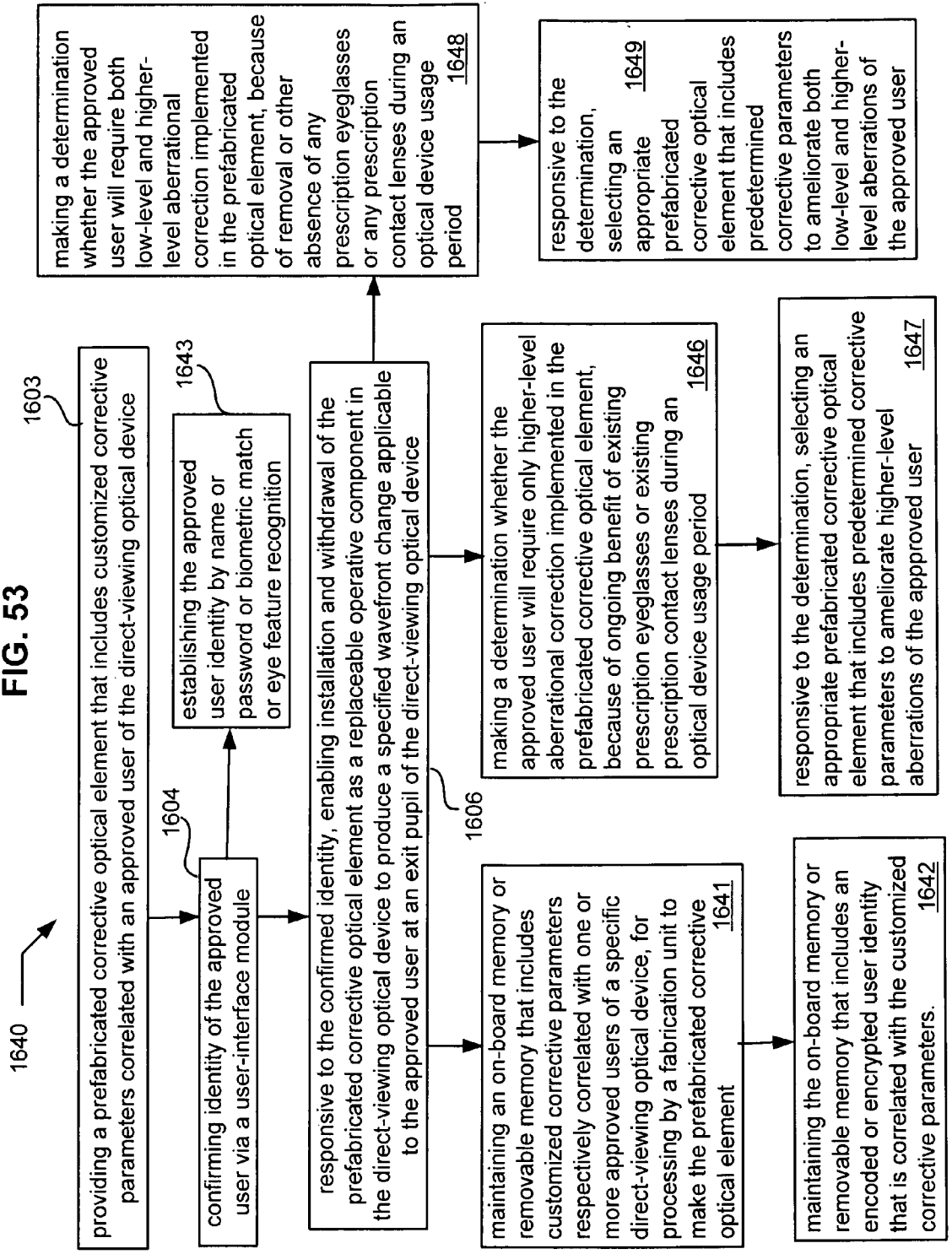

Referring to FIG. 53, various illustrated flow chart aspects 1640 include previously described operations 1603, 1604, 1606 along with maintaining an on-board memory or removable memory that includes customized corrective parameters respectively correlated with one or more approved users of a specific direct-viewing optical device, for processing by a fabrication unit to make the prefabricated corrective optical element (block 1641). A related aspect may include maintaining the on-board memory or removable memory that includes an encoded or encrypted user identity that is correlated with the customized corrective parameters (block 1642).

Other exemplary process aspects include establishing the approved user identity by name or password or biometric match or eye feature recognition (block 1643). A further possible aspect includes making a determination whether the approved user will require only higher-level aberrational correction implemented in the prefabricated corrective optical element, because of ongoing benefit of existing prescription eyeglasses or existing prescription contact lenses during an optical device usage period (block 1646). Another possible related feature includes responsive to the determination, selecting an appropriate prefabricated corrective optical element that includes predetermined corrective parameters to ameliorate higher-level aberrations of the approved user (block 1647).

A further illustrated implementation includes making a determination whether the approved user will require both low-level and higher-level aberrational correction implemented in the prefabricated optical element, because of removal or other absence of any prescription eyeglasses or any prescription contact lenses during an optical device usage period (block 1648). an exemplary related aspect includes responsive to the determination, selecting an appropriate prefabricated corrective optical element that includes predetermined corrective parameters to ameliorate both low-level and higher-level aberrations of the approved user (block 1649).

Figure 54:
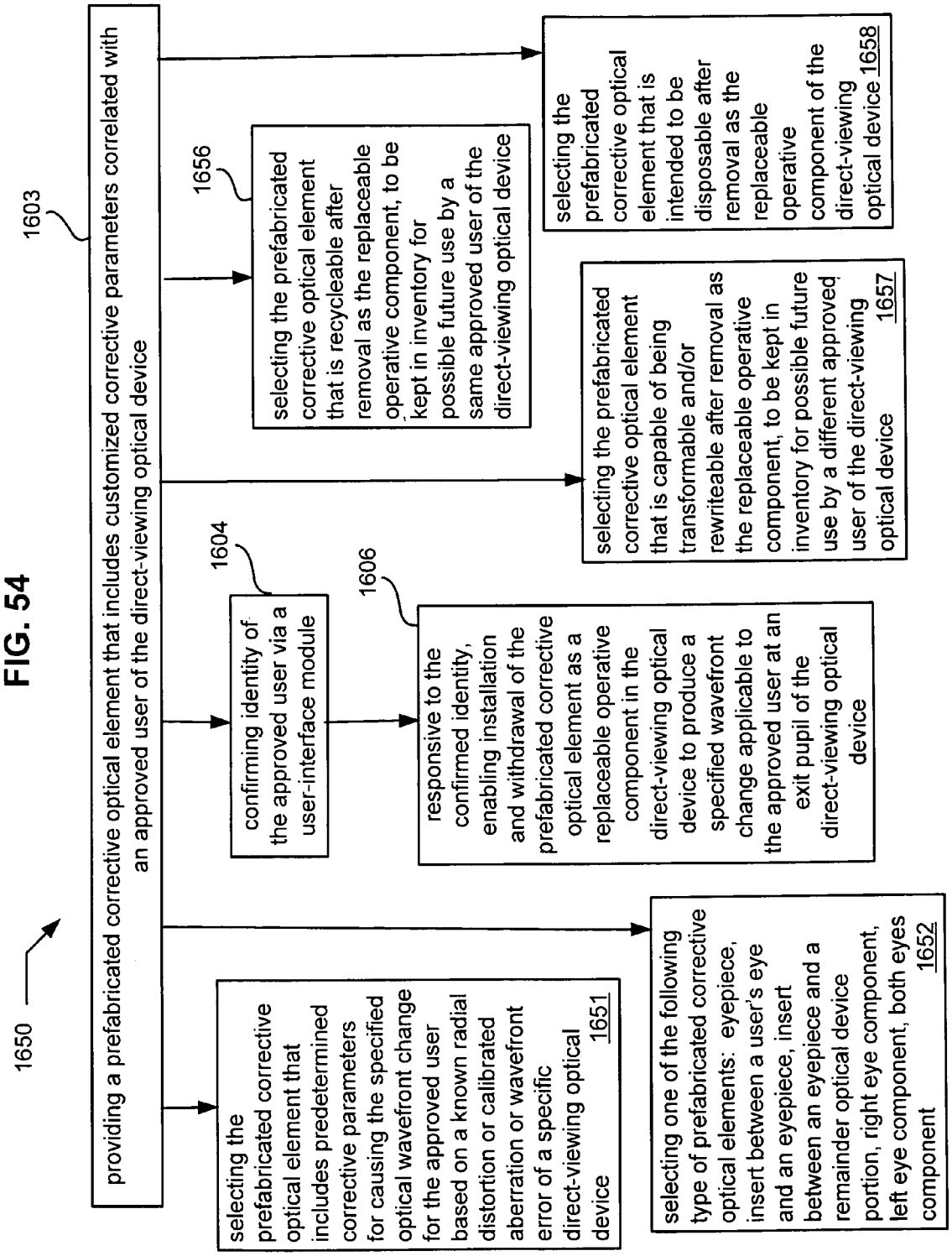

The detailed flow chart of FIG. 54 illustrates possible process enhancements including previously described aspects 1603, 1604, 160 in combination with selecting the prefabricated corrective optical element that includes predetermined corrective parameters for causing the specified optical wavefront change for the approved user based on a known radial distortion or calibrated aberration or wavefront error of a specific direct-viewing optical device (block 1651). A further process example includes selecting one of the following type of prefabricated corrective optical elements: eyepiece, insert between a user's eye and an eyepiece, insert between an eyepiece and a remainder optical device portion, right eye component, left eye component, both eyes component (block 1652).

Additional possibilities include selecting the prefabricated corrective optical element that is recyclable after removal as the replaceable operative component, to be kept in inventory for possible future use by a same approved user of the direct-viewing optical device (block 1656). In some instances a method feature may include selecting the prefabricated corrective optical element that is capable of being transformable and/or rewriteable after removal as the replaceable operative component, to be kept in inventory for possible future use by a different approved user of the direct-viewing optical device (block 1657). Some implementations may further include selecting the prefabricated corrective optical element that is intended to be disposable after removal as the replaceable operative component of the direct-viewing optical device (block 1658).

Figure 55:
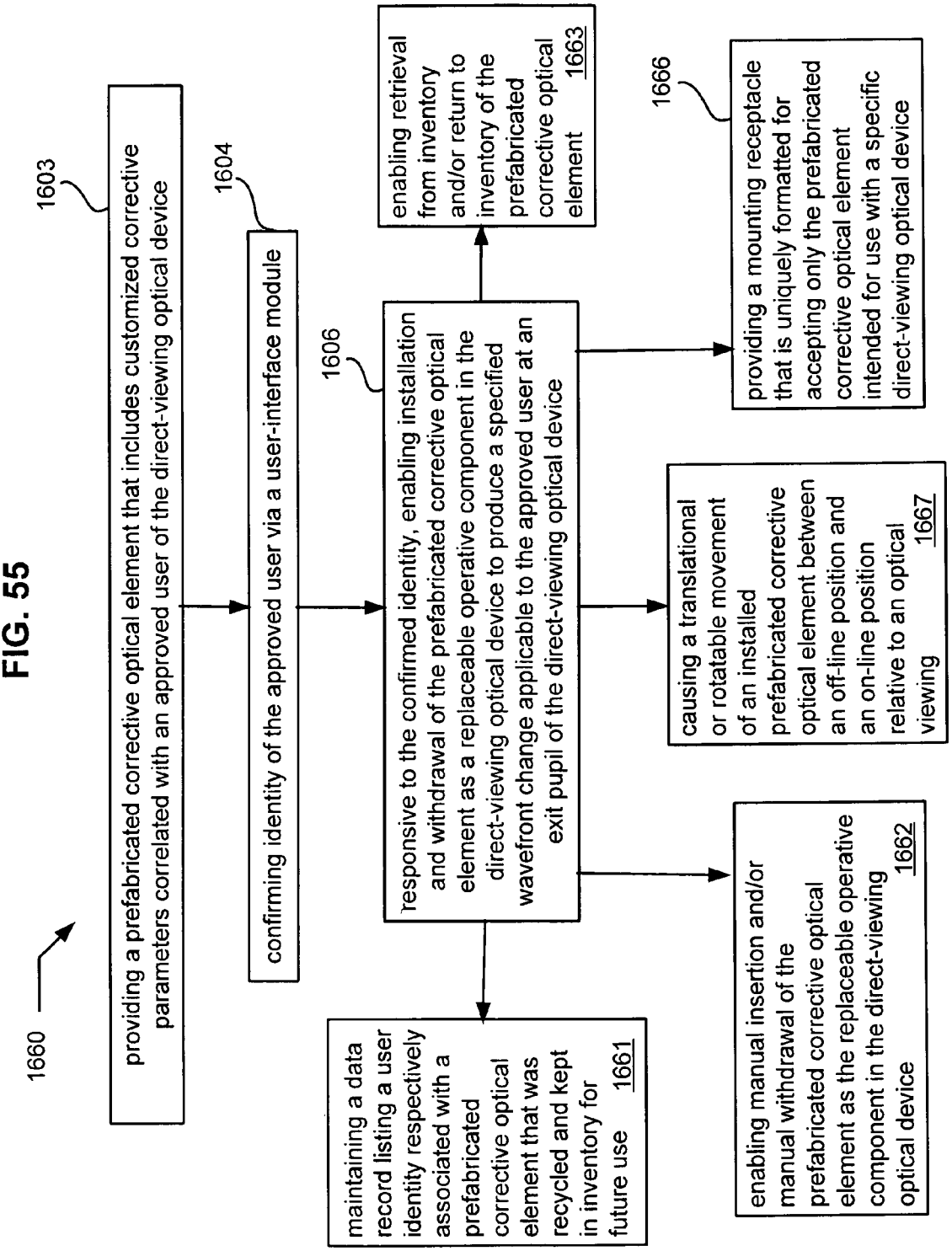

The detailed flow chart illustrated in FIG. 55 depicts various exemplary process aspects 1660 that include previously described operation 1603, 1604, 1606 as well as maintaining a data record listing a user identity respectively associated with the prefabricated corrective optical element that was recycled and kept in inventory for future use (block 1661). A further possible aspect includes enabling manual insertion and/or manual withdrawal of the prefabricated corrective optical element as the replaceable operative component in the direct-viewing optical device (block 1662). Some exemplary aspects may further include enabling retrieval from inventory and/or return to inventory of the prefabricated corrective optical element (block 1663).

Other possibilities include providing a mounting receptacle that is uniquely formatted for accepting only the prefabricated corrective optical element intended for use with a specific direct-viewing optical device (block 1666). A further process example includes causing a translational or rotatable movement of an installed prefabricated corrective optical element between an off-line position and an on-line position relative to an optical viewing path of the direct-viewing optical device (block 1667).

Figure 56:
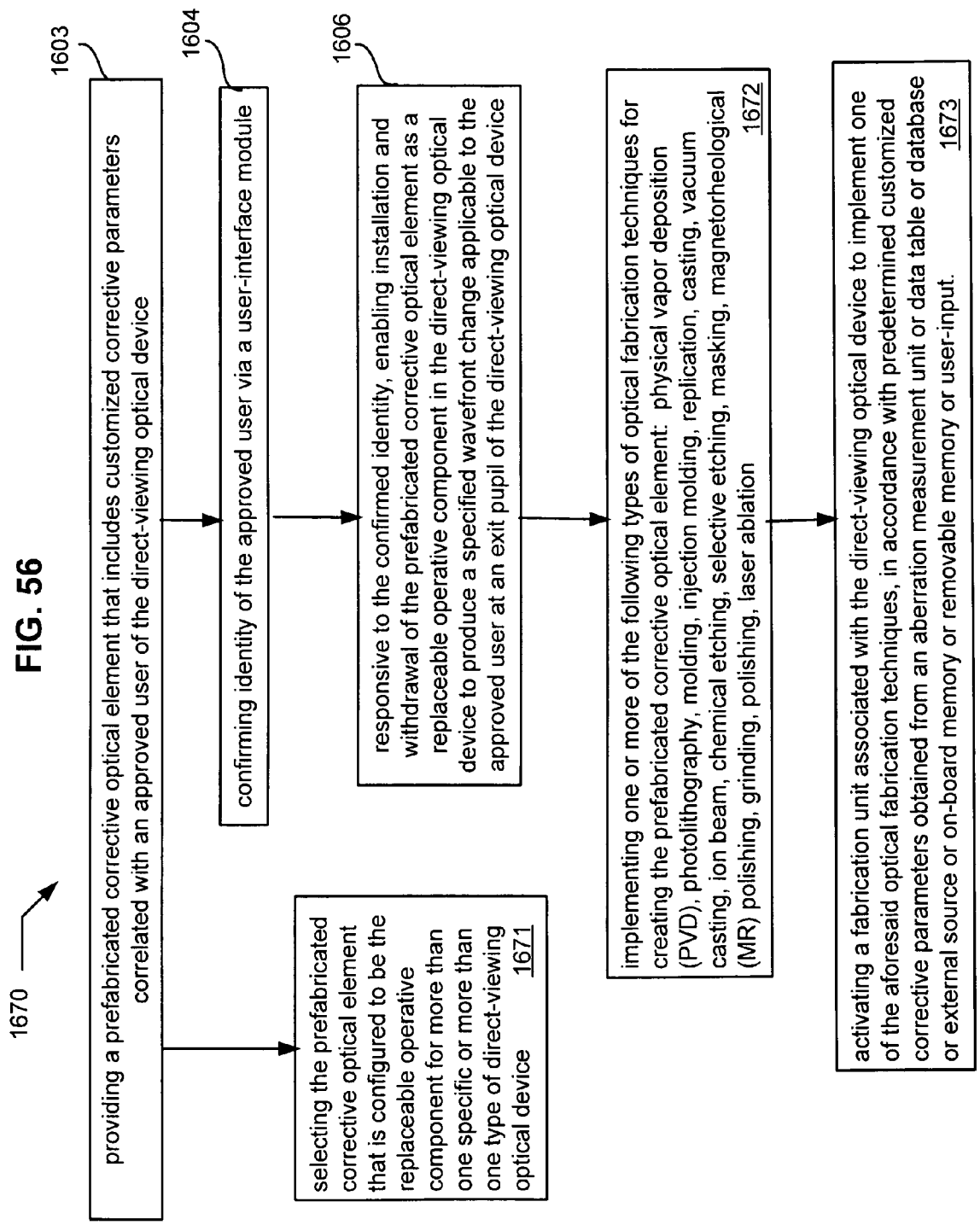

Various possible embodiment features 1670 are illustrated in the flow chart of FIG. 56 including previously described process aspects 1603, 1604, 1606 along with selecting the prefabricated corrective optical element that is configured to be the replaceable operative component for more than one specific or more than one type of direct-viewing optical device (block 1671).

Further examples include implementing one or more of the following types of optical fabrication techniques for creating the prefabricated corrective optical element: physical vapor deposition (PVD), photolithography, molding, injection molding, replication, casting, vacuum casting, ion beam, chemical etching, selective etching, masking, magnetorheological (MR) polishing, grinding, polishing, laser ablation (block 1672). Another exemplary aspect includes activating a fabrication unit associated with the direct-viewing optical device to implement one of the aforesaid optical fabrication techniques, in accordance with predetermined customized corrective parameters obtained from an aberration measurement unit or data table or database or external source or on-board memory or removable memory or user-input (block 1673).

Figure 57:
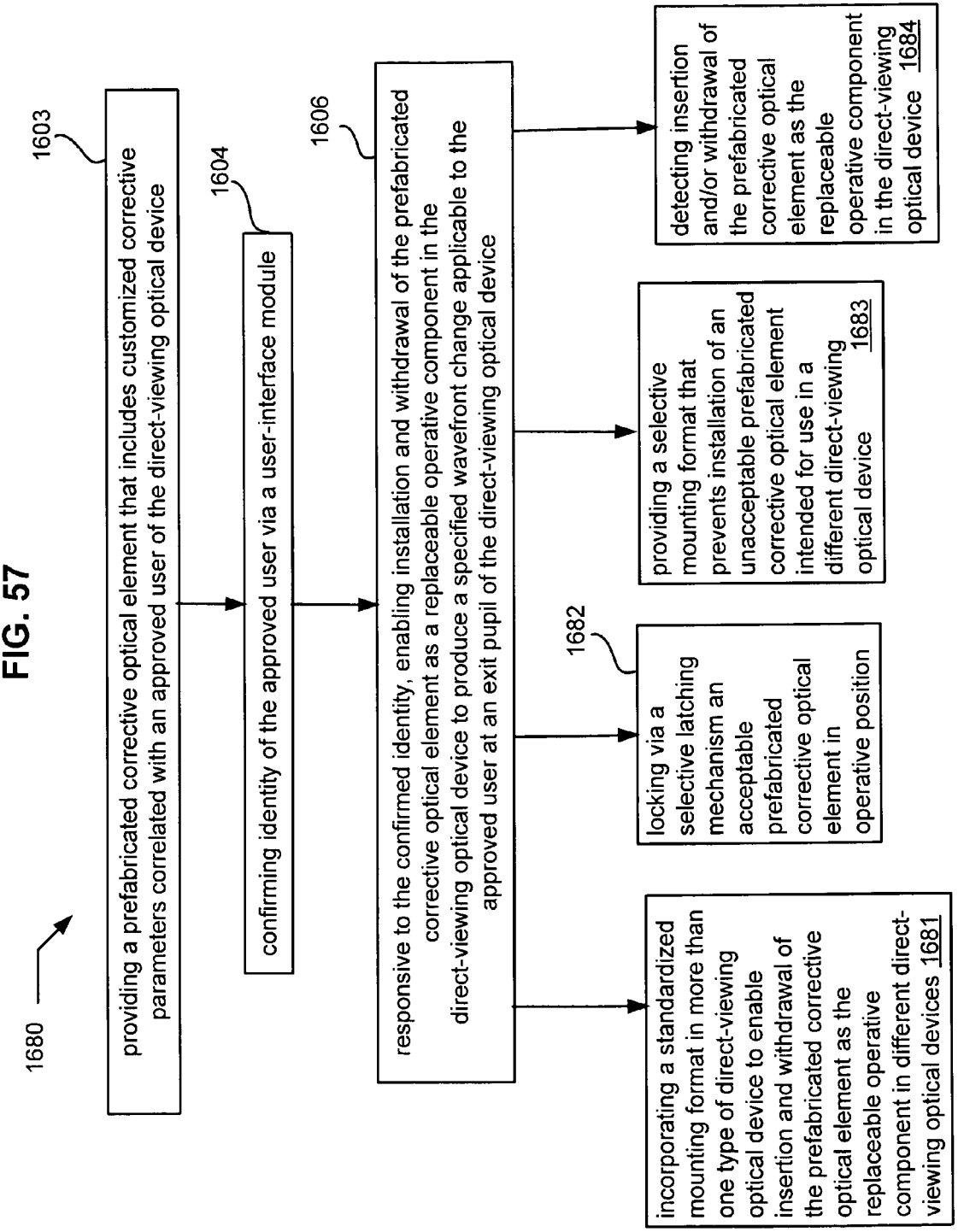

Referring to the detailed flow chart of FIG. 57, exemplary process aspects 1680 include previously described operation 1603, 1604, 1606 combined with incorporating a standardized mounting format in more than one type of direct-viewing optical device to enable insertion and withdrawal of the prefabricated corrective optical element as the replaceable operative component in different direct-viewing optical devices (block 1681). In some instances a process aspect includes locking via a selective latching mechanism an acceptable prefabricated corrective optical element in operative position (block 1682).

Additional possibilities include providing a selective mounting format that prevents installation of an unacceptable prefabricated corrective optical element intended for use in a different direct-viewing optical device (block 1683). Another example includes detecting insertion and/or withdrawal of the prefabricated corrective optical element as the replaceable operative component in the direct-viewing optical device (block 1684).

It will be understood from the exemplary embodiments disclosed herein that various individual method operations depicted in the flow charts of FIGS. 50-57 can be incorporated as encoded instructions in computer readable media in order to obtain enhanced benefits and advantages.

Figure 58:
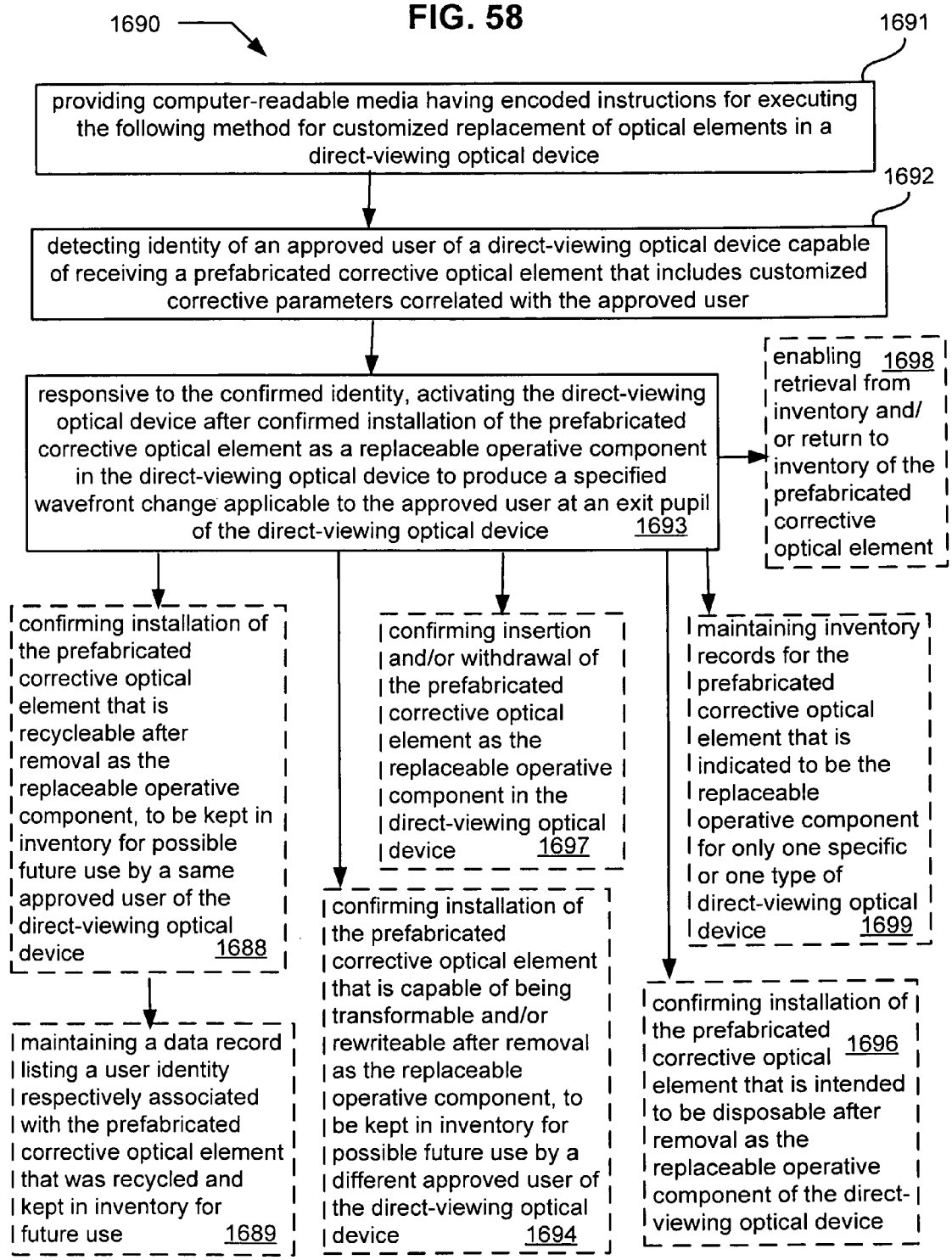
FIG. 58 is a diagrammatic flow chart for exemplary computer-readable media embodiment features.

As another embodiment example, FIG. 58 shows a diagrammatic flow chart 1690 depicting an article of manufacture which provides computer readable media having encoded instructions for executing a corrective method for a direct-viewing optical device (see 1691), wherein the method includes detecting identity of an approved user of a direct-viewing optical device capable of receiving a prefabricated corrective optical element that includes customized corrective parameters correlated with the approved user (block 1692); and responsive to the confirmed identity, activating the direct-viewing optical device after confirmed installation of the prefabricated corrective optical element as a replaceable operative component in the direct-viewing optical device to produce a specified wavefront change applicable to the approved user at an exit pupil of the direct-viewing optical device (block 1693).

Additional possible programmed aspects include confirming installation of the prefabricated corrective optical element that is recyclable after removal as the replaceable operative component, to be kept in inventory for possible future use by a same approved user of the direct-viewing optical device (block 1688). A related programmed aspect may include maintaining a data record listing a user identity respectively associated with the prefabricated corrective optical element that was recycled and kept in inventory for future use (block 1689).

Some embodiments may provide a programmed feature that includes confirming installation of the prefabricated corrective optical element that is capable of being transformable and/or rewriteable after removal as the replaceable operative component, to be kept in inventory for possible future use by a different approved user of the direct-viewing optical device (block 1694). Another possible programmed feature includes confirming installation of the prefabricated corrective optical element that is intended to be disposable after removal as the replaceable operative component of the direct-viewing optical device (block 1696).

In some instances a further programmed aspect includes confirming insertion and/or withdrawal of the prefabricated corrective optical element as the replaceable operative component in the direct-viewing optical device (block 1697). An additional programmed example includes enabling retrieval from inventory and/or return to inventory of the prefabricated corrective optical element (block 1698). Another possible programmed aspect includes maintaining inventory records for the prefabricated corrective optical element that is indicated to be the replaceable operative component for only one specific or one type of direct-viewing optical device (block 1699).

Figure 59:
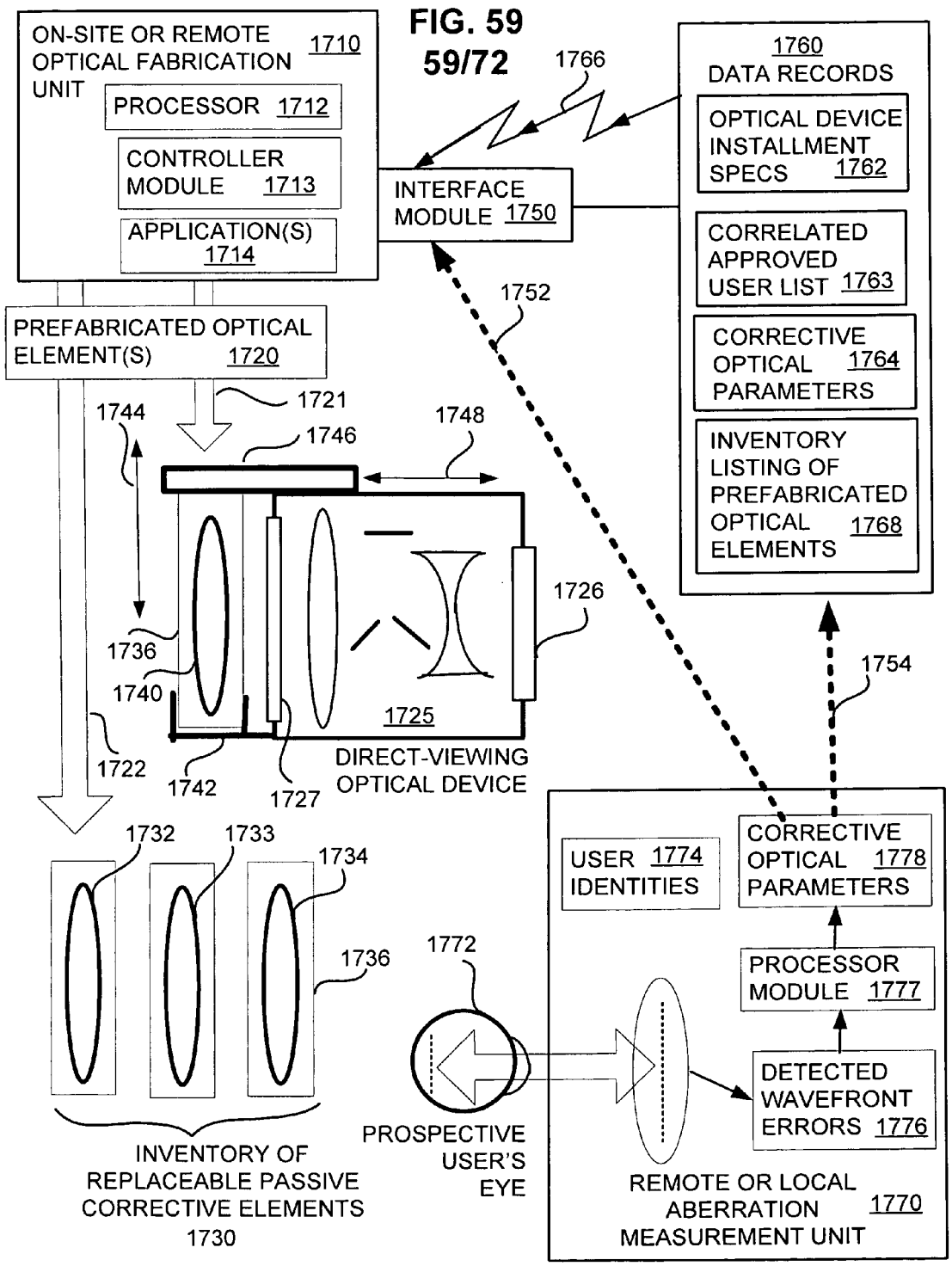
FIGS. 59 and 60 are schematic block diagrams illustrating embodiment features for fabrication of replaceable optical elements that incorporate customized corrective optical parameters.

Referring to the schematic block diagram of FIG. 59, an exemplary on-site or remote optical fabrication unit 1710 includes processor 1712, controller module 1713, and one or more applications 1714 which are configured to create various types of prefabricated optical elements 1720 capable of removable installation in a direct-viewing optical device 1725 having aperture 1726. Where an embodiment includes an on-site optical fabrication unit 1710 associated with the direct-viewing optical device 1725, such a prefabricated optical element may be directly available (see 1721) for automatic or manual insertion (see directional arrow 1744) in a mounting receptacle 1742 that is attached adjacent to an eyepiece 1727 of the direct-viewing optical device 1725.

In some instances the mounting receptacle 1742 is adapted for complementary supporting contact with a casing 1736 of a prefabricated optical element 1740. Such complementary supporting contact may in some instances be in accordance with certain optical device installment specifications (e.g., see 1762 in data records 1760) to facilitate secure installation as well as to avoid inadvertent installation into a non-approved or non-correlated direct-viewing optical device. Additional installation aspects may include a slidable capping member 1746 adapted for moving back and forth (see directional arrow 1748) between a closed latching position as shown in FIG. 59 and an open-access position that allows insertion or withdrawal of the prefabricated optical element 1740 as an operative component of the direct-viewing optical device 1725.

In the event an approved user is not presently scheduled for usage of the direct-viewing optical device 1725, one or more prefabricated optical elements can be transferred (see 1722) to an inventory of replaceable passive corrective elements 1730 to be available for usage at a future time period. Such an inventory collection may include separately calibrated optical elements 1732, 1733, 1734 respectively correlated with different approved users of direct-viewing optical device 1726.

Of course it will be understood that after a device usage period with prefabricated optical element 1740 had been completed, such prefabricated optical element 1740 may also be transferred to the inventory collection 1730 to be available for usage at a future time period.

Another system embodiment feature may include an interface module 1750 having a communication link with the optical fabrication unit 1710 in a manner to enable informational data regarding customized corrective optical parameters to be accessible to optical fabrication unit 1710 as well as to other interested parties. Such informational data may be obtainable via wired communication channel and/or wireless transmission (see 1766) from various types of data records 1760 that could include a data table or database or external source as well as in some instances an on-board memory or removable memory of the direct-viewing optical device 1725.

Examples of pertinent information maintained in data records 1760 to be accessible to optical fabrication unit 1710 may include corrective optical parameters 1764 and their correlated approved user list 1763 to achieve enhanced acuity of the direct-viewing optical device 1725. Another pertinent type of updatable information maintained in data records 1760 may include an inventory listing of prefabricated optical elements 1768 available for future use. Additional helpful information maintained in data records 1760 may include optical device installment specifications 1762 applicable to the direct-viewing optical device 1725 that are indicative of a definitive external size and/or shape and/or calibration for the casing 1736 in order to achieve complementary acceptance by mounting receptacle 1742. It will be understood that some embodiments will provide prefabricated optical elements capable of being removably installed without any need for a protective frame such as casing 1736, depending on the circumstances of usage and also the type of direct-viewing optical device involved (e.g., table mounted, handheld, high precision, etc.)

In some embodiments a communication link 1752 may be provided between interface module 1750 and a remote or local aberration measurement unit 1770 configured for diagnostic monitoring of a prospective user's eye 1772 in order to obtain detected wavefront errors 1776 associated with one or more user identities 1774. The aberration measurement unit 1770 may include processor module 1777 that includes circuitry and/or specialized software programs for data manipulation and processing and calculation to generate corrective optical parameters 1778 correlated respectively with individual user identities 1774. In some implementation it may be desirable to provide a communication link 1754 from the aberration measurement unit 1770 for purposes of updating data records 1760 to assure maintenance of data integrity and future availability of the detected wavefront errors 1776, respective user identities 1774, and generated corrective optical parameters 1778.

Figure 60:
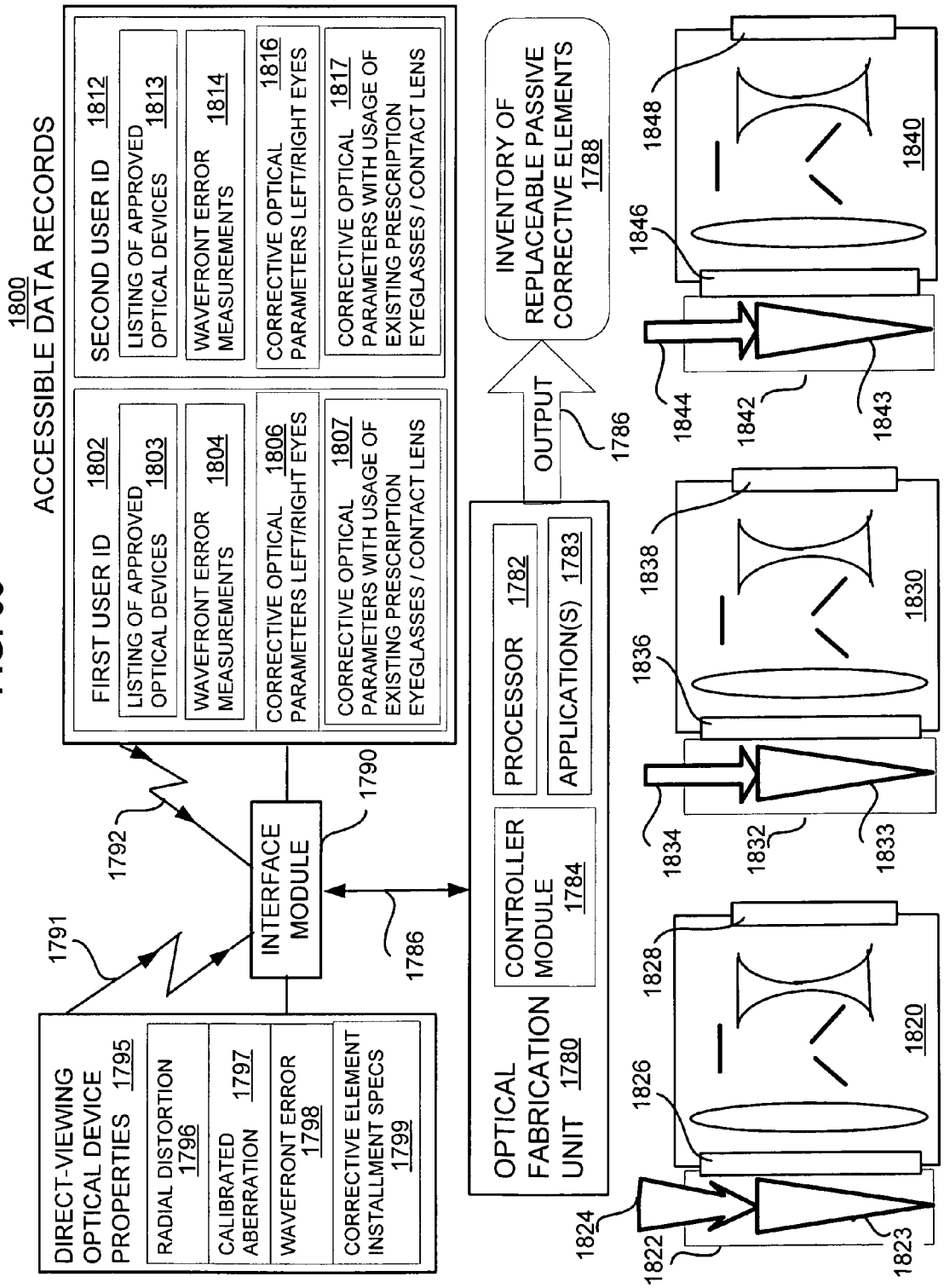

The schematic block diagram of FIG. 60 illustrates additional exemplary embodiment features related to an optical fabrication unit 1780 that includes processor 1782, one or more programmed applications 1783, and controller module 1784. A communication link 1786 may provide an operable connection between the optical fabrication unit 1780 and accessible data records 1800 via an interface module 1790. The communication link 1786 may also provide an operable connection between the optical fabrication unit 1780 and other accessible data indicating direct-viewing optical device properties 1795 via the interface module 1790. It will be understood that communication links with interface module 1790 may be implemented via wireless transmission (see 1791, 1792) as well as in some instances via wired communication channels.

Such operative connections via interface module 1790 facilitate creation of various types of prefabricated replaceable corrective optical elements for current operative installation in specifically different direct-viewing optical devices such as 1820 with aperture 1828, 1830 with aperture 1838, and 1840 with aperture 1848. A further possible feature enables output 1786 from the optical fabrication unit 1780 to be transferred to an inventory of replaceable passive corrective elements 1788 which are maintained for removable installation in a particular direct-viewing optical device at a future time period.

Examples of the informational data maintained in the accessible data records 1800 include separate categories for individual users such as a first user identity (ID) 1802 and a second user identity (ID) 1812. Possible pertinent data entries regarding the first user ID 1802 include a listing of approved optical devices 1803, respective wavefront error measurements 1804, corrective optical parameters for left and right eyes 1806, and corrective optical parameters with usage of existing prescription eyeglasses or contact lens 1807. Possible pertinent data entries regarding the second user ID 1812 include a listing of approved optical devices 1813, respective wavefront error measurements 1814, corrective optical parameters for left and right eyes 1816, and corrective optical parameters with usage of existing prescription eyeglasses or contact lens 1817. Of course some users may have identical or closely similar aberrations for both eyes, thereby eliminating the need for listing separate eye corrective parameters.

Examples of the informational data maintained regarding direct-viewing optical device properties 1795 include radial distortion 1796, calibrated aberration 1797, and wavefront error 1799. An additional set of data may include corrective element installment specifications 1799 that assures complementary support between an installed prefabricated replaceable corrective element and a mounting receptacle in a particular direct-viewing optical device.

It will be appreciated that some mounting receptacles may be standardized for various types of direct-viewing optical devices (e.g., see 1830, 1840), while other mounting receptacles may incorporate definitive calibrated aspects that are uniquely associated with a specific one or a particular type of direct-viewing device (e.g., see 1820). In that regard the illustrated embodiments for direct-viewing devices 1830, 1840 include mounting receptacles 1832, 1842 respectively adjacent to eyepieces 1836, 1846, wherein both internal sleeves 1833, 1843 include a standardized size and/or shape (indicated by a same arrow-install symbol 1834, 1844) adapted for accepting various prefabricated replaceable corrective elements maintained in inventory 1788. In contrast the illustrated embodiment for direct-viewing device 1820 includes a mounting receptacle adjacent to eyepiece 1826, wherein an internal sleeve 1823 includes a unique size and/or shape (indicated by a stylized arrow-install symbol 1824) adapted to accept a prefabricated replaceable corrective element dedicated only for installation in direct-viewing device 1820.

Figure 61:
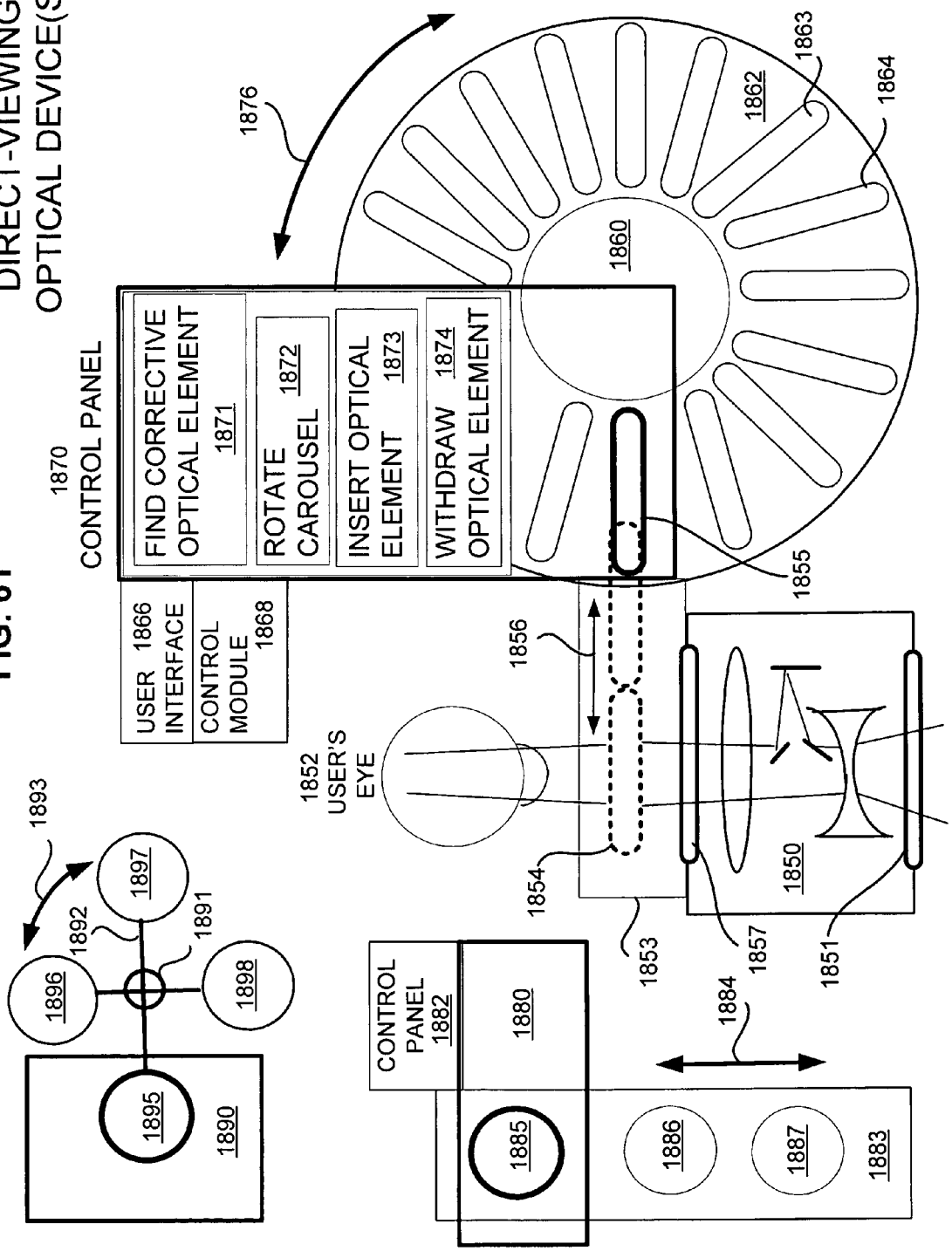
FIG. 61 is another schematic block diagram showing various examples of direct-viewing optical devices capable of removable insertion of passive optical corrective elements.

The schematic block diagram of FIG. 61 illustrates various examples of direct-viewing optical devices 1850, 1880, 1890 that are configured for accepting installation of prefabricated replaceable corrective elements correlated with an individual approved user. The drawing shows a top view of the embodiments of direct-viewing optical devices 1850, 1880, 1890 for purposes of clarity.

For example the embodiment for direct-viewing optical device 1850 includes aperture 1851, eyepiece 1857 and other reflective and/or refractive and/or diffractive and/or transmissive optical elements for enabling viewing by a current user's eye 1852. A mounting receptacle 1853 adjacent to eyepiece 1857 is adapted for programmed selection (see 1855) with subsequent automated insertion and eventual automated withdrawal (see directional arrow 1856) of the selected prefabricated passive corrective element (see 1855 shown in phantom as 1854) that includes corrective optical parameters correlated with the current user.

The mounting receptacle 1853 is operably coupled to an inventory carousel 1860 having an outer ring 1862 that includes slots (not shown) for holding individual prefabricated passive corrective elements (e.g., 1863, 1864). A user interface 1866 is provided for confirming an approved user identity and in some instances for accepting user input data. The user interface 1866 is operatively connected with a control module 1868 that may be programmed for supervisory management and rotation (see directional arrow 1876) of the inventory carousel 1860 pursuant to various command signals from a control panel 1870. For example when a user identity is confirmed by the control module 1868, an application program or circuitry is configured to respond to command signals that include "find corrective optical element" 1871, or "rotate carousel" 1872, or "insert optical element" 1873 into the mounting receptacle 1853, or "withdraw optical element" 1874 from the mounting receptacle 1853 in accordance with usage requirements that are entered via the user interface 1866. Of course other command signals can be incorporated as part of the control panel depending on the circumstances and the type of direct-viewing device that is involved. It will be understood that some approved users may have more than one correlated corrective element adapted for use on the same direct-viewing optical device 1850.

As another example, direct-viewing optical device 1880 includes control panel 1882 operably connected with appropriate computerized circuitry and/or programmed applications (not shown) to enable automated insertion and withdrawal of selected prefabricated passive corrective elements 1885, 1886, 1887. A longitudinal slide member 1883 is configured to securely hold each of the corrective elements 1885, 1886, 1887, wherein the longitudinal slide member 1883 is activated by the control panel 1882 for movement back and forth (see directional arrow 1884) in response to commands from the control panel 1882. Corrective optical element 1885 is shown to be currently installed as an operative component of the direct-viewing optical device 1880. Based on usage requirements by multiple approved users, some of the corrective elements held in the longitudinal slide member 1883 can be removed for temporary storage in inventory, and replacement corrective elements can be obtain from inventory for placement on the longitudinal slide member 1883. Of course some approved users may have more than one correlated corrective element adapted for use on the same direct-viewing optical device 1880.

As a further example, direct-viewing optical device 1890 includes a rotational wheel 1891 having separate arms 1892 that securely hold individual prefabricated passive corrective elements 1895, 1896, 1897, 1898. The rotational wheel can be manually rotated (see directional arrow 1893) to install a selected corrective element as an operative component (see 1895) of the direct-viewing optical device 1890 during usage by a correlated approved user. Based on usage requirements by multiple approved users, some of the corrective elements held on the rotational wheel 1891 can be removed for temporary storage in inventory, and replacement corrective elements can be obtain from inventory for placement on the separate arms 1892. Of course some approved users may have more than one correlated corrective element adapted for use on the same direct-viewing optical device 1890.

Figure 62:
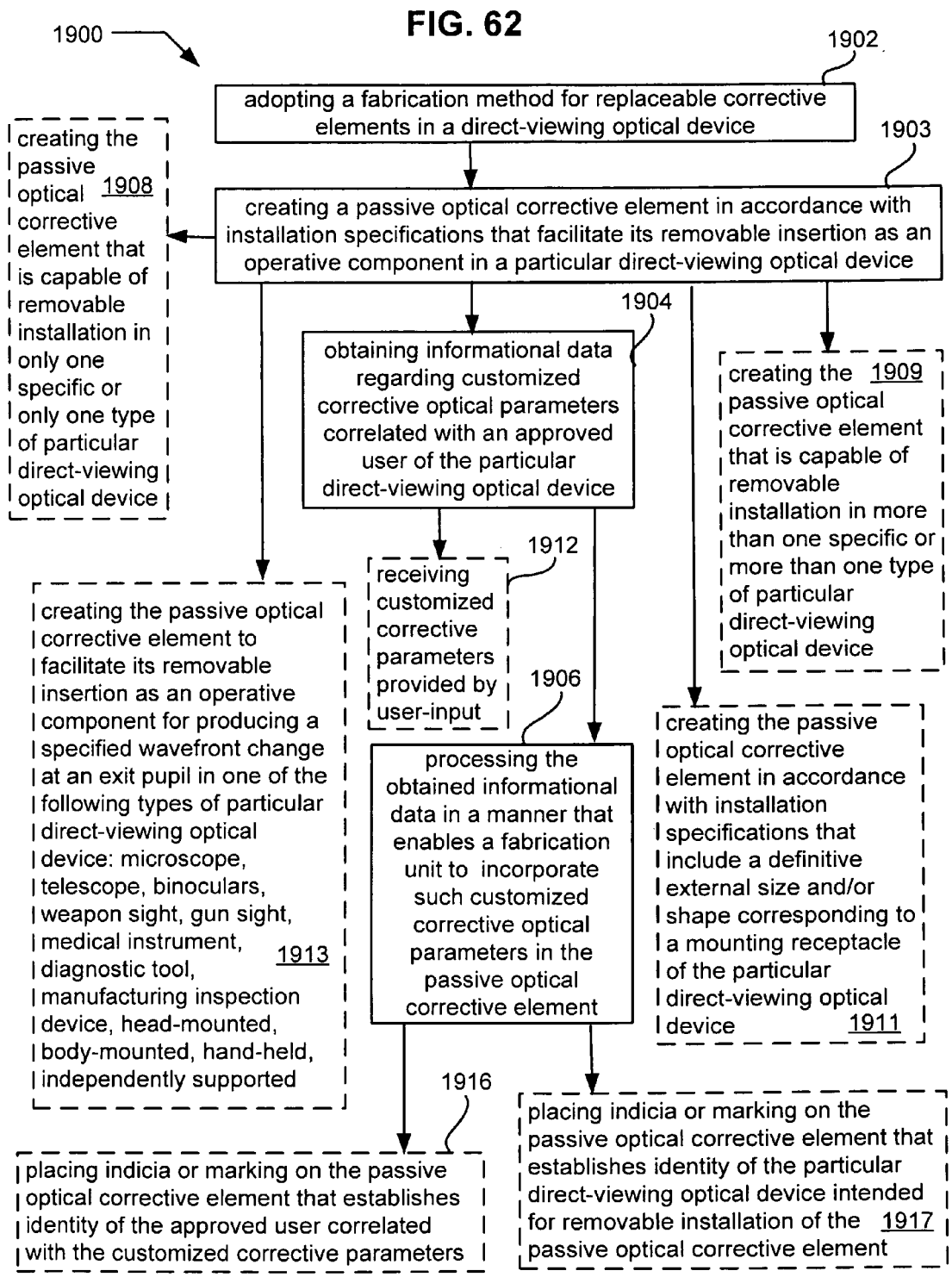
FIG. 62 is a high level flow chart that shows exemplary method aspects for fabricating replaceable corrective elements adapted for a direct-viewing optical device.

Referring to the flow chart of FIG. 62, various possible process embodiment features 1900 are illustrated in connection with adopting a fabrication method for replaceable corrective elements in a direct-viewing optical device (see 1902), including creating a passive optical corrective element in accordance with installation specifications that facilitate its removable insertion as an operative component in a particular direct-viewing optical device (block 1903), obtaining informational data regarding customized corrective optical parameters correlated with an approved user of the particular direct-viewing optical device (block 1904), and processing the obtained informational data in a manner that enables a fabrication unit to incorporate such customized corrective optical parameters in the passive optical corrective element (block 1905).

Other possible process aspects may include creating the passive optical corrective element that is capable of removable installation in only one specific or only one type of particular direct-viewing optical device (block 1908). Another example includes creating the passive optical corrective element that is capable of removable installation in more than one specific or more than one type of particular direct-viewing optical device (block 1909). A further example includes creating the passive optical corrective element in accordance with installation specifications that include a definitive external size and/or shape corresponding to a mounting receptacle of the particular direct-viewing optical device (block 1911). Some embodiments may include receiving customized corrective parameters provided by user-input (block 1912).

In some instances a process aspect includes creating the passive optical corrective element to facilitate its removable insertion as an operative component for producing a specified wavefront change at an exit pupil in one of the following types of particular direct-viewing optical device: microscope, telescope, binoculars, weapon sight, gun sight, medical instrument, diagnostic tool, manufacturing inspection device, head-mounted, body-mounted, hand-held, independently supported (block 1913).

Another possibility includes placing indicia or marking on the passive optical corrective element that establishes identity of the approved user correlated with the customized corrective parameters (block 1916). A further possibility includes placing indicia or marking on the passive optical corrective element that establishes identity of the particular direct-viewing optical device intended for removable installation of the passive optical corrective element (block 1917).

Figure 63:
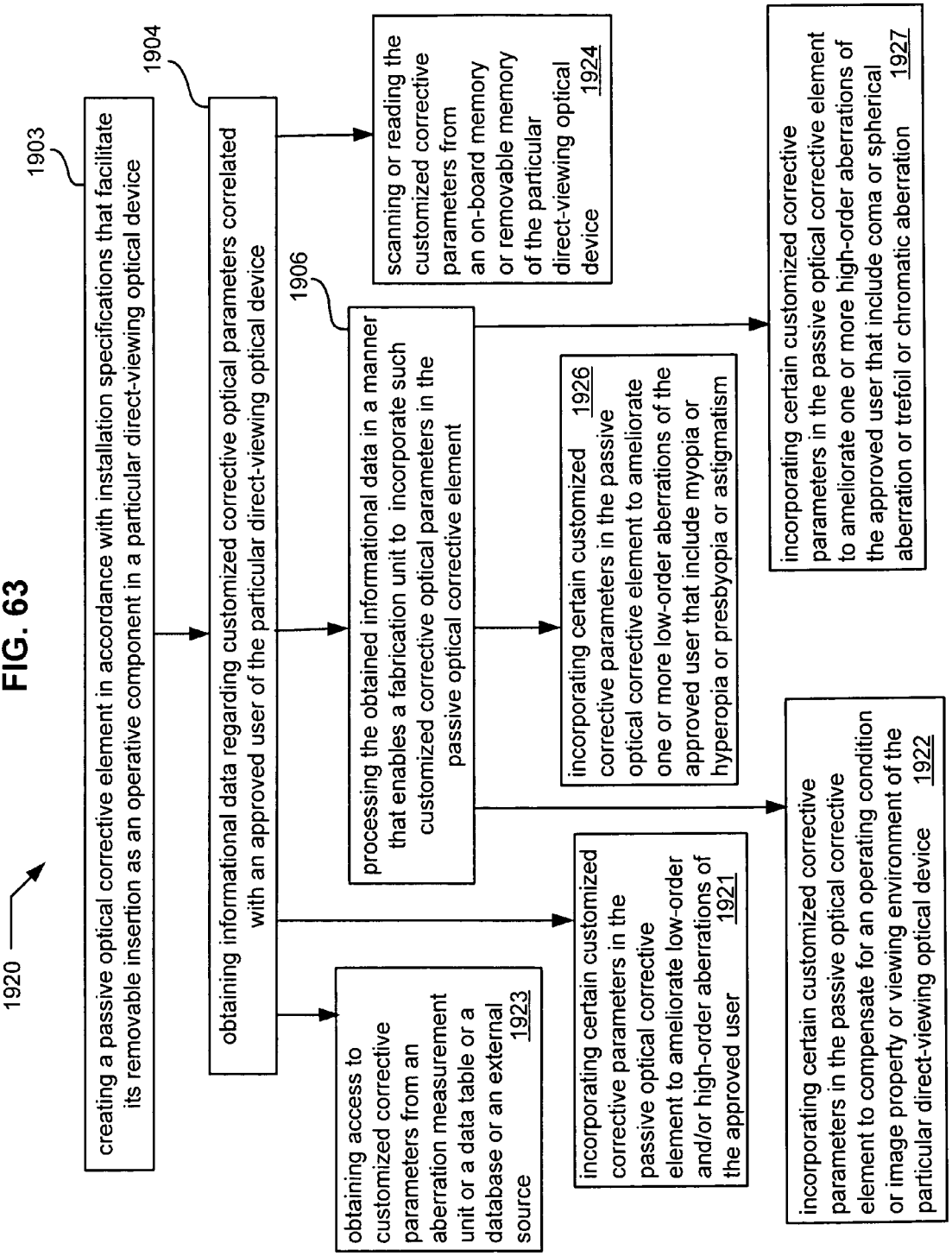
FIGS. 63-66 are detailed flow charts illustrating additional exemplary method aspects regarding fabrication of the replaceable corrective elements.

The detailed flow chart of FIG. 63 illustrates various embodiment examples 1920 that include previously described operations 1903, 1904, 1906 in combination with incorporating certain customized corrective parameters in the passive optical corrective element to ameliorate low-order and/or high-order aberrations of the approved user (block 1921). Another example includes incorporating certain customized corrective parameters in the passive optical corrective element to compensate for an operating condition or image property or viewing environment of the particular direct-viewing optical device (block 1922).

Additional process aspects may include obtaining access to customized corrective parameters from an aberration measurement unit or a data table or a database or an external source (block 1923). Another process aspect may include scanning or reading the customized corrective parameters from an on-board memory or removable memory of the particular direct-viewing optical device (block 1924). Further possible enhancements include incorporating certain customized corrective parameters in the passive optical corrective element to ameliorate one or more low-order aberrations of the approved user that include myopia or hyperopia or presbyopia or astigmatism (block 1926). Some embodiment features may include incorporating certain customized corrective parameters in the passive optical corrective element to ameliorate one or more high-order aberrations of the approved user that include coma or spherical aberration or trefoil or chromatic aberration (block 1927).

Figure 64:
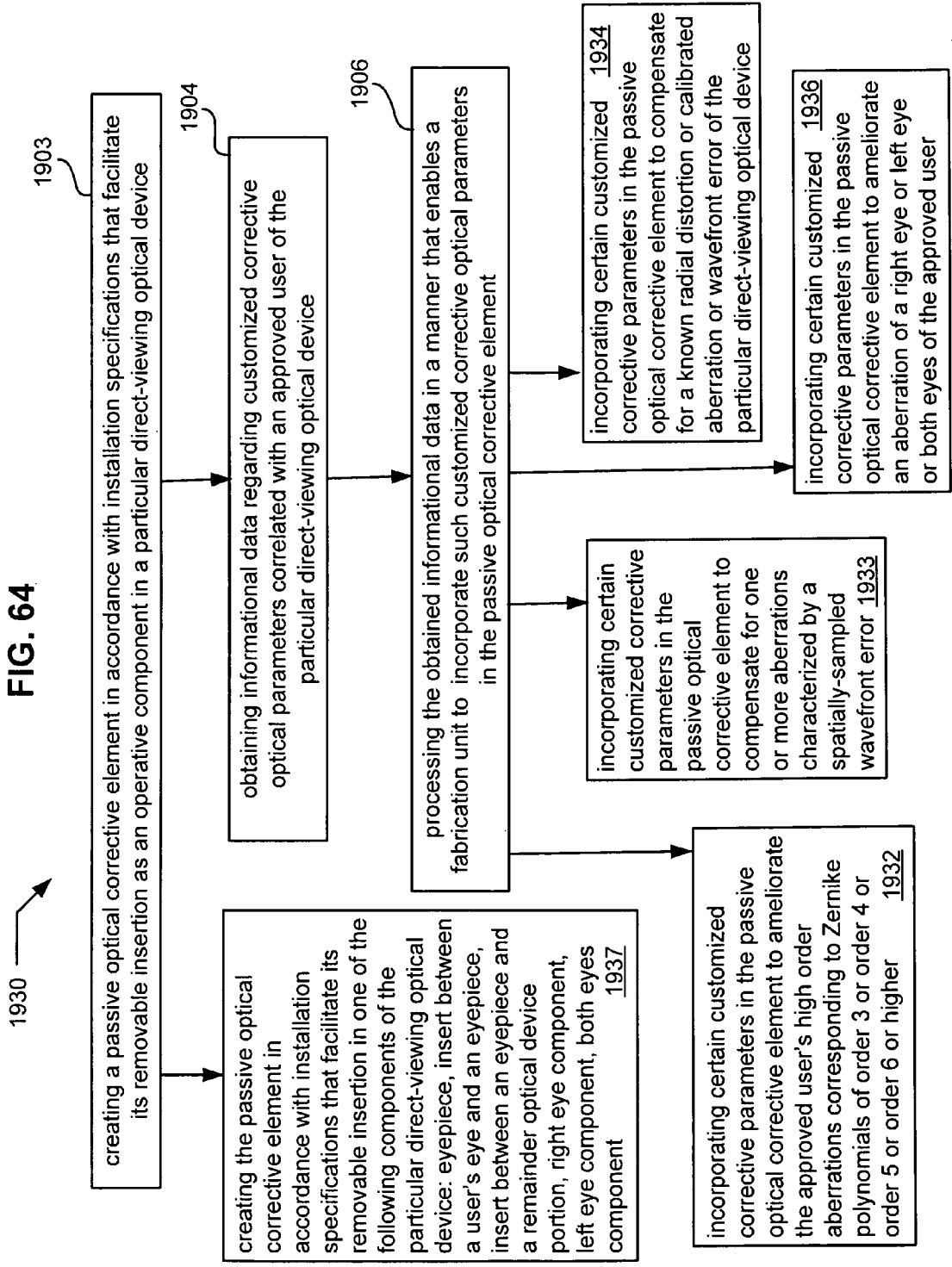

The exemplary embodiment features 1930 illustrated in FIG. 64 include previously described aspects 1903, 1904, 1906 as well as creating the passive optical corrective element in accordance with installation specifications that facilitate its removable insertion in one of the following components of the particular direct-viewing optical device: eyepiece, insert between a user's eye and an eyepiece, insert between an eyepiece and a remainder optical device portion, right eye component, left eye component, both eyes component (block 1937).

Another possible process aspect includes incorporating certain customized corrective parameters in the passive optical corrective element to ameliorate the approved user's high order aberrations corresponding to Zernike polynomials of order 3 or order 4 or order 5 or order 6 or higher (block 1932). A further example includes incorporating certain customized corrective parameters in the passive optical corrective element to compensate for one or more aberrations characterized by a spatially-sampled wavefront error (block 1933).

Other possibilities include incorporating certain customized corrective parameters in the passive optical corrective element to compensate for a known radial distortion or calibrated aberration or wavefront error of the particular direct-viewing optical device (block 1934). Some implementations may include incorporating certain customized corrective parameters in the passive optical corrective element to ameliorate an aberration of a right eye or left eye or both eyes of the approved user (block 1936).

Figure 65:
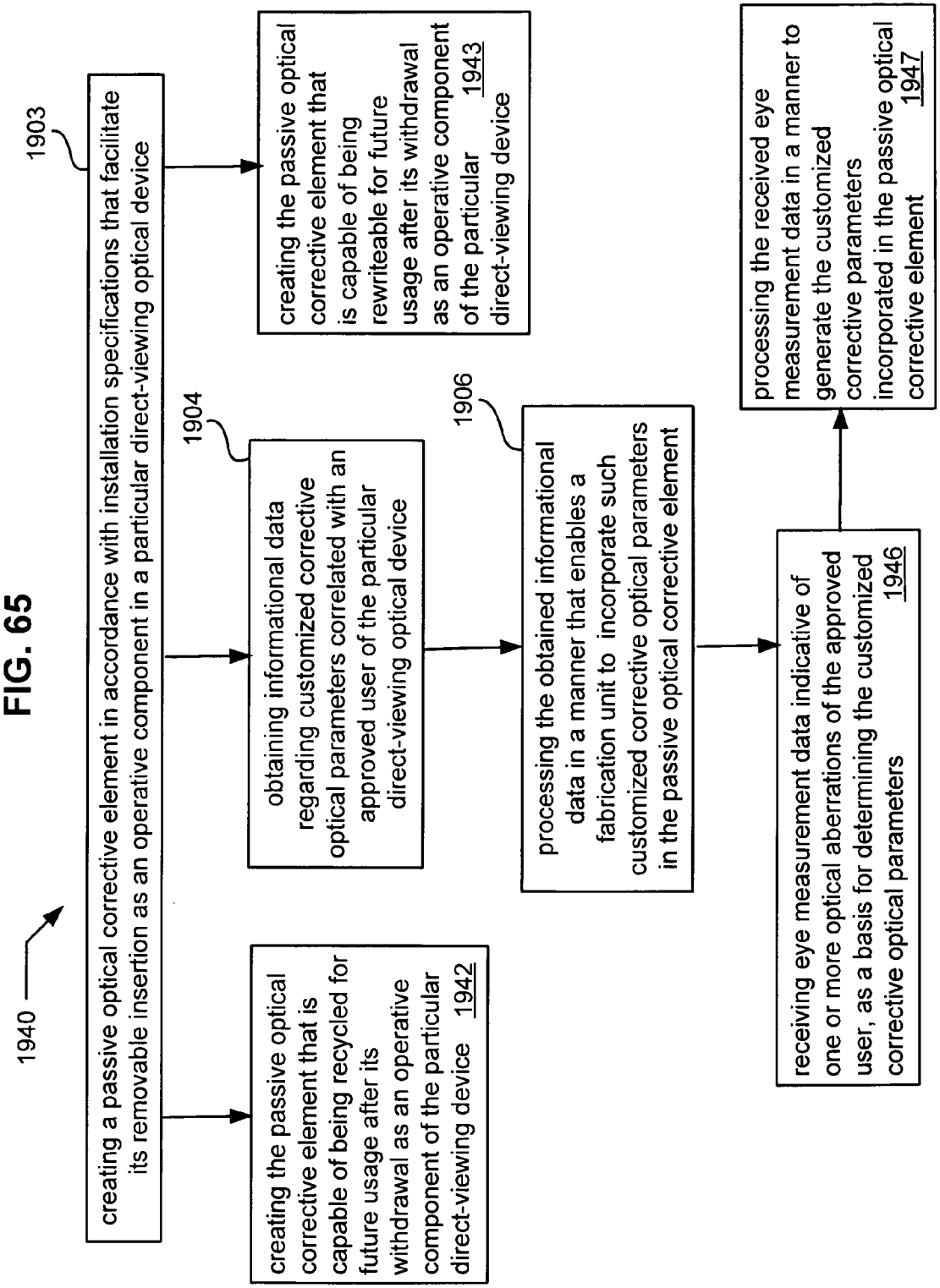

FIG. 65 illustrates additional combinations of various process features 1940 that include previously described aspects 1903, 1904, 1906 as well as creating the passive optical corrective element that is capable of being recycled for future usage after its withdrawal as an operative component of the particular direct-viewing device (block 1942). Further possible process features include creating the passive optical corrective element that is capable of being rewriteable for future usage after its withdrawal as an operative component of the particular direct-viewing device (block 1943).

Some embodiments may include receiving eye measurement data indicative of one or more optical aberrations of the approved user, as a basis for determining the customized corrective optical parameters (block 1946). A related possible aspect includes processing the received eye measurement data in a manner to generate the customized corrective parameters incorporated in the passive optical corrective element (block 1947).

Figure 66:
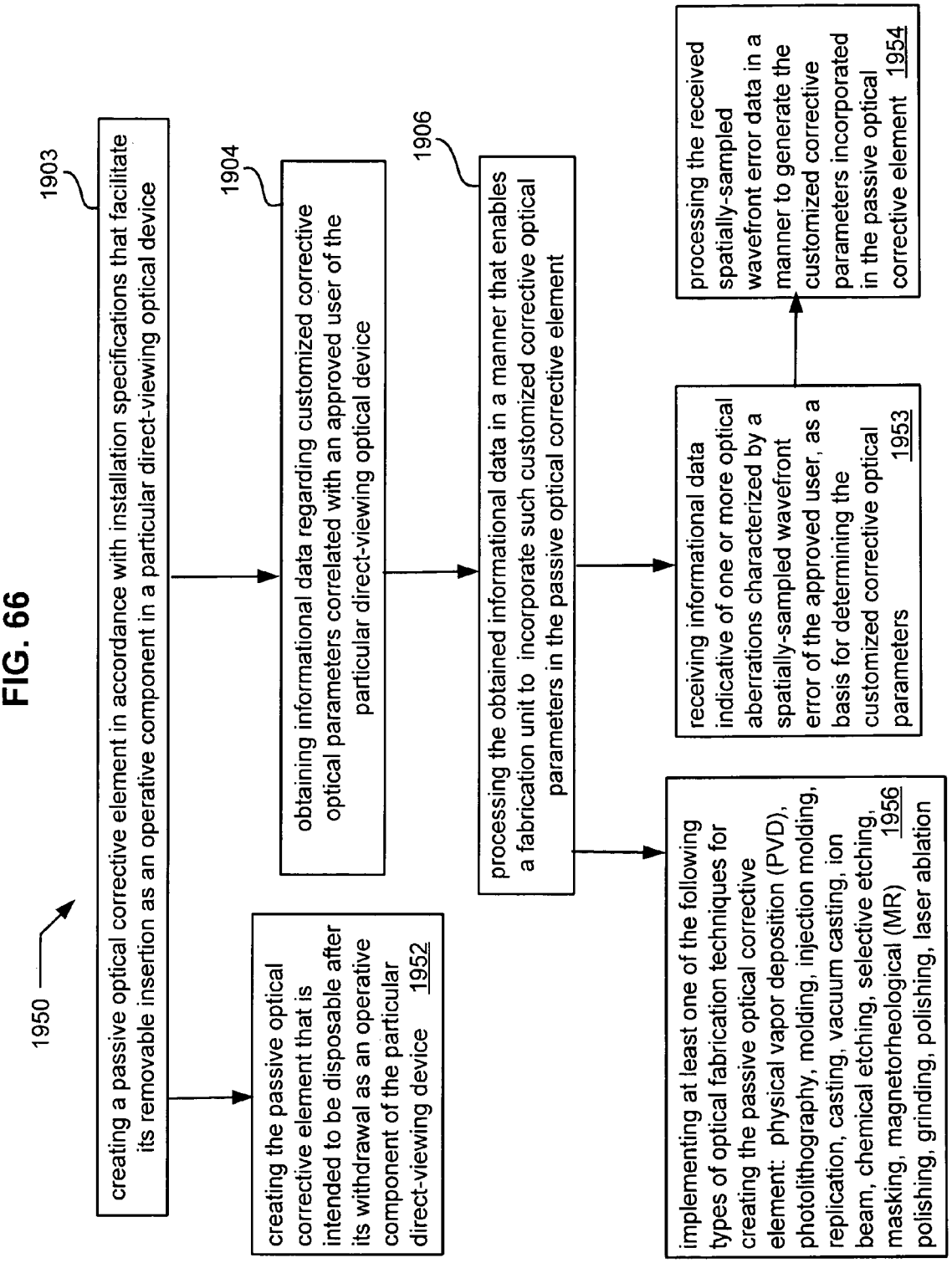

Referring to the detailed flow chart of FIG. 66, possible process embodiment features 1950 include previously described operations 1903, 1904, 1906 in combination with creating the passive optical corrective element that is intended to be disposable after its withdrawal as an operative component of the particular direct-viewing device (block 1952). Another process example includes implementing at least one of the following types of optical fabrication techniques for creating the passive optical corrective element: physical vapor deposition (PVD), photolithography, molding, injection molding, replication, casting, vacuum casting, ion beam, chemical etching, selective etching, masking, magnetorheological (MR) polishing, grinding, polishing, laser ablation (block 1956).

A further possible enhancement includes receiving informational data indicative of one or more optical aberrations characterized by a spatially-sampled wavefront error of the approved user, as a basis for determining the customized corrective optical parameters (block 1953). A related aspect may include processing the received spatially-sampled wavefront error data in a manner to generate the customized corrective parameters incorporated in the passive optical corrective element (block 1954).

It will be understood from the exemplary embodiments disclosed herein that various individual method operations depicted in the flow charts of FIGS. 62-66 can be incorporated as encoded instructions in computer readable media to obtain further benefits and advantages.

Figure 67:
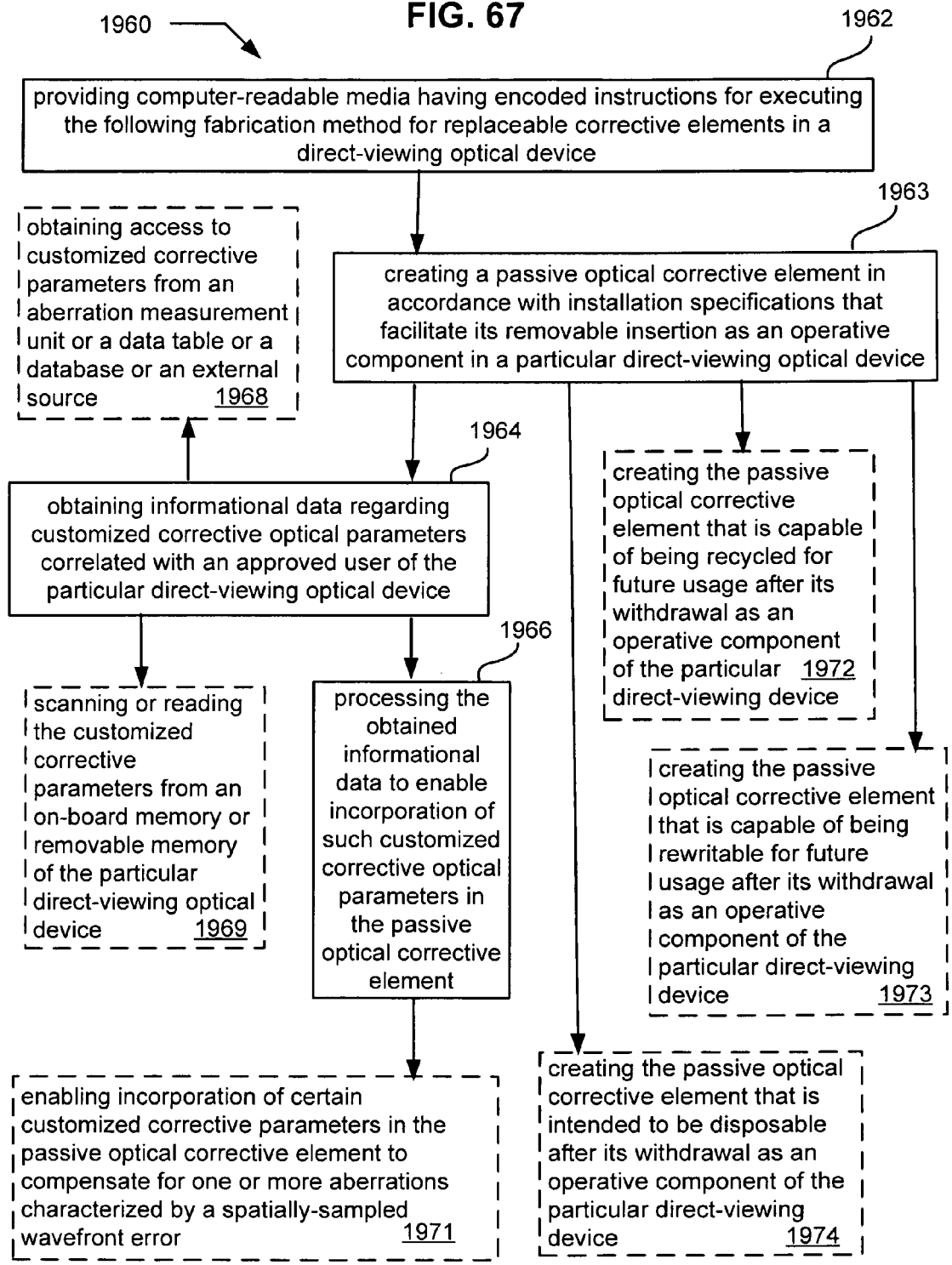
FIG. 67 a diagrammatic flow chart for exemplary computer-readable media embodiment features.

As another embodiment example, FIG. 67 shows a diagrammatic flow chart 1960 depicting an article of manufacture implemented in computer readable media having encoded instructions for executing a fabrication method for replaceable corrective elements in a direct-viewing optical device (see 1962), wherein the method includes creating a passive optical corrective element in accordance with installation specifications that facilitate its removable insertion as an operative component in a particular direct-viewing optical device (block 1963), obtaining informational data regarding customized corrective optical parameters correlated with an approved user of the particular direct-viewing optical device, (block 1964), and processing the obtained informational data to enable incorporation of such customized corrective optical parameters in the passive optical corrective element (block 1966).

Further possible programmed aspects include obtaining access to customized corrective parameters from an aberration measurement unit or a data table or a database or an external source (block 1968), and in some instances scanning or reading the customized corrective parameters from an on-board memory or removable memory of the particular direct-viewing optical device (block 1969). Another example of a programmed operation includes creating the passive optical corrective element that is capable of being recycled for future usage after its withdrawal as an operative component of the particular direct-viewing device (block 1971).

Additional examples of programmed operations shown in FIG. 67 include creating the passive optical corrective element that is capable of being rewriteable for future usage after its withdrawal as an operative component of the particular direct-viewing device (block 1972). Some programmed aspects may include creating the passive optical corrective element that is intended to be disposable after its withdrawal as an operative component of the particular direct-viewing device (block 1973).

Figure 68:
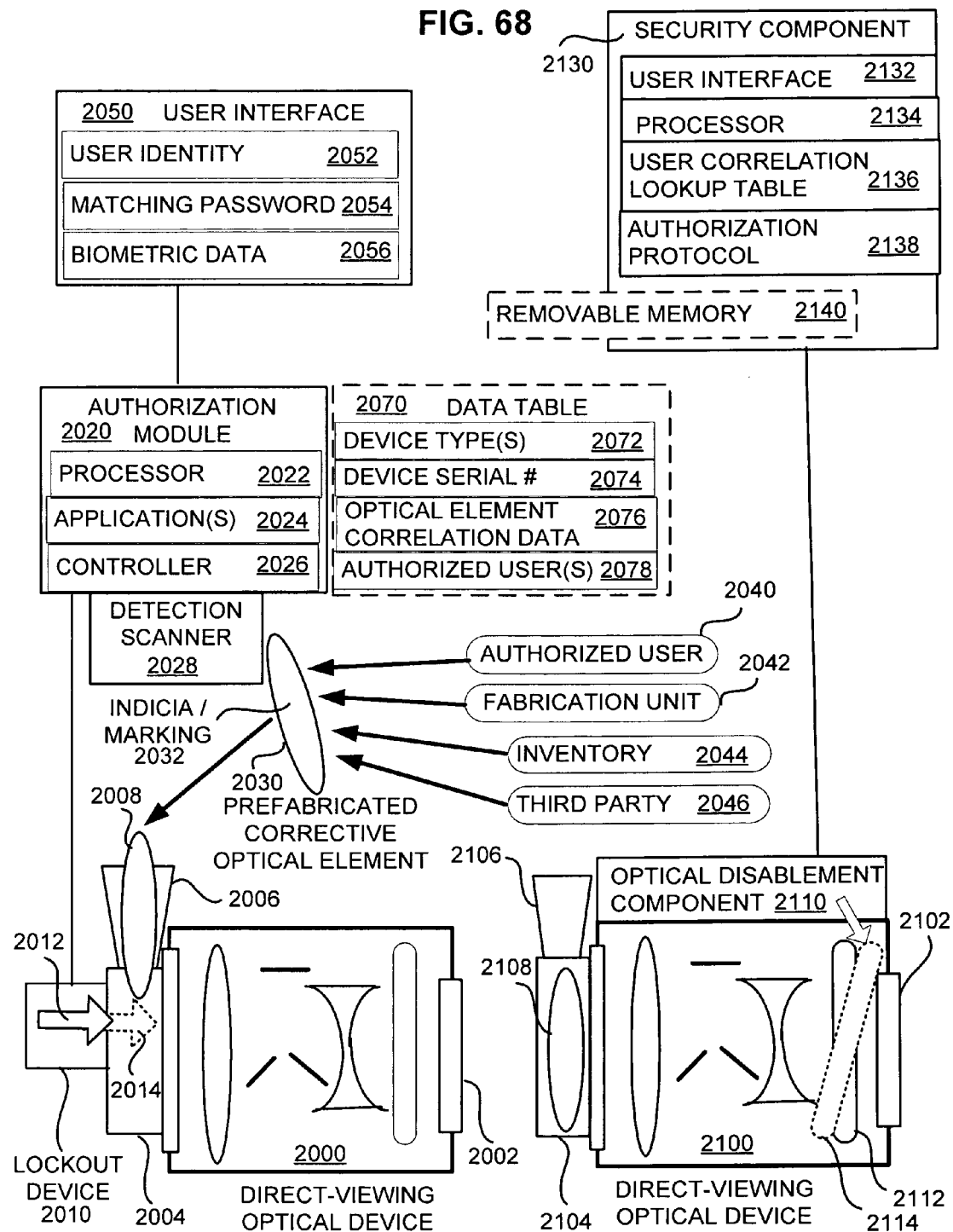
FIG. 68 is a further schematic block diagram illustrating various exemplary embodiment features incorporated in a system for customized installation of replaceable corrective optical elements for a direct-viewing optical device.

Referring to the schematic block diagram of FIG. 68, various exemplary embodiment features are depicted regarding different prefabricated corrective optical elements (e.g., 2008, 2108, 2030) that are each adapted for removable installation in one or more direct-viewing optical devices 2000, 2001. It will be understood that such prefabricated corrective optical elements may be accepted for possible installation from an authorized user 2040, a fabrication unit 2042, an inventory 2044 and in some instances from a third party 2046. Other sources may be available depending on the circumstances of usage as well as the type and location of each direct-viewing optical device.

Some embodiments may provide an authorization module 2020 that includes processor 2022, one or more program applications 2024, and controller 2026 to enable data processing for security protection and appropriate matchup between prospective users and correlated corrective optical elements (e.g., its aberrational correction parameters) and intended destinations as interchangeable operative components for one or more direct-viewing optical devices. The authorization module 2020 may be linked to user interface 2050 that is adapted for recognizing a user identity 2052, a matching password 2054, and in some instances detectable biometric data associated with the user identity 2052.

A detection scanner 2028 may be operatively connected with the authorization module 2020 in order to obtain scanned informational data from indicia and/or marking 2032 incorporated as part of the prefabricated corrective optical element 2030. Such indicia or marking 2032 may in some instances be easily read without special equipment. However in some instances the indicia or marking 2032 may be encoded or hidden or not easily recognizable depending on applicable security and usage guidelines. Additional informational data may be obtainable from a local or remote data table 2070 that includes correlation data regarding multiple direct-viewing optical devices 2072, optical device serial numbers 2074, optical element correlation data 2076, and a listing of authorized users 2078 for such devices 2072, 2074 and such optical corrective elements 2076.

Possible embodiment features for the direct-viewing optical device 2000 having aperture 2002 may include an eyepiece 2004 having a mounting receptacle 2006 that is configured for removable installation of prefabricated corrective optical element 2008. An additional security feature may include a mechanical-type lockout device that is actuated pursuant to direct or indirect control from authorization module 202. In the event that any of the applicable authorization matchups are not determined by authorization module 2020 and its related data sources, a physical barrier or rod 2012 or other blocking component may be moved into a lockout position (see 2014) or remain in such lockout position (see 2014) to prevent unauthorized installation of the prefabricated corrective optical element 2008. Additional types of preemptive mechanical-related disruptions may include a spring-loaded ejection or a physical vibration of the prefabricated corrective optical element after installation (e.g., a piezoelectric vibration actuator).

Possible embodiment features for the direct-viewing optical device 2100 having aperture 2102 may include eyepiece 2104 having a mounting receptacle 2106 configured for removable installation of prefabricated corrective optical element 2108. However another protection feature may include a security component 2130 having user interface 2132, processor 2134, and user correlation lookup table 2136. In accordance with an authorization protocol 2138, the security component 2130 can be adapted to establish proper user identity, and to determine whether the prefabricated corrective optical element 2108 is intended for operative installation in direct-viewing optical device 2100. A further feature of security component 2130 may include making a determination regarding an authorized correlation between an established user identity and the prefabricated corrective optical element 2108 (e.g., its aberrational corrective parameters).

In the event that any of the applicable authorization matchups are not successfully established by security component 2130 and its related data sources (e.g., see removable memory 2140), an optical disablement component 2110 may be activated to cause partial or complete malfunction of a functional aspect of the direct-viewing optical device 2100. Examples of such optical disablement malfunctions may include a distortion of optical acuity, turning off an illuminating light source, causing misalignment of an optical viewing axis (e.g., see transmissive element 2112 pivoted into misaligned position 2114), or a blocking the optical path by activating a shutter or opaque filter or the like.

As shown in the embodiments of FIG. 68, some preemptive malfunctions may be accomplished even though the prefabricated corrective optical elements 2008, 2108 are already installed in eyepiece 2104. Of course it will be understood that other types of security protection and matchup schemes that prevent unauthorized installation or preempt functional operation may be implemented, and in some circumstances the illustrated embodiments may be modified or enhanced in accordance with the teachings and examples disclosed herein. Some processing functions in various disclosed system components (e.g., user interface 2050, lockout device 2010, optical disablement component 2104, authorization module 2020, security component 2130) may be implemented in circuitry as well as in software programs depending on the circumstances.

It will be understood that various exemplary embodiments disclosed herein provide a system for customized installation of a replaceable corrective optical element wherein a direct-viewing optical device includes a mounting receptacle feature configured for removable installation of a prefabricated optical element having customized corrective parameters. A further system component may provide a user interface adapted to confirm that a prospective user identity is approved for use of the direct-viewing optical device.

Another possible system aspect may provide an authorization module for determining a correlation between the prospective user identity and the customized corrective parameters of the prefabricated optical element. Additional security features may be incorporated in the authorization module to determine the aforesaid correlation by scanning or reading a marking or indicia on the prefabricated optical element. Some system security provisions may include an authorization module configured to determine such correlation by accessing a correlation data table record located proximate or remotely relative to the direct-viewing optical device.

Further system possibilities may include an authorization module configured for determining whether the prefabricated optical element is meant for intended installation on the direct-viewing optical device. The authorization module may be further configured to determine such intended installation by scanning or reading a marking or indicia on the prefabricated optical element. In some instances the authorization module may be further configured to determine such intended installation by accessing a correlation data table record located proximate or remotely relative to the direct-viewing optical device.

As a further security enhancement, an exemplary system embodiment may include a mechanical lockout component operatively linked with a user interface in a manner to prevent successful operative installation of the prefabricated corrective optical element in response to a failure to confirm that the prospective user identity is approved for use of the direct-viewing optical device. Another security implementation feature may provide a mechanical lockout component adapted to prevent successful operative installation of the prefabricated corrective optical element in response to a determination of an absence of correlation between the prospective user identity and the customized corrective parameters of the prefabricated optical element.

Additional protection features may be incorporated in a mechanical lockout device operatively linked with an authorization module and adapted to prevent successful operative installation of the prefabricated corrective optical element in response to a determination that the prefabricated optical element is not meant for intended installation on the directive-viewing optical device.

It will be understood that some exemplary system embodiments disclosed herein include an optical disablement feature operatively linked with a user interface in a manner to cause partial or complete malfunction of a functional aspect of the direct-viewing optical device in response to a failure to confirm that the prospective user identity is approved for use of the direct-viewing optical device. An optical disablement component may be adapted for causing a partial or complete malfunction of a functional aspect of the direct-viewing optical device in response to a determination of an absence of correlation between the prospective user identity and the customized corrective parameters of the prefabricated optical element.

In some instances a system security benefit may be achieved by providing an optical disablement component operatively linked with an authorization module and configured to cause partial or complete malfunction of a functional aspect of the direct-viewing optical device in response to a determination that the prefabricated optical element is not meant for intended installation on the directive-viewing optical device.

Figure 69:
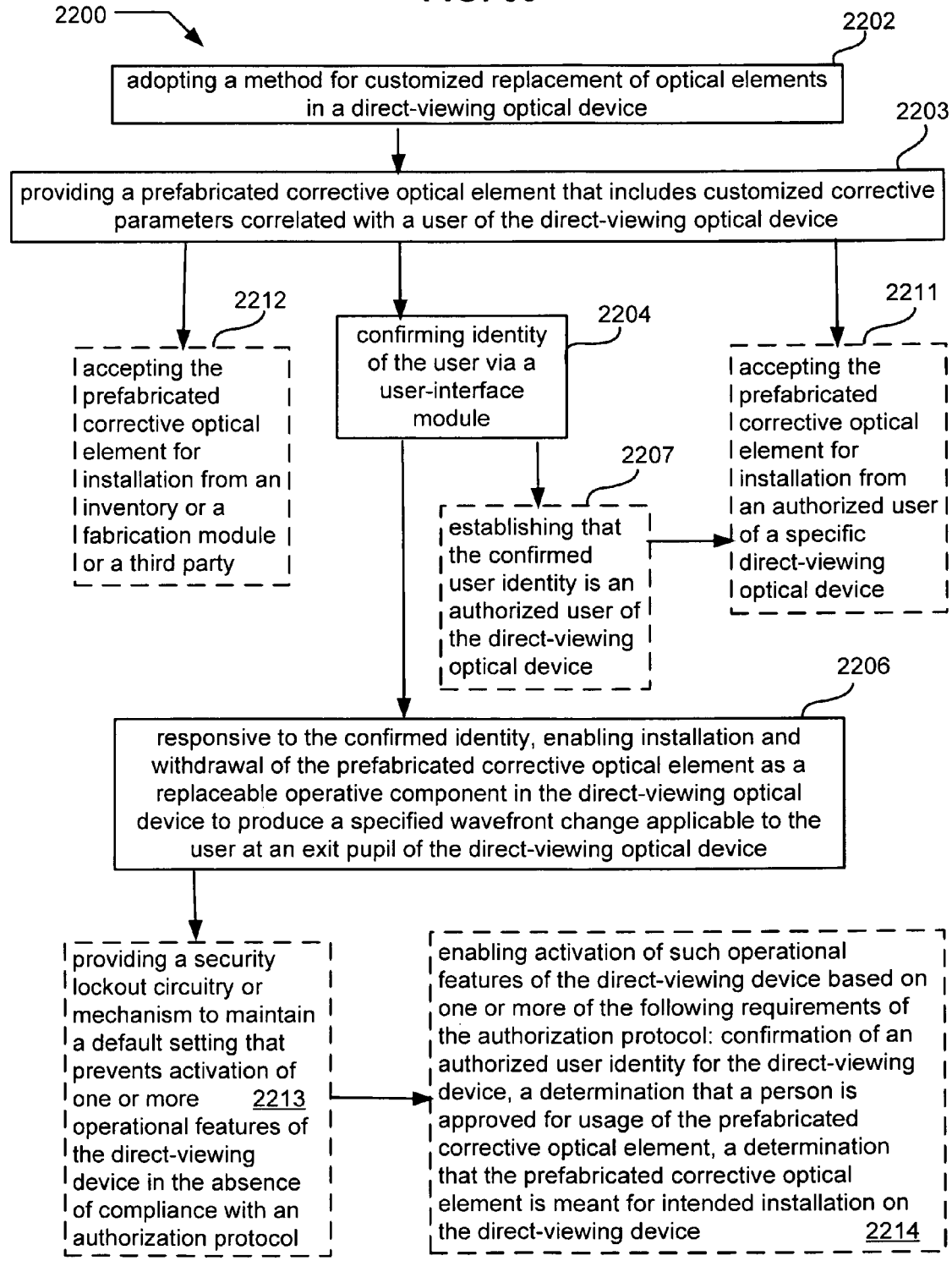
FIG. 69 is a high level flow chart that shows additional exemplary method aspects for installation of interchangeable corrective optical elements in a direct-viewing optical device.

Referring to the high level flow chart of FIG. 69, various possible aspects 2200 are depicted in connection with adopting a method for customized replacement of optical elements in a direct-viewing optical device (see operation 2202). Such an exemplary method may include providing a prefabricated corrective optical element that includes customized corrective parameters correlated with a user of the direct-viewing optical device (block 2203); confirming identity of the user via a user interface module (block 2204); and responsive to the confirmed identity, enabling installation and withdrawal of the prefabricated corrective optical element as a replaceable operative component in the direct-viewing optical device to produce a specified wavefront change applicable to the user at an exit pupil of the direct-viewing optical device (block 2206). Another method example includes establishing that the confirmed user identity is an authorized user of the direct-viewing optical device (block 2207).

Additional enhancement possibilities include accepting the prefabricated corrective optical element for installation from an authorized user of a specific direct-viewing optical device (block 2211), and in some instances accepting the prefabricated corrective optical element for installation from an inventory or a fabrication module or a third party (block 2212).

In some circumstances it may be very desirable to implement certain authorization guidelines incorporated in a user interface module or other security component as part of an authorization protocol regarding acceptance and/or installation and/or usage of the prefabricated corrective optical elements by an authorized user of a specific direct-viewing optical device.

Some embodiments may include providing a security lockout circuitry or mechanism to maintain a default setting that prevents activation of one or more operational features of the direct-viewing device in the absence of compliance with an authorization protocol (block 2213). A further example feature includes enabling activation of such operational features of the direct-viewing device based on one or more of the following requirements of the authorization protocol: confirmation of an authorized user identity for the direct-viewing device, a determination that a person is approved for usage of the prefabricated corrective optical element, a determination that the prefabricated corrective optical element is meant for intended installation on the direct-viewing device (block 2214).

As shown in the detailed flow chart of FIG. 70, various exemplary process aspects 2220 include previously described operations 2203, 2204, 2206 in combination with establishing the user identity by name or password or biometric match or eye feature recognition (block 2221). Another authorization feature may include making a determination that the confirmed user identity is an intended person approved for usage of the prefabricated corrective optical element (block 222). A related example includes making such determination regarding the intended person by scanning or reading a corresponding marking or indicia on the prefabricated corrective optical element (block 2223). Another illustrated example includes making such determination regarding the intended person by accessing an authorization data table (block 2224).

Further examples regarding authorized user guidelines may include selecting the prefabricated corrective optical element that includes detectable reference indicia or individualized marking indicative of the user. (block 2227). A further possibility includes maintaining a data record listing a user identity respectively associated with a prefabricated corrective optical element that was recycled and kept in inventory for future use (block 2226). Another authorization example includes maintaining the on-board memory or removable memory that includes an encoded or encrypted user identity that is correlated with the customized corrective parameters (block 2228).

The detailed flow chart of FIG. 71 illustrates various embodiment features 2230 that include previously described process aspects 2203, 2204, 2206 along with making a determination that the prefabricated corrective optical element is meant for intended installation on the direct-viewing optical device (block 2232). Further process examples regarding authorized installation include making such determination regarding the intended installation by scanning or reading a corresponding marking or indicia on the prefabricated corrective optical element (block 2233). Another related process example includes selecting the prefabricated corrective optical element that includes detectable reference indicia or individualized marking indicative of a specific direct-viewing optical device (block 2234).

Additional authorization possibilities include providing a mounting receptacle that is uniquely formatted for accepting only the prefabricated corrective optical element intended for use with a specific direct-viewing optical device (block 2336). A related aspect includes selecting the prefabricated corrective optical element that includes a definitive external size and/or shape corresponding to a mounting receptacle of a specific direct-viewing optical device (block 2337). Another process example includes locking via a selective latching mechanism an acceptable prefabricated corrective optical element in operative position (block 2239).

Referring to the detailed flow chart of FIG. 72, illustrated embodiment features 2240 include previously described process aspects 2203, 2204, 2206 which may be combined with flexible usage requirements that include selecting the prefabricated corrective optical element that is configured to be the replaceable operative component for more than one specific or more than one type of direct-viewing optical device (block 2242). Other related process examples include incorporating a standardized mounting format in more than one type of direct-viewing optical device to enable insertion and withdrawal of the prefabricated corrective optical element as the replaceable operative component in different direct-viewing optical devices (block 2243).

Some embodiments may provide authorization features that include providing a selective mounting format that prevents installation of an unacceptable prefabricated corrective optical element intended for use in a different direct-viewing optical device (block 2244). A further authorization enhancement may include incorporating a mechanical lockout device with a mounting receptacle to prevent successful operative installation of the prefabricated corrective optical element in response to one or more of the following: failure to confirm an authorized user identity for the direct-viewing device, a determination that a person is not approved for usage of the prefabricated corrective optical element, a determination that the prefabricated corrective optical element is not meant for intended installation on the direct-viewing device (block 2246).

A further security possibility includes activating an optical disablement component to cause partial or complete malfunction of a functional aspect of the direct-viewing device in response to one or more of the following: failure to confirm an authorized user identity for the direct-viewing device, a determination that a person is not approved for usage of the prefabricated corrective optical element, a determination that the prefabricated corrective optical element is not meant for intended installation on the direct-viewing device (block 2247).

It will be understood from the various disclosed embodiments that many individual method operations depicted in the flow charts of FIGS. 69-72 can be incorporated as encoded instructions in computer readable media in order to obtain enhanced benefits and advantages regarding interchangeable corrective optical elements.

The exemplary system, apparatus, and computer program product embodiments disclosed herein including FIGS. 1-5, FIGS. 15-18, FIGS. 29-30, FIGS. 38-40, FIGS. 47-49, FIGS. 58-61, and FIGS. 67-68 along with other components, devices, know-how, skill and techniques known in the art have the capability of implementing and practicing the methods and processes depicted in FIGS. 6-14, FIGS. 19-28, FIGS. 31-37, FIGS. 41-46, FIGS. 50-57, FIGS. 62-66, and FIGS. 69-72. However it is to be further understood by those skilled in the art that other systems, apparatus and technology may be used to implement and practice such methods and processes.

It will be understood by those skilled in the art that the various components and elements disclosed in the system and schematic diagrams herein as well as the various steps and sub-steps disclosed in the flow charts herein may be incorporated together in different claimed combinations in order to enhance possible benefits and advantages.

Exemplary methods, systems and components enable an enhanced direct-viewing optical device to include customized adjustments that accommodate various optical aberrations of a current user. A real-time adjustment of transformable optical elements is sometimes based on predetermined corrective optical parameters associated with a current user. Customized optical elements associated with an authorized current user are incorporated with the direct-viewing optical device to produce a specified change in optical wavefront at an exit pupil. Possible replacement optical elements may have refractive and/or reflective and/or diffractive and/or transmissive characteristics that are selected based on current performance viewing factors for a given field of view of the direct-viewing device. Some embodiments enable dynamic repositioning and/or transformation of corrective replaceable optical elements responsive to a detected shift of a tracked gaze direction of a current user. Replaceable interchangeable corrective optical elements may be fabricated for current usage or retained in inventory for possible future usage in designated direct-viewing devices.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for customized replacement of optical elements in a direct-viewing optical device, comprising:
   providing two or more prefabricated corrective optical elements that include customized corrective parameters correlated with two or more users of the direct-viewing optical device, the direct-viewing optical device comprising one or more of a microscope, a telescope, binoculars, a weapon sight, a gun sight, a diagnostic tool, a manufacturing inspection device, and a hand-held device;
   confirming identity of a current user via a user-interface module;
   responsive to confirming the identity, enabling automated installation and withdrawal of at least one of the two or more prefabricated corrective optical elements as a replaceable operative component in the direct-viewing optical device to produce a specified wavefront change applicable to the current user at an exit pupil of the direct-viewing optical device; and
   activating an optical disablement component to cause partial or complete optical malfunction to mechanically disable usage of the direct-viewing optical device in response to one or more of the following:
      a failure to confirm an authorized user identity for the direct-viewing optical device,
      a determination that a person is not approved for usage of the prefabricated corrective optical element, and
      a determination that the prefabricated corrective optical element is not meant for intended installation on the direct-viewing optical device.

2. The method of claim 1 wherein said providing the two or more prefabricated corrective optical element includes:
   selecting the at least one prefabricated corrective optical element that includes a definitive external size and/or shape corresponding to a mounting receptacle of a specific direct-viewing optical device.

3. The method of claim 1 wherein said providing the two or more prefabricated corrective optical element includes:
   selecting the at least one prefabricated corrective optical element that includes detectable reference indicia or individualized marking indicative of the current user.

4. The method of claim 1 wherein said providing the two or more prefabricated corrective optical element includes:
   selecting the at least one prefabricated corrective optical element that includes detectable reference indicia or individualized marking indicative of a specific direct-viewing optical device.

5. The method of claim 1 wherein said providing the two or more prefabricated corrective optical element includes:
   selecting the at least one prefabricated corrective optical element that includes customized corrective parameters applicable to an operating condition or image property or viewing environment obtained by a sensor for a given field of view of the direct-viewing optical device.

6. The method of claim 1 wherein said providing the two or more prefabricated corrective optical element includes:
   selecting the at least one prefabricated corrective optical element that includes customized corrective parameters to ameliorate low order and/or high order aberrations of the current user.

7. The method of claim 1 further comprising:
   incorporating the at least one prefabricated corrective optical element as the replaceable operative component in one of the following types of specific direct-viewing optical device: microscope, telescope, binoculars, weapon sight, gun sight, medical instrument, diagnostic tool, manufacturing inspection device, head-mounted, body-mounted, hand-held, independently supported.

8. The method of claim 1 further comprising:
   obtaining information indicating a right eye or left eye or both eyes of the current user which correspond to the predetermined customized corrective parameters of the at least one prefabricated corrective optical element.

9. The method of claim 1 further comprising:
   making a determination whether the current user will require both low-level and higher-level aberrational correction implemented in the at least one prefabricated optical element, because of removal or other absence of any prescription eyeglasses or any prescription contact lenses during an optical device usage period.

10. The method of claim 9 further comprising:
    responsive to the determination, selecting an appropriate prefabricated corrective optical element that includes predetermined corrective parameters to ameliorate both low-level and higher-level aberrations of the current user.

11. The method of claim 1 wherein said providing the two or more prefabricated corrective optical element includes:
    selecting one of the following types of prefabricated corrective optical elements: eyepiece, insert between a user's eye and an eyepiece, insert between an eyepiece and a remainder optical device portion, right eye component, left eye component, both eyes component.

12. The method of claim 1 further comprising:
    maintaining for safekeeping an inventory of the two or more prefabricated corrective optical elements respectively associated with different users of one or more direct-viewing optical devices.

13. The method of claim 1 further comprising:
    providing a mounting receptacle that is uniquely formatted for accepting only a prefabricated corrective optical element intended for use with a specific direct-viewing optical device.

14. The method of claim 1 further comprising:
    wherein activating the optical disablement component comprises causing a translational or rotatable movement of an installed prefabricated corrective optical element between an off-line position and an on-line position relative to an optical viewing path of the direct-viewing optical device.

15. The method of claim 1 further comprising:
    incorporating a standardized mounting format in more than one type of direct-viewing optical device to enable insertion and withdrawal of the at least one prefabricated corrective optical element as the replaceable operative component in different direct-viewing optical devices.

16. The method of claim 1 further comprising:
locking via a selective latching mechanism an acceptable prefabricated corrective optical element in operative position.

17. The method of claim 1 further comprising:
providing a selective mounting format that prevents installation of an unacceptable prefabricated corrective optical element intended for use in a different direct-viewing optical device.

18. The method of claim 1 wherein the optical disablement component is configured to selectively cause partial or complete optical malfunction by one or more of distorting of optical acuity, causing misalignment of an optical viewing axis, and blocking an optical viewing path of the direct viewing optical device.

19. A computer program product comprising non-transitory computer-readable media having encoded instructions for executing a method for customized replacement of optical elements in a direct-viewing optical device, wherein the method includes the following operations:
detecting identity of a current user of a direct-viewing optical device, the direct-viewing optical device capable of selectively receiving a prefabricated corrective optical element of a plurality of prefabricated corrective optical elements that include customized corrective parameters correlated with two or more users;
enabling automated insertion or automated withdrawal of the prefabricated corrective optical element as the replaceable operative component in the direct-viewing optical device, the direct-viewing optical device comprising one or more of a microscope, a telescope, binoculars, a weapon sight, a gun sight, a diagnostic tool, a manufacturing inspection device, and a hand-held device;
responsive to the confirmed identity, activating the direct-viewing optical device after confirmed installation of the prefabricated corrective optical element as a replaceable operative component in the direct-viewing optical device to produce a specified wavefront change applicable to the user at an exit pupil of the direct-viewing optical device; and
activating an optical disablement component to cause partial or complete optical malfunction to mechanically disable usage of the direct-viewing optical device in response to one or more of the following:
a failure to confirm an authorized user identity for the direct-viewing optical device,
a determination that a person is not approved for usage of the prefabricated corrective optical element, and
a determination that the prefabricated corrective optical element is not meant for intended installation on the direct-viewing optical device.

20. The computer program product of claim 19 further including encoded instructions for the following operation:
confirming installation of the prefabricated corrective optical element that is recyclable after removal as the replaceable operative component, to be kept in inventory for possible future use by the current user of the direct-viewing optical device.

21. The computer program product of claim 20 further including encoded instructions for the following operation:
maintaining a data record listing a user identity respectively associated with the prefabricated corrective optical element that was recycled and kept in inventory for future use.

22. The computer program product of claim 19 further including encoded instructions for the following operation:
confirming installation of the prefabricated corrective optical element that is capable of being transformable and/or rewriteable after removal as the replaceable operative component, to be kept in inventory for possible future use by a different user of the direct-viewing optical device.

23. The computer program product of claim 19 further including encoded instructions for the following operation:
confirming installation of the prefabricated corrective optical element that is intended to be disposable after removal as the replaceable operative component of the direct-viewing optical device.

24. The computer program product of claim 19 further including encoded instructions for the following operation:
confirming insertion and/or withdrawal of the prefabricated corrective optical element as the replaceable operative component in the direct-viewing optical device.

25. The computer program product of claim 19 further including encoded instructions for the following operation:
making a determination that the prefabricated corrective optical element is meant for intended installation on the direct-viewing optical device.

26. The computer program product of claim 25 wherein said making the determination that the prefabricated corrective optical element is meant for intended installation on the direct-viewing optical device includes:
making such determination regarding the intended installation by scanning or reading a corresponding marking or indicia on the prefabricated corrective optical element.

27. The computer program product of claim 19 further including encoded instructions for the following operation:
implementing a mechanical lockout device to prevent successful operative installation in the mounting receptacle of the prefabricated corrective optical element in response to one or more of the following: failure to confirm an authorized user identity for the direct-viewing optical device, a determination that a person is not approved for usage of the prefabricated corrective optical element, a determination that the prefabricated corrective optical element is not meant for intended installation on the direct-viewing optical device.

28. The computer program product of claim 19 further including encoded instructions for the following operation:
activating a security lockout circuitry or mechanism to maintain a default setting that prevents activation of one or more functional aspects of the direct-viewing optical device in the absence of compliance with an authorization protocol.

29. The computer program product of claim 28 further including encoded instructions for the following operation:
enabling activation of such functional aspects of the direct-viewing optical device based on one or more of the following requirements of the authorization protocol: confirmation of an authorized user identity for the direct-viewing optical device, a determination that a person is approved for usage of the prefabricated corrective optical element, a determination that the prefabricated corrective optical element is meant for intended installation on the direct-viewing optical device.

30. A system for customized installation of a replaceable corrective optical element comprising:
a direct-viewing optical device including a mounting receptacle configured for removable installation of a prefabricated optical element of a plurality of prefabricated optical elements having customized corrective parameters, the direct-viewing optical device comprising one or more of a microscope, a telescope, binoculars, a weapon sight, a gun sight, a diagnostic tool, a manufacturing inspection device, and a hand-held device;

an inventory unit for maintaining for safekeeping an inventory including the plurality of prefabricated optical elements respectively associated with two or more users of the direct-viewing optical device and for enabling automated insertion or automated withdrawal of the prefabricated optical element as the replaceable operative component in the direct-viewing optical device;

a user-interface module adapted to confirm that a prospective user identity is approved for use of the direct-viewing optical device;

an authorization module for determining a correlation between the prospective user identity and the customized corrective parameters of the prefabricated optical element; and an optical disablement component operatively linked with the authorization module and adapted to cause partial or complete optical malfunction to mechanically disable usage of the direct-viewing optical device in response to one or more of:

a failure to confirm that the prospective user identity is approved for use of the direct-viewing optical device;

a determination of an absence of correlation between the prospective user identity and the customized corrective parameters of the prefabricated optical element; and a determination that the prefabricated optical element is not meant for intended installation on the direct-viewing optical device.

31. The system of claim 30 wherein said authorization module is configured to determine such correlation by scanning or reading a marking or indicia on the prefabricated optical element.

32. The system of claim 30 wherein said authorization module is configured to determine such correlation by accessing a correlation data table record located proximate or remotely relative to the direct-viewing optical device.

33. The system of claim 30 wherein said authorization module is configured for determining whether the prefabricated optical element is meant for intended installation on the direct-viewing optical device.

34. The system of claim 33 wherein said authorization module is further configured to determine such intended installation by scanning or reading a marking or indicia on the prefabricated optical element.

35. The system of claim 33 wherein said authorization module is further configured to determine such intended installation by accessing a correlation data table record located proximate or remotely relative to the direct-viewing optical device.

36. The system of claim 30 further comprising:

a mechanical lockout operatively linked with the authorization module and/or with the user-interface module, and adapted to prevent successful operative installation of the prefabricated corrective optical element in response to a failure to confirm that the prospective user identity is approved for use of the direct-viewing optical device.

37. The system of claim 30 further comprising:

a mechanical lockout operatively linked with the authorization module and/or with the user-interface module, and adapted to prevent successful operative installation of the prefabricated corrective optical element in response to a determination of an absence of correlation between the prospective user identity and the customized corrective parameters of the prefabricated optical element.

38. The system of claim 30 further comprising:

a mechanical lockout operatively linked with the authorization module and adapted to prevent successful operative installation of the prefabricated corrective optical element in response to a determination that the prefabricated optical element is not meant for intended installation on the directive-viewing optical device.

* * * * *